（12）United States Patent
Nunokawa et al.

(10) Patent No.: US 6,943,196 B1
(45) Date of Patent: *Sep. 13, 2005

(54) NF-κB INHIBITOR COMPRISING PHENYLMETHYL BENZOQUINONE AS THE ACTIVE INGREDIENT

(75) Inventors: Yoichi Nunokawa, Toyonaka (JP); Kenji Suzuki, Osaka (JP); Masayuki Saitoh, Ibaraki (JP)

(73) Assignee: Daiichi Suntory Pharma Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/424,059

(22) PCT Filed: Mar. 19, 1999

(86) PCT No.: PCT/JP99/01422

§ 371 (c)(1),
(2), (4) Date: Nov. 18, 1999

(87) PCT Pub. No.: WO99/48491

PCT Pub. Date: Sep. 3, 1999

(30) Foreign Application Priority Data

Mar. 20, 1998 (JP) .......................................... 10-092431

(51) Int. Cl.[7] ...................... A61K 45/00; A61K 31/122; A61K 31/192; A61P 9/04; C07C 50/04
(52) U.S. Cl. ....................... 514/688; 514/532; 514/544; 514/570; 514/621; 514/622; 514/679; 514/733; 514/736; 552/293; 560/51; 560/57; 544/56; 544/120; 546/257; 562/459; 562/468
(58) Field of Search ................................ 552/293, 307; 544/56, 120; 546/257; 514/688, 679

(56) References Cited

U.S. PATENT DOCUMENTS 6,703,421 B1 * 3/2004 Nunokawa et al. ......... 514/532
2004/0030129 A1 * 2/2004 Nunokawa et al. ............ 544/59

FOREIGN PATENT DOCUMENTS

| EP | 0864648 | * 9/1998 | ........... C12N/15/09 |
|---|---|---|---|
| JP | 62-286949 | 12/1987 | |
| JP | 4-226937 | 8/1992 | |
| WO | 98/12313 | 3/1998 | |

OTHER PUBLICATIONS

Suzuki et al. Chem. Pharm.Bull., 1996, vol. 41(1), 139–144.*
Database WPI, Section Ch, Week 199602, Derwent Publication Ltd., XP 002240470 & JP 07291860, Nov. 7, 1995, Abstract.
Database WPI, Section Ch, Week 199602, Derwent Publications Ltd., XP 002240471 & JP 07291859, Nov. 7, 1995, Abstract.

Salvador Moncada, M.D., et al., "The L–Arginine–Nitric Oxide Pathway," The New England Journal of Medicine, vol. 329, No. 27, pp. 2002–2012, 1993.

Ulrich Forstermann et al, "Properties, Cellular Distribution and Expressional Control," Biochemical Pharmacology, vol. 50, No. 9, pp. 1321–1332, 1995.

V. Cattell et al, "Inducible Nitric Oxide Synthase in Inflammation," Histochemical Journal, vol. 27, pp. 777–784, 1995.

Andreas K. Nussler et al, "Inflammation, Immunoregulation, and Inducible Nitric Oxide Synthase," Journal of Leukocyte Biology, vol. 54, pp. 171–178, 1993.

S. Moncada et al, "Molecular Mechanisms and Therapeutic Strategies Related to Nitric Oxide," The FASEB Journal, vol. 9, pp. 1319–1330, 1995.

Xiao–qing Wei et al, "Altered Immune Responses in Mice Lacking Inducible Nitric Oxide Synthase," Nature, vol. 375, pp. 408–411, 1995.

(Continued)

Primary Examiner—James O. Wilson
Assistant Examiner—Tamthom N. Truong
(74) Attorney, Agent, or Firm—Burns, Doane, Swecker & Mathis, L.L.P.

(57) ABSTRACT

An NF-κB inhibitor having as an active ingredient a benzoquinone derivative represented by the general formula (1) wherein $R_1$, $R_2$, and $R_3$ are each independently H, alkyl having 1 to 5 carbons, or alkoxy having 1 to 5 carbons; $R_4$ is H, hydroxymethyl, alkyl, or carboxyl which is optionally esterified or amidated; Z is represented by the formula (A); and, n is an integer from 0 to 6, or its hydroquinone form or a pharmaceutically acceptable salt thereof.

9 Claims, 6 Drawing Sheets

OTHER PUBLICATIONS

Jill E. Ogden et al, "Inhibition of Nitric Oxide Synthase—Potential for a Novel Class of Therapeutic Agent," Tibtech, vol. 13, pp. 70–78, 1995.

R. Davis Manning, Jr. et al, "Cardiovascular Responses to Long–Term Blockade of Nitric Oxide Synthesis," Hypertension, vol. 22, No. 1, pp. 40–48, 1993.

Garry J. Southan et al, "Selective Pharmacological Inhibition of Distinct Nitric Oxide Synthase Isoforms," Biochemical Pharmacology, vol. 51, pp. 383–394, 1996.

Pierre Vassalli et al, "The Pathophysiology of Tumor Necrosis Factors," Annu. Rev. Immunol., vol. 10, pp. 411–452, 1992.

Yasutoshi Muto et al, "Enhanced Tumour Necrosis Factor and Interleukin–1 in Fulminant Hepatic Failure," The Lancet, pp. 72–74, 1998.

Mohammad K. Sharief, M.B. et al, "Association Between Tumor Necrosis Factor–α and Disease Progression in Patients with Multiple Sclerosis," vol. 325, No. 7, pp. 467–472, 1991.

Ciro Tetta et al, "Tumour Necrosis Factor in Serum and Synovial Fluid of Patients with Active and Severe Rheumatoid Arthritis," Annals of the Rheumatic Diseases, vol. 49, pp. 665–667, 1990.

G. Venn et al, "Elevated Synovial Fluid Leels of Interleukin–6 and Tumor Necrosis Factor Associated with Early Experimental Canine Osteoarthritis," Arthritis and Rheumatism, vol. 36, No. 6, pp. 819–826, 1993.

Michael J. Elliott et al, "Repeated Therapy with Monoclonal Antibody to Tumour Necrosis Factor α (cA2) in pateitns with Rheumatoid Arthritis," The Lancet, vol. 344, pp. 1125–1127, 1994.

Michael J. Elliott et al, "Randomised Double–Blind Comparison of Chimeric Monoclonal Antibody to Tumour Necrosis Factor α (cA2) Versus Placebo in Rheumatoid Arthritis," The Lancet, vol. 344, pp. 1105–1110, 1994.

E. C. C. Rankin et al, "The Therapeutic Effects of an Engineered Human Anti–Tumour Necrosis Factor Alpha Antibody (CDP571) in Rheumatoid Arthritis," British Journal of Rheumatology, vol. 34, pp. 334–342, 1995.

Jean–Louis Vincent, M.D. et al, "Administration of Anti–TNF Antibody Improves Left Ventricular Function in Septic Shock Patients," Chest, vol. 101, No. 3, pp. 810–815, 1992.

L.B. Hinshaw et al., "Survival of Primates in $LD_{100}$ Septic Shock Following Therapy with Antibody to Tumor Necrosis Factor (TNFα)," Circulatory Shock, vol. 30, pp. 279–292, 1990.

U. Nyman et al, "Amelioration of Collagen II–Induced Arthritis in Rats by the Type IV Phosphodiesterase Inhibitor Rolipram," Clin. Exp. Immunol. vol. 108, pp. 415–419, 1997.

Timothy S. Blackwell et al, "The Role of Nuclear Factor–κB in Cytokine Gene Regulation," Am. J. Respir. Cell Mol. Biol., vol. 17, pp. 3–9, 1997.

C. Victor Jongeneel, "Regulation of the TNFα Gene," Bacterial Endotoxins: Basic Science to Anti–Sepsis Strategies, pp. 367–381, 1994.

Qiao–wen Xie et al, "Role of Transcription Factor NF–κB/Rel in Induction of Nitric Oxide Synthase," The Journal or Biological Chemistry, vol. 269, No. 7, pp. 4705–4708, 1994.

Youichi Nunokawa et al, "Human Inducible Nitric Oxide Synthase Gene is Transcriptionally Regulated by Nuclear Factor–κB Dependent Mechanism," Biochemical and Biophysical Research Communications, vol. 223, pp. 347–352, 1996.

Tucker Collins et al, "Transcriptional Regulation of Endothelial Cell Adhesion Molecules: NF–κB and Cytokine–Inducible Enhancers," The FASEB Journal, vol. 9, pp. 899–909, 1995.

Patrick A. Baeuerle et al, "NF–κB as a Frequent Target for Immunosuppressive and Anti–Inflammatory Molecules," Advances in Immunology, vol. 65, pp. 111–137, 1997.

Bruce J. Dezube et al, "Cytokine Dysregulation in AIDS: In Vivo Overexpression of mRNA of Tumor Necrosis Factor–α and Its Correlation with That of the Inflammatory Cytokine GRO," Journal of Acquired Immune Deficiency Syndromes, vol. 5, pp. 1099–1104, 1992.

Gary Nabel et al, "An Inducible Transcription Factor Activates Expression of Human Immun odeficiency Virus in T Cells," Nature, vol. 326, pp. 711–713, 1987.

Fatermeh Fazely et al, "Pentoifylline (Trental) Decreases the Replication of the Human Immunodeficiency Virus Type 1 in Human Peripheral Blood Mononuclear Cells and in Cultured T Cells," Blood, Vo. 77, No. 8, pp. 1653–1656, 1991.

Eduardo Munoz et al, "Activation of NF–κB by the Tax Protein of HTLV–1", Immunobiol, vol. 193, pp. 128–136, 1995.

Nathalie Auphan et al, "Immunosuppression by Glucocorticoids: Inhibition of NF–κB Activity Through Induction of IκB Synthesis," Science, vol. 270, pp. 286–290, 1995.

Rodney E. Shackelford et al, "Aspirin Inhibits Tumor Necrosis Factor–α Gene Expression in Murine Tissue Macrophages," Molecular Pharmacology, vol. 52, pp. 421–429, 1997.

Vira Bitko et al, "Transcriptional Induction of Multiple Cytokines by Human Respiratory Syncytial Virus Requires Activation of NF–κB and is Inhibited by Sodium Salicylate and Aspirin," Virology, vol. 232, pp. 369–378, 1997.

Kenji Suzuki et al, "2–Arylmethyl–1,4–benzoquinones. I. Novel Inhibitors of Platelet Aggregation: Synthesis and Pharmacological Evaluation," Chem. Pharm. Bull, vol. 44, No. 1, pp. 139–144, 1996.

Mario C. Filion et al, "Anti–Inflammatory Activity of Cationic Lipids," British Journal of Pharmacology, vol. 122, pp. 551–557, 1997.

Peter W. Tsao et al, "The Effect of Dexamethasone on the Expression of Activated NF–κB in Adjuvant Arthritis," Clinical Immunology and Immunolopathology, vol. 83, No. 2, pp. 173–178, 1997.

Salvatore Cuzzocrea et al, "Antiinflammatory Effects of Mercaptoethylguanidine, A Combined Inhibitor of Nitric Oxide Synthase and Peroxynitrite Scavenger, in Carrageenan–Induced Models of Inflammation," Free Radical Biology & Medicine, vol. 24, No. 3, pp. 450–459, 1998.

Yoshiki Sawa et al, "A Novel Strategy for Myocardial Protection Using In Vivo Transfection of cis Element 'Decoy' Against NfkB Binding Site," Circulation, vol. 96, No. 9, pp. II–280–II–285, 1997.

Toshihiro Nakajima et al, "ES510 Antagonizes Thrombin Receptor Signals by Inhibiting NF–κB Activation," Biochemical and Biophysical Research Communications, vol. 203, No. 2, pp. 1181–1187, 1994.

Suzuki, Kenji et al., "2–Arylmethyl–1,4–benzoquinones. II. Novel Inhibitors of Platelet Aggregation: Synthesis and Pharmacological Evaluation." Chem. Pharm. Bull., 1997, vol. 45, No. 4, pp. 668–674.

Suzuki, Kenji et al., "2–Arylmethyl–1,4–benzoquinones. I. Novel Inhibitors of Platelet Aggregation: Synthesis and Pharmacological Evaluation." Chem. Pharm. Bull., 1996, vol. 44, No. 1, pp. 139–144.

* cited by examiner

Fig. 3
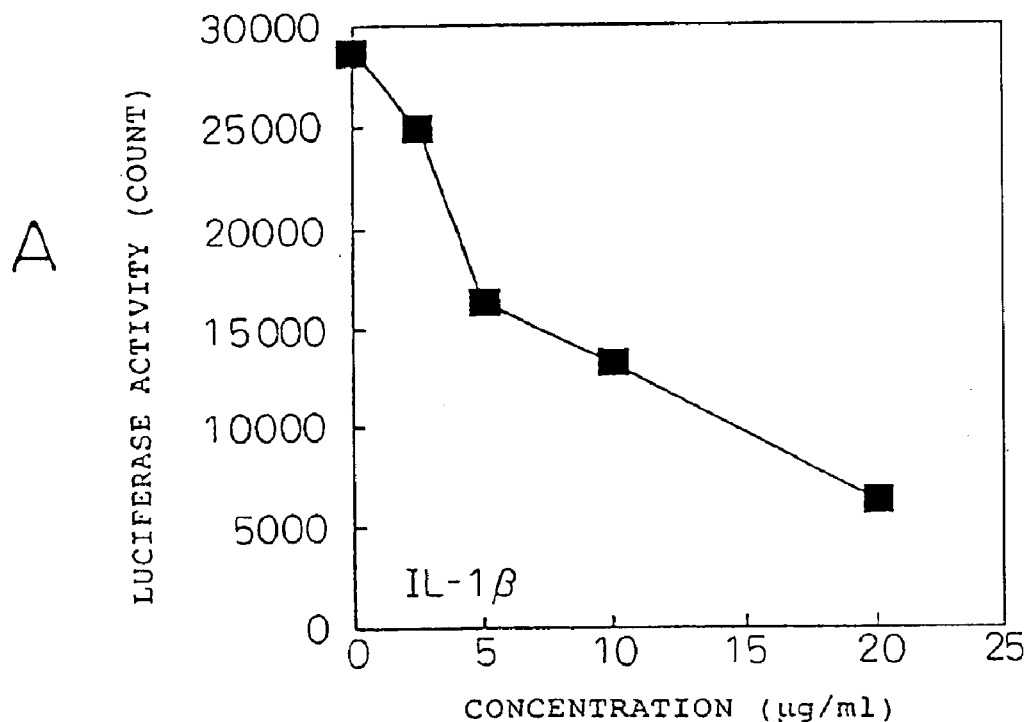
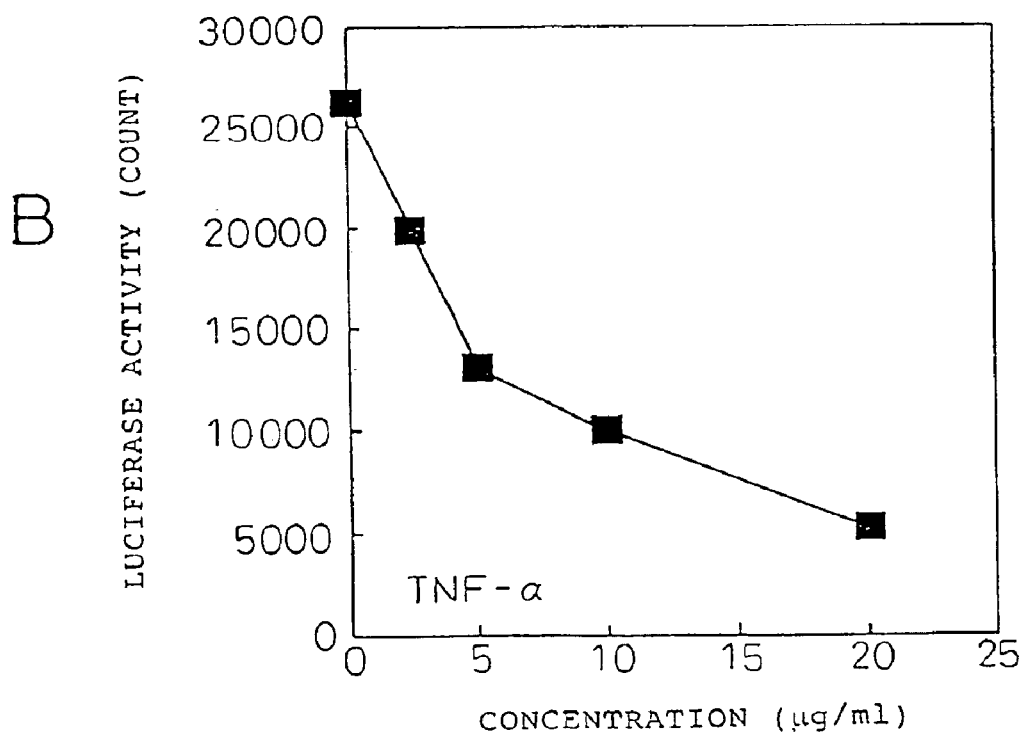

Fig. 4
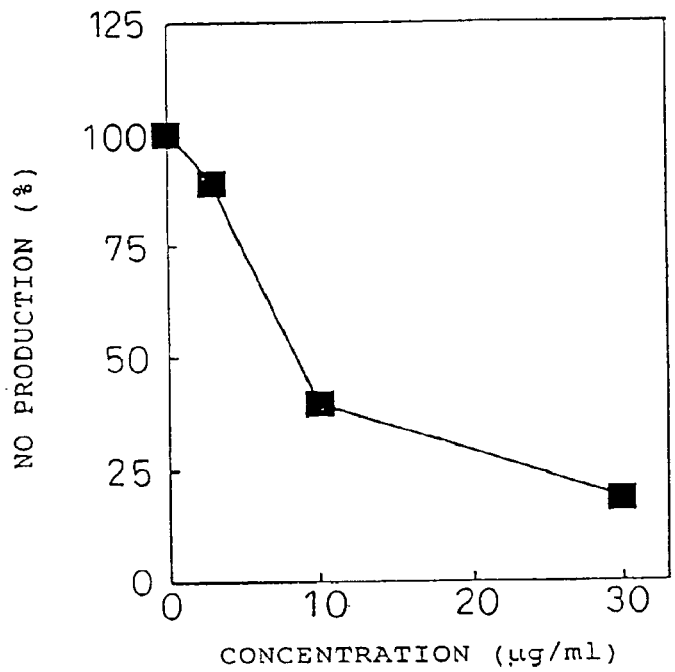
A
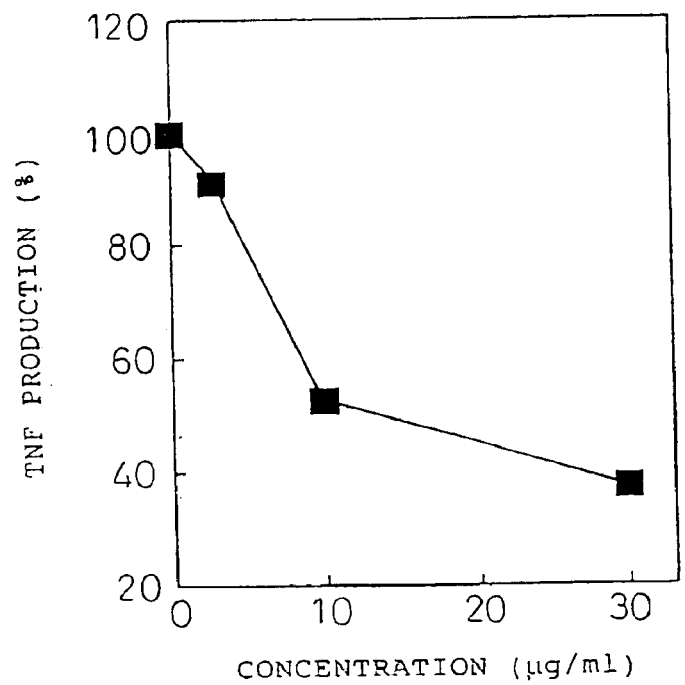
B

NF-κB INHIBITOR COMPRISING PHENYLMETHYL BENZOQUINONE AS THE ACTIVE INGREDIENT

TECHNICAL FIELD

The present invention relates to NF-κB inhibitors, and more specifically to preventive or therapeutic agents for diseases caused by the activation of NF-κB comprising as an active ingredient a benzoquinone derivative or its hydroquinone form or a pharmaceutical acceptable salt thereof.

BACKGROUND ART

Nitric oxide (NO) is biosynthesized from L-arginine as the substrate by NO synthase (NOS). Currently three isozymes of NOS have been found: the brain isozyme (bNOS), the endothelial isozyme (eNOS), and the inducible isozyme (iNOS) (Moncada, S. and Higgs, A. (1993) N. Eng. J. Med. 329: 2002–2012). The transcription of iNOS can be activated by an action of endotoxins and cytokines on macrophage, vascular smooth muscle cells, hepatic cells, chondrocytes, gliacytes, etc., resulting in expression thereof (Forstermann, U., Gath, I., Schwarz, P., Closs, E. I. and Kleinert, H. (1995) Biochem. Pharmacol. 50: 1321–1332).

The iNOS has been reported to be induced by inflammatory conditions regardless of the species, and the suppression of the enzymatic activity and of the expression has been shown to be useful for amelioration of the disease states (Cattell, V. and Jansen, A. (1995) Histochem. J. 27: 777–784; Nussler, A. X. and Billiar, T. R. (1993) J. Leukoc. Biol. 54: 171–178).

It has been reported that arginine derivatives or aminoguanidine exhibit pharmacological effects in model animals of myocarditis, cerebral infarction, arthritis, sepsis, multiple sclerosis, systemic lupus erythematosus, and insulin-dependent diabetes mellitus (Moncada, S. and Higgs, E. A. (1995) Faseb. J. 9: 1319–1330). Though L-N-monomethyl arginine, a NOS inhibitor, is highly toxic at high doses, it not only improves low blood pressure in sepsis but has a marked preventive effect, on which a clinical trial is under way (Moncada, S. and Higgs, E. A. (1995) Faseb. J. 9: 1319–1330).

Furthermore, resistance against sepsis or inflammation induced by carageenin has been shown in experiments using iNOS knockout mice, revealing that the expression of iNOS causes these pathological states (Wei, X. Q., Charles, I. G., Smith, A., Ure, J., Feng, G. J., Huang, F. P., Xu, D., Muller, W., Moncada, S. and Liew, F. Y. (1995) Nature 375: 408–411).

An excess of NO produced by the induction of iNOS expression is believed to damage normal cells and cause various disease states. On the other hand, the constitutively occurring NOS(CNOS) termed eNOS or bNOS is required to suppress an increase in blood pressure and to maintain it. Thus, inhibitors which do not inhibit the activity of cNOS and that are specific for iNOS are required. However, since the regions of the proteins that regulates the enzymatic activity of isozymes are very similar to one another in the primary structure, no NOS inhibitors have yet been found which are sufficiently specific (Ogden, J. E. and Moore, P. K. (1995) Trends Biotechnol. 13: 70–78, Manning, R., Jr., Hu. L., Mizelle, H. L., Montani, J. P. and Norton, M. W. (1993) Hypertension 22: 40–48).

As enzyme inhibitors, L-arginine (and amino acid) derivatives have mainly been developed but many of them are low in isozyme specificity. Although aminoguanidine and amidine derivaties, though weakly effective, have been reported to have relatively iNOS-specific inhibitory effects (Southan, G. J. and Szabo, C. (1996) Biochem. Pharmacol. 51: 383–394), pharmaceutical agents having adequate specificity have yet not to be found.

On the other hand, TNF-α, a cytokine produced by various cells including macrophage, is believed to be an important mediator of inflammation (Vassalli, P. (1992) Annu. Rev. Immunol. 10: 411–452). There is growing evidence that the excessive production of TNF-α damages normal cells and causes various pathological conditions (Muto, Y., Nouri-Aria, K. T., Meager, A., Alexander, G. J., Eddleston, A. L. and Williams, R. (1988) Lancet 2: 72–74, Sharief, M. K. and Hentges, R. (1991) N. Engl. J. Med. 325: 467–472).

Increases in TNF-α have been observed in the synovial fluid and the blood of patients with, for example, rheumatoid arthritis (Tetta, C., Camussi, G., Modena, V., Di Vittorio, C. and Baglioni, C. (1990) Ann. Rheum. Dis. 49: 665–667; Venn, G., Nietfeld, J. J., Duits, A. J., Brennan, F. M., Arner, E., Covington, M., Billingham, M. E. and Hardingham, T. E. (1993) Arthritis Rheum. 36: 819–826). Antibody against TNF-α has also been demonstrated to be effective in clinical trials (Elliott, M. J., Maini, R. N., Feldmann, M., Long-Fox, A., Charles, P., Bijl, H. and Woody, J. N. (1994) Lancet 344:1125–1127; Elliott, M. J., Maini, R. N., Feldmann, M., Kalden. J. R., Antoni, C., Smolen, J. S., Leeb, B., Breedveld, F. C., Macfarlane, J. D., Bijl, H. and et al. (1994) Lancet 344:1105–1110; Rankin, E. C., Choy, E. H., Kassimos, D., Kingsley, G. H., Sopwith, A. M., Isenberg, D. A. and Panayi, G. S. (1995) Br. J. Rheumatol. 34: 334–342).

Furthermore, the involvement of TNF-α in sepsis or inflammatory bowel diseases has been pointed out and the ameliorating effects of anti-TNF-α antibody on these diseases have been observed (Vincent, J. L., Bakker, J., Marecaux, G., Schandene, L., Kahn, R. J. and Dupont, E. (1992) Chest 101: 810–815; Hinshaw, L. B., Tekamp-Olson, P., Chang, A. C., Lee, P. A., Taylor, F., Jr., Murray, C. K., Peer, G. T., Emerson, T., Jr., Passey, R. B. and Kuo, G. C. (1990) Circ. Shock 30: 279–292).

These findings expressly indicate that the excessive production of TNF-α causes and aggravates various inflammations, and thereby there the development of pharmaceutical agents which can inhibit the production of TNF-α is required (Nyman, U., Mussener, A., Larsson, E., Lorentzen, J. and Klareskog, L. (1997) Clin. Exp. Immunol. 108: 415–419).

Thus, iNOS or TNF-α have been recognized to be one of the causes of various inflammations. However, the fact that many other mediators have been demonstrated to cause inflammation and thereby the cause of the diseases cannot be attributed to any one particular mediator makes the development of therapeutic agents difficult. Under these circumstances, there is a great need for low molecular weight compounds that not only suppress the expression of particular proteins but inhibit widely the production and expression of proteins involved as causative factor in the inflammation.

NF-κB is a protein that regulates gene expression and is one of the so-called transcription factors. When normal cells are stimulated with an inflammatory cytokine such as interleukin-1 (IL-1) and TNF-α, a lipopolysaccharide, or ultraviolet rays, NF-κB are activated and then they translocate from the cytoplasm into the nucleus where they bind to specific nucleotide sequences on the genomic DNA and thereby become involved in the expression of various genes (Blackwell, T. S. and Christman, J. W. (1997) Am. J. Respir. Cell Mol. Biol. 17: 3–9).

Genes encoding iNOS and TNF-α, though entirely different from one another, have regions to which NF-κB binds on the expression control region of the genomic gene thereof, and there is growing evidence that the activation of NF-κB is important for the expression of these proteins in common (Jongeneel, C. V. (1994) Prog. Clin. Biol. Res. 388: 367–381; Xie, Q. W., Kashiwabara, Y. and Nathan, C. (1994) J. Biol. Chem. 269: 4705–4708; Nunokawa, Y., Oikawa, S. and Tanaka, S. (1996) Biochem. Biophys. Res. Commun. 223: 347–352).

Many genes that are involved in immunological inflammatory reactions under expression control by NF-κB are recognized, in addition to iNOS and TNF-α, ones for inflammatory cytokines such as IL-1, IL-6 and IL-8, as well as cell adhesion factors such as ICAM-1, VCAM-1 and ELAM-1 or the like (Collins, T., Read, M. A., Neish, A. S., Whitley, M. Z., Thanos, D. and Maniatis, T. (1995) Faseb. J. 9: 899–909). Furthermore, it is known that inflammatory cytokines, when bound to receptors, transduce NF-κB-activating signals via various routes, and this fact is believed to be cause that further aggravates inflammation. Thus, the activation of NF-κB in inflammation is understood as an etiological and aggravating matter of diseases (Baeuerle, P. A. and Baichwal., V. R. (1997) Adv. Immunol. 65: 111–137).

In recent years, it has also been reported that HIV, HTLV-1, CMV, adenovirus and the like activate NF-κB in host cells (Dezube, B. J., Pardee, A. B., Beckett, L. A., Ahlers, C. M., Ecto, L., Allen-Ryan, J., Anisowicz, A., Sager, R. and Crumpacker, C. S. (1992) J. Acquir. Immune Defic. Syndr. 5: 1099–1104; Nabel, G. and Baltimore, D. (1987) Nature 326: 711–713; Fazely, F., Dezube, B. J., Allen-Ryan, J., Pardee, A. B. and Ruprecht, R. M. (1991) Blood 77: 1653–1656; Munoz, E. and Israel, A. (1995) Immunobiology 193: 128–136). The activation of NF-κB in turn activates its transcription leading to the progression of viral propagation and infection.

Accordingly, it is possible to suppress altogether the induction of expression of these inflammatory cytokines, genes of adhesion molecules, and viruses by inhibiting the activation of NF-κB, and NF-κB inhibitors are promising as therapeutic agents of such diseases as are caused either directly or indirectly by the activation of NF-κB, specifically various inflammatory diseases, autoimmune diseases and viral diseases, and immunosuppressive agents.

Therapeutic agents currently used for chronic diseases include steroid hormones such as glucocorticoids, non-steroidal aspirin formulations, and the like. However, glucocorticoids are known to be associated with the appearance of severe side effects such as the aggravation of infectious diseases, onset of peptic ulcer, and central effects, and therefore are not amenable to a long-term administration. Furthermore, although the non-steroidal agents, suppress the production of prostaglandins etc., they do not provide curative treatments and they are known to exhibit such side effects as the onset of peptic ulcer and central effects.

It has also been reported in recent years that anti-inflammatory drugs at high doses inhibit the activation of NF-κB (Auphan, N., DiDonato, J. A., Rosette, C., Helmberg, A. and Karin, M. (1995) Science 270: 286–290; Shackelford, R. E., Alford, P. B., Xue, Y., Thai, S. F., Adams, D. O. and Pizzo, S. (1997) Mol Pharmacol. 52: 421–429; Bitko, V., Velazquez, A., Yang, L., Yang, Y. C. and Barik, S. (1997) Virology 232: 369–378). However, due to their diverse pharmacological actions, these compounds have side effects, and therefore the development of safer drugs based on a novel mechanism is required.

As a method of inhibiting the actions of TNF-α, it is thought that the use of antibodies that specifically bind to TNF-α and TNF receptor proteins. However, those are both macromolecule proteins and are not suitable for oral administration.

Phenylmethyl benzoquinone derivatives exhibit the effect of improving cerebral functions in experimental animals of anoxia at low doses, and are shown to be effective for improving and treating intracerebral organic disorders and mental function disorders (Suzuki, K., Tatsuoka, T., Murakami, T., Ishihara, T., Aisaka, K., Inoue, T., Ogino, R., Kuroki, M., Miyazaki, T., Satoh, F., Miyano, S. and Sumoto, K. (1996) Chem. Pharm. Bull. 44: 139–144). However, at present the effects of phenylmethyl benzoquinone derivatives on the production of inflammatory mediators and on the activation of NF-κB have not been known.

DISCLOSURE OF THE INVENTION

The present invention provides preventive and therapeutic agents for diseases caused by the activation of NF-κB, for example, diseases caused by the overproduction of various inflammatory mediators and viral propagation, by suppressing and/or inhibiting the activation of NF-κB. More specifically it provides therapeutic and preventive agents for diseases that are believed to be caused by the excessive production of NO or TNF-α including, for example, septic shock, osteoarthritis, rheumatoid arthritis, cachexia, multiple organ failure, inflammatory bowel diseases, malaria, acquired immune deficiency syndrome, human T-cell leukemia, meningitis, hepatitis, type II diabetes, multiple sclerosis, Behcet disease, systemic lupus erythematosus, ischemic heart disease, Alzheimer's disease, and the like.

As a result of intensive studies on substances that inhibit the activation of NF-κB, the present inventors have found that benzoquinone derivatives represented by the general formula (1) or its hydroquinone forms or pharmaceutical acceptable salts thereof potently suppress and/or inhibit the activation of NF-κB and that they inhibit the production of NO and TNF-α on the gene level, and thereby have accomplished the present invention.

Thus, the present invention relates to NF-κB inhibitors comprising as an active ingredient a benzoquinone derivative represented by the following general formula (1):

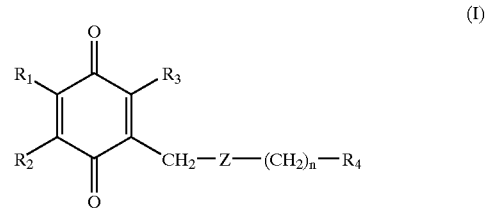

(I)

wherein $R_1$, $R_2$, and $R_3$ are each independently a hydrogen atom, an alkyl group having 1 to 5 carbons, or an alkoxy group having 1 to 5 carbons;

$R_4$ is a hydrogen atom, a hydroxymethyl group, an alkyl group, or a carboxyl group which is optionally esterified or amidated;

Z is

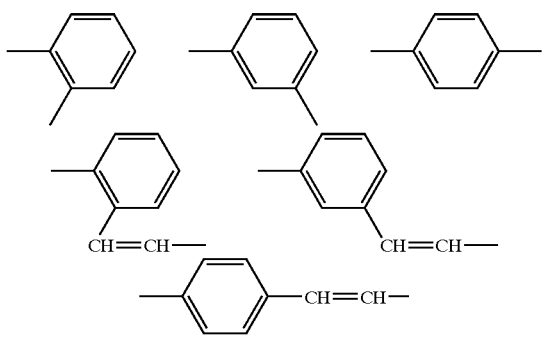

and, n is an integer from 0 to 6, or its hydroquinone form, or a pharmaceutically acceptable salts thereof, and to their use in the preventive or therapeutic agents for inflammatory diseases, autoimmune diseases, and viral diseases, in which they are used as suppressing agents for the gene expression of one or more substances selected from the group consisting of IL-1, TNF-α, IL-2, IL-6, IL-8, iNOS, granulocyte colony-stimulating factor, interferon-β, ICAM-1, VCAM-1, ELAM-1, major histocompatibility system class I, major histocompatibility system class II, β2-microglobulin, immunoglobulin light chain, serum amyloid A, angiotensinogen, complement B, complement C4, c-myc, HIV, HTLV-1, SV40, CMV, and adenovirus.

The present invention also provides preventive or therapeutic agents for diseases caused by the activation of NF-κB comprising as an active ingredient a benzoquinone derivative represented by the general formula (1) or its hydroquinone form or a pharmaceutical acceptable salt thereof.

The present invention also relates to inhibitors of TNF-α production comprising as an active ingredient a benzoquinone derivative represented by the general formula (1) or its hydroquinone form or a pharmaceutical acceptable salt thereof, and to their use as the preventive or therapeutic agents for inflammatory diseases, autoimmune diseases, and viral diseases, in which they are used as suppressing agents for the gene expression of one or more substances selected from the group consisting of IL-1, TNF-α, IL-2, IL-6, IL-8, iNOS, granulocyte colony-stimulating factor, interferon-β, ICAM-1, VCAM-1, ELAM-1, plasminogen activator-inhibiting factor I, major histocompatibility system class I, major histocompatibility system class II, β2-microglobulin, immunoglobulin light chain, serum amyloid A, angiotensinogen, complement B, complement C4, c-myc, HIV, HTLV-1, SV40, CMV, and adenovirus.

The present invention also provides preventive or therapeutic agents for diseases caused by the overproduction of TNF-α comprising as an active ingredient a benzoquinone derivative represented by the general formula (1) or its hydroquinone form or a pharmaceutical acceptable salt thereof.

The present invention also provides a benzoquinone derivative represented by the general formula (1) or its hydroquinone form or a pharmaceutical acceptable salt thereof.

L represents a complex of a labeled probe comprising an NF-κB binding sequence and the nuclear extract, and F shows a result of the experiment in which a non-labeled probe was added at an amount 100 times more than that of the labeled probe under the same condition as that of L.

FIG. 3 shows the effect of the compound obtained in Example 4 when A549/NF-κB Luc is stimulated with IL-1 or TNF-α. It shows the result of the experiment in which the compound obtained in Example 4 was added, and one hour later it was stimulated for 4 hours with IL-1 or TNF-α followed by the determination of the activity of the reporter gene.

FIG. 4 shows the effect of the compound obtained in Example 4 on the production of NO and TNF-α after stimulation with LPS using the mouse macrophage-derived RAW 264.7.

It shows the result of the experiment in which the compound obtained in Example 4 was added to the culture medium one hour before LPS stimulation and then the NO level (A) in the culture medium 24 hours after the stimulation and the TNF-α level (B) in the culture medium 4 hours after the stimulation were determined.

Figure 5:
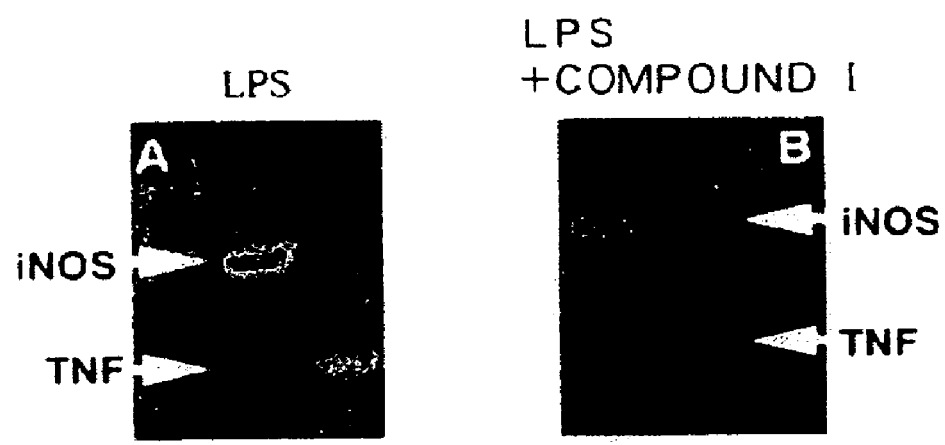

FIG. 5 shows changes in the amount of mRNA of iNOS and TNF-α in the RAW264.7 cells.

A shows the result obtained by the determination of the level of iNOS mRNA and TNF-α mRNA in the cells 6 hours after the LPS stimulation.

B shows the result of the experiment in which the compound (20 μg/ml) obtained in Example 4 was added to the culture medium one hour before the LPS stimulation and then the levels of iNOS mRNA and TNF-α mRNA in the cells 6 hours after the stimulation were measured.

Figure 6:
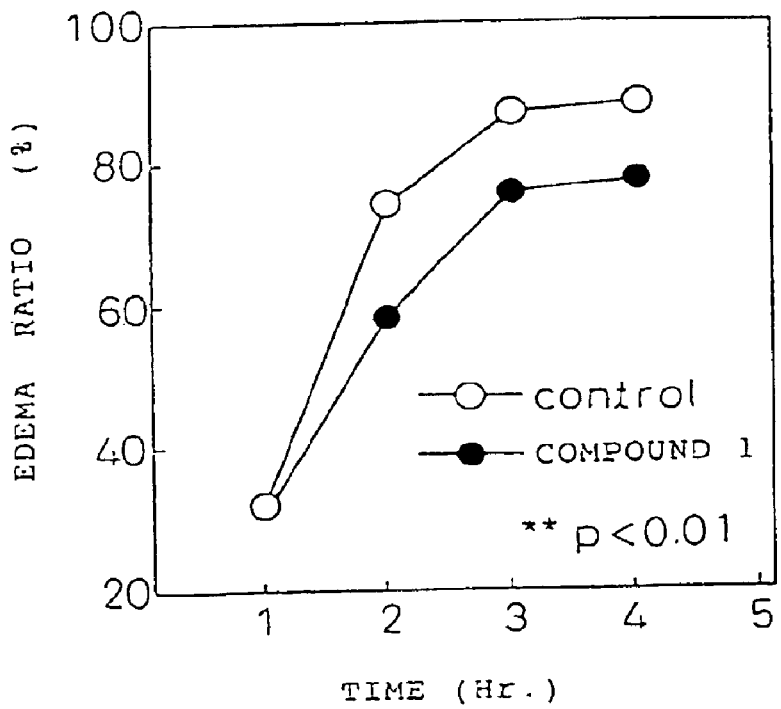

FIG. 6 shows changes with time of the incidence of edema after the administration of a prophlogistic agent when compound 1 (30 mg/kg) was intraperitoneally given 2 hours before the administration of the prophlogistic agent.

Figure 7:
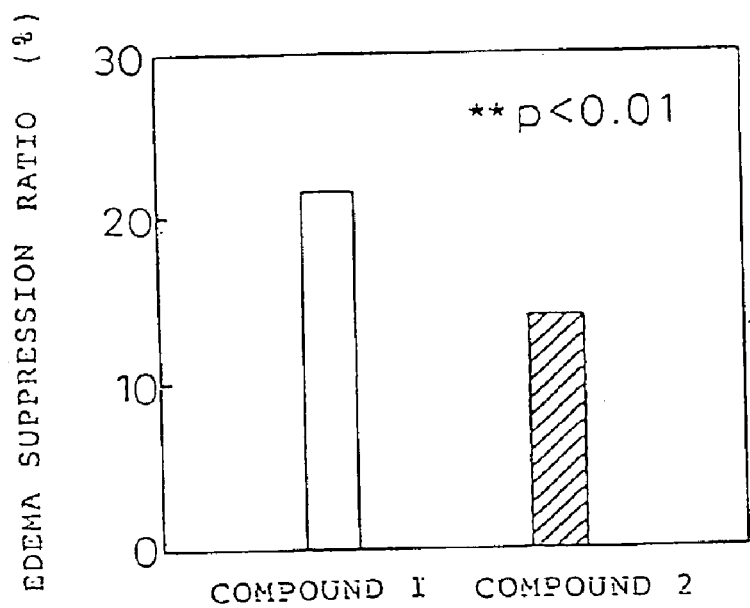

FIG. 7 shows the incidence of edema suppression 2 hours after the administration of a prophlogistic agent when compound 1 (30 mg/kg) and compound 2 (50 mg/kg) were intraperitoneally given 2 hours before the administration of the prophlogistic agent.

EMBODIMENT FOR CARRYING OUT THE INVENTION

The hydroquinone form as used herein refers to the compound that is formed by converting an oxo at position 1 and/or position 4 of the benzoquinone ring of the benzoquinone derivative of the present invention to a hydroxy group chemically with a catalyst etc. or biochemically with an enzyme etc., or by converting with reduction in vivo, and that has an activity equivalent to that of the benzoquinone derivative.

As the pharmaceutically acceptable salt, there may be mentioned, for example, a salt with an inorganic acid such as hydrochloric acid, nitric acid, sulfuric acid, phosphoric acid, and hydrobromic acid, an organic acid such as maleic acid, fumaric acid, tartaric acid, lactic acid, citric acid, acetic acid, methanesulfonic acid, p-toluenesulfonic acid, adipic acid, palmitic acid, and tannic acid, an inorganic metal including an alkali metal such as lithium, sodium, and potassium, and an alkaline earth metal such as calcium, and magnesium, and a basic amino acid such as lysine, or a salt with an organic amine such as ammonium.

In the formula, $R_1$, $R_2$, and $R_3$ are each independently a hydrogen atom, an alkyl group having 1 to 5 carbons, or an alkoxy group having 1 to 5 carbons. Preferred examples of the alkyl group include straight or branched saturated aliphatic hydrocarbon groups having 1 to 5 carbons such as methyl, ethyl, propyl, isopropyl, butyl, isobutyl, sec-butyl, tert-butyl, pentyl, isopentyl, neopentyl, and tert-pentyl, saturated alicyclic hydrocarbon groups such as cyclopropyl, cyclobutyl, cyclopentyl, and cyclohexyl, saturated alicyclic hydrocarbon-aliphatic hydrocarbon groups such as cyclopropylmethyl, cyclopropylethyl, and cyclobutylmethyl, and the alkoxy groups include the oxy groups of the above. Preferred examples of $R_1$ and $R_2$ include a hydrogen atom, a methyl group, and a methoxy group, and those of $R_3$ include a hydrogen atom or a methyl group.

$R_4$ represents a hydrogen atom, a hydroxymethyl group, an alkyl group, or a carboxyl group which is optionally esterified or amidated, wherein preferred examples of the alkyl group include those mentioned above for $R_1$, $R_2$ and $R_3$, and preferred examples of the carboxyl group which is optionally esterified or amidated include: a group —$COOR_5$ wherein $R_5$ is a hydrogen atom, an optionally substituted alkyl group having 1 to 8 carbons, an optionally substituted phenyl group, or an optionally substituted aralkyl group having 7 to 1H carbons; a group —$CONR_6R_7$ wherein $R_6$ and $R_7$ are each independently a hydrogen atom, an optionally substituted alkyl group having 1 to 8 carbons, an optionally substituted bicyclic unsaturated or partially saturated hydrocarbon ring group having 9 to 1H carbons, an optionally substituted heterocyclic group, an optionally substituted phenyl group, an optionally substituted aralkyl group having 7 to 10 carbons, or a heteroaryl-$C_1$–$C_3$-alkyl group, or $R_6$ and $R_7$, together with the nitrogen atom to which they are attached, represent a heterocyclic group which may further contain a nitrogen, oxygen, and/or sulfur atom, and; a group —$CONR_6R_7$ wherein $R_6$ and $R_7$, together with the nitrogen atom to which they are attached, represent a 5- to 10-membered optionally substituted, nitrogen-containing heterocyclic group which may contain, in addition to the carbon and nitrogen atom, 1 to 3 heteroatoms selected from the group consisting of a nitrogen, oxygen, and sulfur atom, the carbon atom on said cyclic group being optionally a ketone form or the sulfur atom on said cyclic group being optionally an oxide form.

As specific examples of the alkyl group $R_5$ having 1 to 8 carbons, there may be mentioned a straight or branched saturated aliphatic hydrocarbon group having 1 to 8 carbons such as methyl, ethyl, propyl, isopropyl, butyl, isobutyl, sec-butyl, tert-butyl, 3-methylbutyl, pentyl, 1-ethylbutyl, isopentyl, neopentyl, tert-pentyl, 1,3-dimethylbutylhexyl, 1-methylhexyl, 3,3-dimethylbutyl, 2-ethylbutyl, 2-methylpentyl, 3-methylpentyl, hexyl, heptyl, and 1-methylheptyl; a saturated alicyclic hydrocarbon group such as cyclopropyl, cyclobutyl, cyclopentyl, cyclohexyl, cycloheptyl, and cyclooctyl; and a saturated alicyclic hydrocarbon-aliphatic hydrocarbon group such as cyclopropylmethyl, cyclopropylethyl, cyclobutylmethyl, cyclopentylmethyl, cyclohexylmethyl, and cyclopentylmethyl, and the like. AS specific examples of an aralkyl group having 7 to 11 carbons, there may be mentioned benzyl, phenethyl, 1-phenylethyl, 3-phenylpropyl, 4-phenylbutyl, 5-phenylpentyl, 1-naphthylmethyl, 2-naphthylmethyl and the like.

The alkyl, phenyl and aralkyl groups described above may be substituted, on the chain or the ring thereof, with one or two substituents or substituents comprising combinations of these substituents, said substituent being selected from, for example, a hydroxyl group; an aldehyde group; a carboxyl group; a carbamoyl group; an amino group; a nitrile group; a cyano group; a halogen atom such as a chlorine and fluorine atom; an alkyl group having preferably 1 to 6 carbons such as a methyl, ethyl, propyl and isopropyl group, or their halogenated or hydroxy-substituted group and alkoxy-alkyl group; an aryl group having preferably 6 to 10 carbons such as a phenyl and naphthyl group, or their halogenated group; an aralkyl group having preferably 7 to 11 carbons such as a benzyl, phenethyl and 3-phenylpropyl group; an alkyloxy group having preferably 1 to 6 carbons such as a methoxy, ethoxy, propyloxy and butyloxy group; a cyclic acetal group such as a methylenedioxy and ethylenedioxy group; an aralkyloxy having preferably 7 to 11 carbons such as a benzyloxy, phenethyloxy and 3-phenylpropyloxy group, and phenoxy group; an alkylcarbonyl group having preferably 2 to 6 carbons such as a methylcarbonyl, ethylcarbonyl and propylcarbonyl group; an arylcarbonyl group having preferably 7 to 11 carbons such as a benzoyl group; an alkyloxycarbonyl group having preferably 2 to 6 carbons such as a methoxycarbonyl, ethoxycarbonyl, propyloxycarbonyl and tert-butyloxycarbonyl group; an aralkyloxycarbonyl having preferably 8 to 12 carbons such as a benzyloxycarbonyl, phenethyloxycarbonyl and 3-phenylpropyloxycarbonyl group, and phenoxycarbonyl group; an amino group substituted with one substituent or a combination of two substituents that are the same or different, said substituent being selected from an alkyl group having preferably 1 to 4 carbons such as a methyl, ethyl, propyl and isopropyl group, an aralkyl having preferably 7 to 11 carbons such as a benzyl, phenethyl and 3-phenylpropyl group, phenyl group, an alkylcarbonyl group having preferably 2 to 6 carbons such as a methylcarbonyl, ethylcarbonyl and propylcarbonyl group, and an arylcarbonyl group having preferably 7 to 11 carbons such as a benzoyl group and the like; a 5- to 10-membered monocyclic or bicyclic unsaturated, partially or fully saturated heterocyclic ring containing 1 to 3 heteroatoms selected from the group consisting of a nitrogen, oxygen and sulfur atom, for example, pyrrole, furan, thiophene, pyran, indole, benzofuran, benzothiophene, benzopyran, pyrazole, isoxazole, isothiazole, indazole, benzoisoxazole, benzoisothiazole, imidazole, oxazole, thiazole, benzimidazole, benzoxazole, benzothiazole, pyridine, quinoline, isoquinoline, pyridazine, pyrimidine, pyrazine, cinnoline, phthalazine, quinazoline, quinoxaline, and a partially or fully saturated ring group thereof; a carbamoyl group having an amino group substituted with one substituent or a combination of two substituents that are the same or different, said substituent being selected from an alkyl group having preferably 1 to 4 carbons such as a methyl, ethyl, propyl and isopropyl group, an aralkyl having preferably 7 to 11 carbons such as a benzyl, phenethyl and 3-phenylpropyl group, phenyl group, an alkylcarbonyl group having preferably 2 to 6 carbons such as a methylcarbonyl, ethylcarbonyl and propylcarbonyl group, and an arylcarbonyl group having preferably 7 to 11 carbons such as a benzoyl group, and the like, or a cyclic amino group such as a 5- to 8-membered heterocyclic ring optionally containing 1 to 3 heteroatoms selected from the group consisting of a nitrogen, oxygen and sulfur atom, for example, pyrrolidine, piperidine, morpholine, thiomorpholine, and piperazine; and the like.

As the optionally substituted alkyl groups having 1 to 8 carbons, the optionally substituted phenyl group and the optionally substituted aralkyl group having 7 to 11 carbons of $R_6$ and $R_7$, those described for $R_5$ may be mentioned. As specific examples of the hydrocarbon ring of a bicyclic unsaturated or partially saturated hydrocarbon ring group having 9 to 11 carbons, there may be mentioned indene, indan, naphthalene, 1,2-dihydronaphthalene, 1,2,3,4-tetrahydronaphthalene and the like. As specific examples of the heterocyclic ring of a heterocyclic group, there may be mentioned a 5- to 10-membered monocyclic or bicyclic unsaturated, or partially or fully saturated heterocyclic ring containing 1 to 3 heteroatoms selected from the group consisting of a nitrogen, oxygen and sulfur atom, for example, pyrrole, furan, thiophene, pyran, indole, benzofuran, benzothiophene, benzopyran, pyrazole, isoxazole, isothiazole, indazole, benzoisoxazole, benzoisothiazole, imidazole, oxazole, thiazole, benzimidazole, benzoxazole, benzothiazole, pyridine, quinoline, isoquinoline, pyridazine, pyrimidine, pyrazine, cinnoline, phthalazine, quinazoline, quinoxaline, 1,2,3,4-tetrahydroquinoline, 1,2,3,4-tetrahydroisoquinoline, decahydroquinoline, and the like, as well as the partially or fully saturated ring thereof. Examples of a heteroaryl-$C_1$–$C_3$-alkyl group include, for example, a 2-pyridylmethyl, 3-pyridylmethyl, 4-pyridylmethyl, 2-pyrimidylmethyl, 2-imidazolylmethyl, 2-pyridylethyl, 3-pyridylethyl, 4-pyridylethyl, 1-(2-pyridyl)ethyl, 1-(3-pyridyl)ethyl, and 1-(4-pyridyl)ethyl group, and they may also be substituted on the chain or ring thereof with the same substituent to those described above for $R_5$.

As preferred examples of the heterocyclic group formed by $R_6$ and $R_7$ together with the nitrogen atom to which they are attached, which may further contain a nitrogen, oxygen and/or sulfur atom, or the 5- to 10-membered nitrogen-containing heterocyclic group formed by $R_6$ and $R_7$ together with the nitrogen atom to which they are attached, which may contain, in addition to a carbon and nitrogen atom, 1 to 3 heteroatoms selected from the group consisting of a nitrogen, oxygen and sulfur atom, there may be mentioned, for example, morpholino, thiomorpholino, pyrrolidino, piperidino, homopiperidino, piperazino, homopiperazino, and the like.

The carbon atom on the chain or the ring may be a ketone form, or the sulfur atom may be an oxide form, or the carbon atom or the nitrogen atom on the chain or the ring may be substituted with substituents as described for $R_5$.

Z is represented by

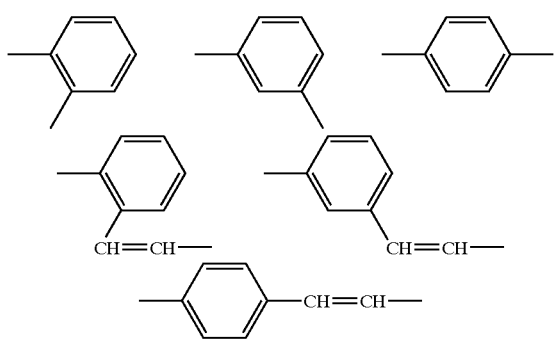

n represents an integer from 0 to 6. In a preferred example, Z is

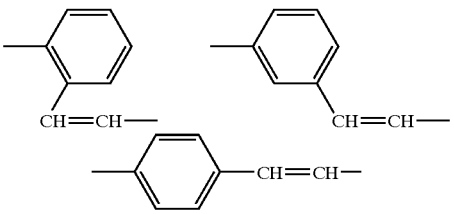

and n is an integer 0, or Z is

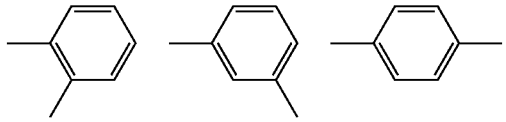

and n is a integer 1, 2 or 3.

Most preferably, $R_1$ and $R_2$ are a methyl group or methoxy group; $R_3$ is a methyl group; $R_4$ is a carboxyl group which is optionally esterified or amidated; Z is

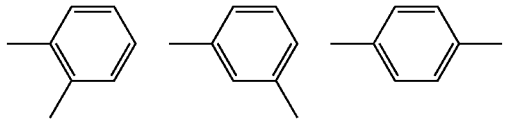

and n is an integer 1, 2 or 3.

Preferred specific compounds include the following compounds:
N-[3-[4-(5,6-dimethoxy-3-methyl-1,4-benzoquinon-2-ylmethyl)phenyl]propionyl]morpholine,
N-[3-[4-(5,6-dimethoxy-3-methyl-1,4-benzoquinon-2-ylmethyl)phenyl]propionyl]thiomorpholine,
N-[3-[(4-(5,6-dimethoxy-3-methyl-1,4-benzoquinon-2-ylmethyl)phenyl]propionyl]thiomorpholine S-oxide,
N-[3-[4-(5,6-dimethoxy-3-methyl-1,4-benzoquinon-2-ylmethyl)phenyl]propionyl]thiomorpholine S-dioxide,
N-[3-[4-(5,6-dimethoxy-3-methyl-1,4-benzoquinon-2-ylmethyl)phenyl]propionyl]piperidine,
N-[3-[4-(5,6-dimethoxy-3-methyl-1,4-benzoquinon-2-ylmethyl)phenyl]propionyl]dimethylamine,
N-[3-[4-(5,6-dimethoxy-3-methyl-1,4-benzoquinon-2-ylmethyl)phenyl]propionyl]isopropylamine,
N-[3-[4-(5,6-dimethoxy-3-methyl-1,4-benzoquinon-2-ylmethyl)phenyl]propionyl]ethanolamine,
N-[3-[4-(5,6-dimethoxy-3-methyl-1,4-benzoquinon-2-ylmethyl)phenyl]propionyl]benzylamine,
N-[3-[4-(5,6-dimethoxy-3-methyl-1,4-benzoquinon-2-ylmethyl)phenyl]propionyl]phenethylamine,
N-[3-[4-(5,6-dimethoxy-3-methyl-1,4-benzoquinon-2-ylmethyl)phenyl]acryloyl]morpholine,
N-[3-[4-(5,6-dimethoxy-3-methyl-1,4-benzoquinon-2-ylmethyl)phenyl]acryloyl]thiomorpholine,
N-[3-[4-(5,6-dimethoxy-3-methyl-1,4-benzoquinon-2-ylmethyl)phenyl]acryloyl]piperidine,
N-[3-[4-(5,6-dimethoxy-3-methyl-1,4-benzoquinon-2-ylmethyl)phenyl]acryloyl]dimethylamine,
N-[3-[4-(5,6-dimethoxy-3-methyl-1,4-benzoquinon-2-ylmethyl)phenyl]acryloyl]isopropylamine,
N-[3-[4-(5,6-dimethoxy-3-methyl-1,4-benzoquinon-2-ylmethyl)phenyl]acryloyl]ethanolamine,
N-[3-[4-(5,6-dimethoxy-3-methyl-1,4-benzoquinon-2-ylmethyl)phenyl]acryloyl]benzylamine,
N-[3-[4-(5,6-dimethoxy-3-methyl-1,4-benzoquinon-2-ylmethyl)phenyl]acryloyl]phenethylamine, 3-[4-(5,6-dimethoxy-3-methyl-1,4-benzoquinon-2-ylmethyl)phenyl]propionic acid,
3-[4-(5,6-dimethoxy-3-methyl-1,4-benzoquinon-2-ylmethyl)phenyl]acrylic acid,
2,3-dimethoxy-6-benzyl-5-methyl-1,4-benzoquinone,
3-[(4-(5,6-dimethoxy-3-methyl-1,4-benzoquinon-2-ylmethyl)phenyl]propanol,
3-[3-(5,6-dimethoxy-3-methyl-1,4-benzoquinon-2-ylmethyl)phenyl]propionic acid ethylester,
3-[3-(3,5,6-trimethyl-1,4-benzoquinon-2-ylmethyl)phenyl]acrylic acid,
3-[3-(3,5,6-trimethyl-1,4-benzoquinon-2-ylmethyl)phenyl]propionic acid,
3-[3-(3,5,6-trimethyl-1,4-benzoquinon-2-ylmethyl)phenyl]propionic acid ethylester,
N-[3-[3-(3,5,6-trimethyl-1,4-benzoquinon-2-ylmethyl)phenyl]propionyl]morpholine,
1-[3-[3-(3,5,6-trimethyl-1,4-benzoquinon-2-ylmethyl)phenyl]propionyl]-4-methylpiperazine,
4-[3-(3,5,6-trimethyl-1,4-benzoquinon-2-ylmethyl)phenyl]-n-butyric acid,
3-[3-(5,6-dimethoxy-3-methyl-1,4-benzoquinon-2-ylmethyl)phenyl]propionic acid,
3-[4-(3,5,6-trimethyl-1,4-benzoquinon-2-ylmethyl)phenyl]acrylic acid,
3-[4-(3,5,6-trimethyl-1,4-benzoquinon-2-ylmethyl)phenyl]acrylic acid ethylester,
3-[4-(3,5,6-trimethyl-1,4-benzoquinon-2-ylmethyl)phenyl]propionic acid,
4-[(4-(3,5,6-trimethyl-1,4-benzoquinon-2-ylmethyl)phenyl]-n-butyric acid,
N-[3-[3-(5,6-dimethoxy-3-methyl-1,4-benzoquinon-2-ylmethyl)phenyl]propionyl]piperidine,
N-[3-[3-(5,6-dimethoxy-3-methyl-1,4-benzoquinon-2-ylmethyl)phenyl]propionyl]thiomorpholine,
N-[3-[3-(5,6-dimethoxy-3-methyl-1,4-benzoquinon-2-ylmethyl)phenyl]propionyl]morpholine,
N-[3-[3-(5,6-dimethoxy-3-methyl-1,4-benzoquinon-2-ylmethyl)phenyl]propionyl]isopropylamine,
3-[3-(5,6-dimethoxy-3-methyl-1,4-benzoquinon-2-ylmethyl)phenyl]acrylic acid,
N-[3-[3-(5,6-dimethoxy-3-methyl-1,4-benzoquinon-2-ylmethyl)phenyl]acryloyl]piperidine,
N-[3-[3-(5,6-dimethoxy-3-methyl-1,4-benzoquinon-2-ylmethyl)phenyl]acryloyl]morpholine,
N-[3-[3-(5,6-dimethoxy-3-methyl-1,4-benzoquinon-2-ylmethyl)phenyl]acryloyl]isopropylamine,
N-[3-[3-(5,6-dimethoxy-3-methyl-1,4-benzoquinon-2-ylmethyl)phenyl]acryloyl]thiomorpholine,
N-[3-[4-(3,5,6-trimethyl-1,4-benzoquinon-2-ylmethyl)phenyl]propionyl]isopropylamine,
N-[3-[4-(3,5,6-trimethyl-1,4-benzoquinon-2-ylmethyl)phenyl]propionyl]piperidine,
N-[3-[4-(3,5,6-trimethyl-1,4-benzoquinon-2-ylmethyl)phenyl]propionyl]morpholine,
N-[3-[3-(3,5,6-trimethyl-1,4-benzoquinon-2-ylmethyl)phenyl]propionyl]isopropylamine,
N-[3-[3-(3,5,6-trimethyl-1,4-benzoquinon-2-ylmethyl)phenyl]propionyl]piperidine,
3-[2-(5,6-dimethoxy-3-methyl-1,4-benzoquinon-2-ylmethyl)phenyl]acrylic acid,
N-[3-[2-(5,6-dimethoxy-3-methyl-1,4-benzoquinon-2-ylmethyl)phenyl]acryloyl]thiomorpholine,
3-[2-(5,6-dimethoxy-3-methyl-1,4-benzoquinon-2-ylmethyl)phenyl]propionic acid,
N-[3-[2-(5,6-dimethoxy-3-methyl-1,4-benzoquinon-2-ylmethyl)phenyl]propionyl]piperidine,
N-[3-[2-(5,6-dimethoxy-3-methyl-1,4-benzoquinon-2-ylmethyl)phenyl]propionyl]morpholine,
N-[3-[(2-(5,6-dimethoxy-3-methyl-1,4-benzoquinon-2-ylmethyl)phenyl]propionyl]thiomorpholine,
N-[3-[2-(5,6-dimethoxy-3-methyl-1,4-benzoquinon-2-ylmethyl)phenyl]propionyl]isopropylamine,
N-[3-[4-(5,6-dimethoxy-3-methyl-1,4-benzoquinon-2-ylmethyl)phenyl]propionyl]-(s)-2-(methoxymethyl)pyrrolidine,
N-[3-[4-(5,6-dimethoxy-3-methyl-1,4-benzoquinon-2-ylmethyl)phenyl]propionyl]isonipecotamide,
N-[3-[4-(5,6-dimethoxy-3-methyl-1,4-benzoquinon-2-ylmethyl)phenyl]propionyl]-4-methylpiperidine,
N-[3-[4-(5,6-dimethoxy-3-methyl-1,4-benzoquinon-2-ylmethyl)phenyl]propionyl]-2-methylpiperidine,
N-(3-[4-(5,6-dimethoxy-3-methyl-1,4-benzoquinon-2-ylmethyl)phenyl]propionyl]-3-methylpiperidine,
N-[3-[4-(5,6-dimethoxy-3-methyl-1,4-benzoquinon-2-ylmethyl)phenyl]propionyl]-4-methoxyaniline,
N-[3-[4-(5,6-dimethoxy-3-methyl-1,4-benzoquinon-2-ylmethyl)phenyl]propionyl]-2-hydroxyaniline,
N-[3-[4-(5,6-dimethoxy-3-methyl-1,4-benzoquinon-2-ylmethyl)phenyl]propionyl]-3,4-dimethoxyaniline,
N-[3-[4-(5,6-dimethoxy-3-methyl-1,4-benzoquinon-2-ylmethyl)phenyl]propionyl]-D,L-alaminol,
N-[3-[4-(5,6-dimethoxy-3-methyl-1,4-benzoquinon-2-ylmethyl)phenyl]propionyl]-D,L-pipecolic acid ethylester,
N-[3-[4-(5,6-dimethoxy-3-methyl-1,4-benzoquinon-2-ylmethyl)phenyl]propionyl]-L-prolinamide,
4-[3-[4-(5,6-dimethoxy-3-methyl-1,4-benzoquinon-2-ylmethyl)phenyl]propionyl]aminophenylacetonitrile,
N-[3-[4-(5,6-dimethoxy-3-methyl-1,4-benzoquinon-2-ylmethyl)phenyl]propionyl]-4-pentylaniline,
N-[3-[4-(5,6-dimethoxy-3-methyl-1,4-benzoquinon-2-ylmethyl)phenyl]propionyl]-(s)-(–)-1-phenylethylamine,
N-[3-[4-(5,6-dimethoxy-3-methyl-1,4-benzoquinon-2-ylmethyl)phenyl]propionyl]-(R)-(+)-1-phenylethylamine,
N-[3-[4-(5,6-dimethoxy-3-methyl-1,4-benzoquinon-2-ylmethyl)phenyl]propionyl]-1,3-dimethylbutylamine,
N-[3-[4-(5,6-dimethoxy-3-methyl-1,4-benzoquinon-2-ylmethyl)phenyl]propionyl]cycloheptylamine,
N-[3-[4-(5,6-dimethoxy-3-methyl-1,4-benzoquinon-2-ylmethyl)phenyl]propionyl]-3,5-dimethylpiperidine,
1-[3-[4-(5,6-dimethoxy-3-methyl-1,4-benzoquinon-2-ylmethyl)phenyl]propionyl]-4-ethoxycarbonylpiperazine,
1-[3-[4-(5,6-dimethoxy-3-methyl-1,4-benzoquinon-2-ylmethyl)phenyl]propionyl]-4-phenylpiperazine,
1-[3-[4-(5,6-dimethoxy-3-methyl-1,4-benzoquinon-2-ylmethyl)phenyl]propionyl]-4-hydroxy-4-phenylpiperidine,
1-[3-[4-(5,6-dimethoxy-3-methyl-1,4-benzoquinon-2-ylmethyl)phenyl]propionyl]-4-(4-chlorophenyl)-4-hydroxypiperidine,
1-[3-[4-(5,6-dimethoxy-3-methyl-1,4-benzoquinon-2-ylmethyl)phenyl]propionyl]-4-(2-methoxyphenyl)piperazine,
N-[3-[4-(5,6-dimethoxy-3-methyl-1,4-benzoquinon-2-ylmethyl)phenyl]propionyl]-6,7-dimethoxy-1,2,3,4-tetrahydroisoquinoline,
4-acetyl-4-phenyl-1-[3-[4-(5,6-dimethoxy-3-methyl-1,4-benzoquinon-2-ylmethyl)phenyl]propionyl]piperidine,
N-[3-[4-(5,6-dimethoxy-3-methyl-1,4-benzoquinon-2-ylmethyl)phenyl]propionyl]-1,2,3,4-tetrahydroisoquinoline,
N-[3-[4-(5,6-dimethoxy-3-methyl-1,4-benzoquinon-2-ylmethyl)phenyl]propionyl]isoamylamine, N-[3-[4-(5,6-dimethoxy-3-methyl-1,4-benzoquinon-2-ylmethyl)phenyl]propionyl]cyclohexylamine,
N-[3-[4-(5,6-dimethoxy-3-methyl-1,4-benzoquinon-2-ylmethyl)phenyl]propionyl]-4-hydroxyamine,
4-(5,6-dimethoxy-3-methyl-1,4-benzoquinon-2-ylmethyl)benzoic acid,
N-[4-(5,6-dimethoxy-3-methyl-1,4-benzoquinon-2-ylmethyl)benzoyl]morpholine,
N-[4-(5,6-dimethoxy-3-methyl-1,4-benzoquinon-2-ylmethyl)benzoyl]isopropylamine,
N-[4-(5,6-dimethoxy-3-methyl-1,4-benzoquinon-2-ylmethyl)benzoyl]piperidine,
N-[4-(5,6-dimethoxy-3-methyl-1,4-benzoquinon-2-ylmethyl)benzoyl]thiomorpholine,
3-(5,6-dimethoxy-3-methyl-1,4-benzoquinon-2-ylmethyl)benzoic acid,
N-[3-(5,6-dimethoxy-3-methyl-1,4-benzoquinon-2-ylmethyl)benzoyl]isopropylamine,
N-[3-(5,6-dimethoxy-3-methyl-1,4-benzoquinon-2-ylmethyl)piperidine,
N-[3-(5,6-dimethoxy-3-methyl-1,4-benzoquinon-2-ylmethyl)morpholine,
N-[3-(5,6-dimethoxy-3-methyl-1,4-benzoquinon-2-ylmethyl)thiomorpholine,
4-[4-(5,6-dimethoxy-3-methyl-1,4-benzoquinon-2-ylmethyl)phenyl]-n-butyric acid,
N-[4-[4-(5,6-dimethoxy-3-methyl-1,4-benzoquinon-2-ylmethyl)phenyl]butanoyl]morpholine,
N-[4-[4-(5,6-dimethoxy-3-methyl-1,4-benzoquinon-2-ylmethyl)phenyl]butanoyl]thiomorpholine,
N-[4-[4-(5,6-dimethoxy-3-methyl-1,4-benzoquinon-2-ylmethyl)phenyl]butanoyl]piperidine,
N-[4-[4-(5,6-dimethoxy-3-methyl-1,4-benzoquinon-2-ylmethyl)phenyl]butanoyl]isopropylamine,
4-(5,6-dimethoxy-3-methyl-1,4-benzoquinon-2-ylmethyl)phenylacetic acid,
N-[4-(5,6-dimethoxy-3-methyl-1,4-benzoquinon-2-ylmethyl)phenylacetyl]morpholine,
N-[4-(5,6-dimethoxy-3-methyl-1,4-benzoquinon-2-ylmethyl)phenylacetyl]piperidine,
N-[4-(5,6-dimethoxy-3-methyl-1,4-benzoquinon-2-ylmethyl)phenylacetyl]thiomorpholine,
N-[4-(5,6-dimethoxy-3-methyl-1,4-benzoquinon-2-ylmethyl)phenylacetyl]isopropylamine,
3-(5,6-dimethoxy-3-methyl-1,4-benzoquinon-2-ylmethyl)phenylacetic acid,
N-[3-(5,6-dimethoxy-3-methyl-1,4-benzoquinon-2-ylmethyl)phenylacetyl]piperidine,
N-[3-(5,6-dimethoxy-3-methyl-1,4-benzoquinon-2-ylmethyl)phenylacetyl]thiomorpholine,
N-[3-(5,6-dimethoxy-3-methyl-1,4-benzoquinon-2-ylmethyl)phenylacetyl]morpholine,
N-[3-(5,6-dimethoxy-3-methyl-1,4-benzoquinon-2-ylmethyl)phenylacetyl]morpholine,
4-[3-(5,6-dimethoxy-3-methyl-1,4-benzoquinon-2-ylmethyl)phenyl]-n-butyric acid,
N-[4-[3-(5,6-dimethoxy-3-methyl-1,4-benzoquinon-2-ylmethyl)phenyl]butanoyl]piperidine,
N-[4-[3-(5,6-dimethoxy-3-methyl-1,4-benzoquinon-2-ylmethyl)phenyl]butanoyl]thiomorpholine,
N-[4-(3-(5,6-dimethoxy-3-methyl-1,4-benzoquinon-2-ylmethyl)phenyl]butanoyl]morpholine, and
N-[4-[3-(5,6-dimethoxy-3-methyl-1,4-benzoquinon-2-ylmethyl)phenyl]butanoyl]isopropylamine.

The benzoquinone derivative of the general formula (1) that is used as an active ingredient of the present invention may be prepared according to the method described in Japanese Unexamined Patent Publication (Kokai) No. 62 (1987)-286949 or Chem. Pharm. Bull., 44(1): 139–144 (1996) or a method based thereupon. The compound represented by the general formula (I) of Japanese Unexamined Patent Publication No. 62-286949 can be produced, for example, by the following methods:

Process I

A compound represented by the general formula (IV)

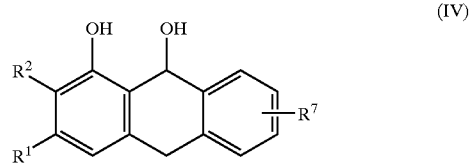

(wherein $R^1$, $R^2$ and $R^3$ each independently represents a hydrogen atom, a methyl group or a methoxy group, and $R^\partial$ represents a group

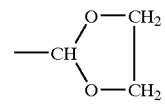

or —$CH(OC_2H_5)_2$)

can be obtained by acting a halide Grignard reagent represented by a general formula (III)

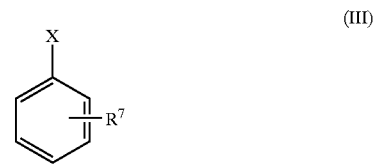

(wherein X represents a bromine atom or a chlorine atom and $R^7$ is as define above) to an aldehyde represented by a general formula (II)

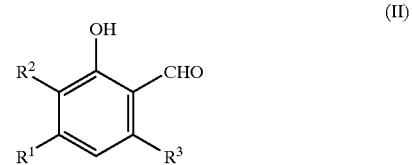

(wherein $R^1$, $R^2$, and $R^3$ are as defined above). The compound (IV) is converted into an aldehyde represented by a general formula (v)

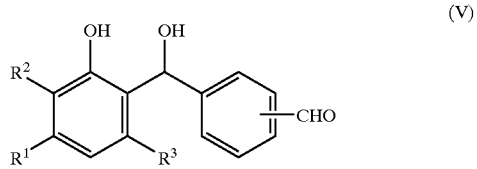

an acid, for example, hydrochloric acid. A compound represented by a general formula (VI)

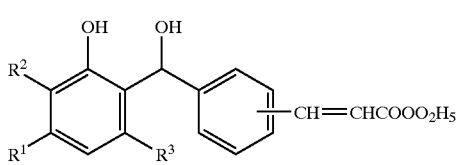

(VI)

(wherein $R^1$, $R^2$, and $R^3$ are as defined above) can be obtained by acting Witting reagent of triethylphosphonoacetate to the aldehyde.

The compound (VI) is converted into an acetylated compound by reacting thereto, acetic anhydride in the presence of a base, for example, pyridine, and, subsequently, the acetylated compound is catalytically reduced in the presence of palladium black in glacial acetic acid to obtain a compound represented by a general formula (VII)

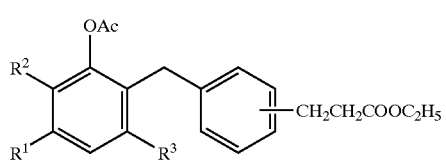

(VII)

(wherein $R^1$, $R^2$, and $R^3$ are as defined above).

The compound (VII) is subjected to hydrolysis, reduction or esterification through a conventional method to obtain a compound represented by a general formula (VIII)

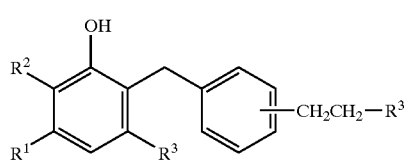

(VIII)

(wherein $R^1$, $R^2$, and $R^3$ are as defined above and $R^8$ represents a hydroxymethyl group, a carboxyl group, or a lower alkoxycarbonyl group).

Subsequently, the compound (VIII) is oxidized with oxygen in the presence of potassium nitrosodisulfonate or salcomine, to obtain the compound of the present invention of the general formula (Ia)

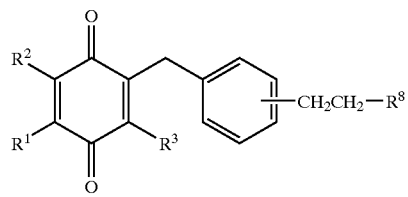

(Ia)

(wherein $R^1$, $R^2$, and $R^3$ are as defined above).

The compound of the present invention may be also produced by the following method:

Process II

A compound of a general formula (IX) can be obtained from 2,5-dimethoxybenzaldehyde through the following route as described above.

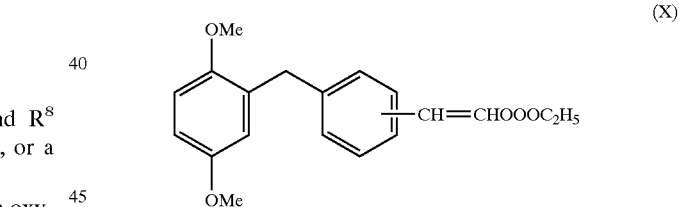

(IX)

The compound (IX) is converted into a chloride using thionychloride, etc. and, then, is subjected to dechlorination, for example reduction with zinc-glacial acetic acid to obtain a compound of a formula (X).

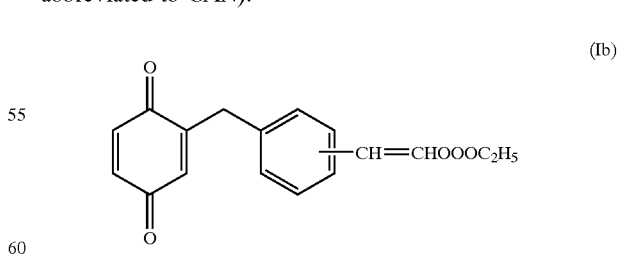

(X)

The compound represented by a formula (Ib) of the present invention can be obtained by oxidation of the compound (X) with ammonium nitrate cesium (hereinafter abbreviated to CAN).

(Ib)

The compound (Ib) may be converted into various compounds of the present invention through hydrolysis, reduction, amidation, etc., as appropriate, under conventionally employed condition.

Also, in the general formula (1) a benzoquinone derivative wherein $R_1$ and $R_2$ are a hydrogen atom, a methyl group or a methoxy group; $R_3$ is a hydrogen atom or a methyl group; $R_4$ is a carboxyl group which is optionally esterified or amidated; Z is

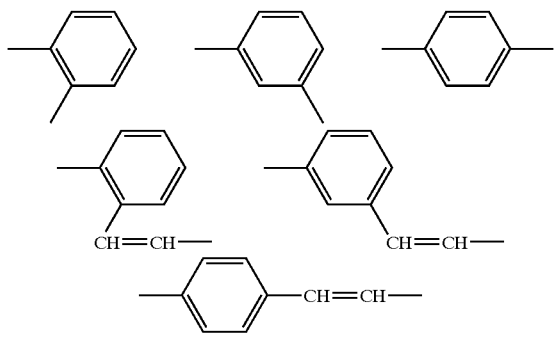

and, n is represented by an integer from 0 or 2, may also be prepared according to the following synthetic procedure.

Method 1.

An aldehyde represented by the general formula (II):

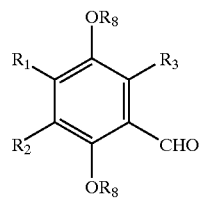

(II)

wherein $R_1$, $R_2$, and $R_3$ are as defined above, and $R_8$ represents an alkyl group having 1 to 5 carbons is allowed to react with a Grignard reagent of a halide represented by the general formula (III):

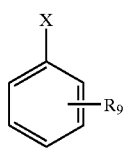

(III)

wherein X represents a bromine or a chlorine atom and $R_9$ represents a group:

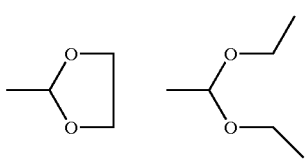

to obtain a compound represented by the general formula (IV):

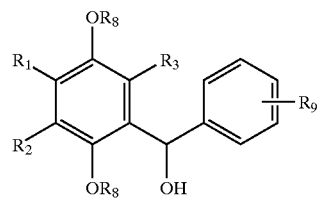

(IV)

wherein $R_1$, $R_2$, $R_3$, $R_8$ and $R_9$ are as defined above.

Compound (IV) is allowed to react with acetic anhydride in the presence of, for example, a base such as pyridine and 4-dimethylaminopyridine to prepare an acetylated compound, which is then subjected to a deacetal reaction in an acetone solution in the presence of an acid such as p-toluenesulfonic acid or camphorsulfonic acid to prepare an aldehyde represented by the general formula (V):

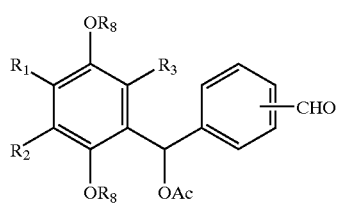

(V)

wherein $R_1$, $R_2$, $R_3$ and $R_8$ are as defined above). The aldehyde is allowed to react with a Wittig reagent of triethyl phosphonoacetate, which is further reduced with a reducing agent such as triethylsilane in the presence of an acidic catalyst such as trimethylsilyl trifluoromethanesulfonate (hereinafter referred to as TMSOTf) to yield a compound represented by the general formula (VI):

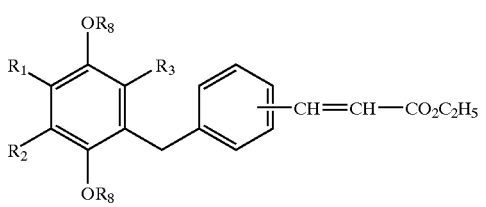

(VI)

wherein $R_1$, $R_2$, $R_3$ and $R_8$ are as defined above.

Compound (VI) is hydrolyzed or is further esterified or amidated in a conventional method to prepare a compound represented by the general formula (VII):

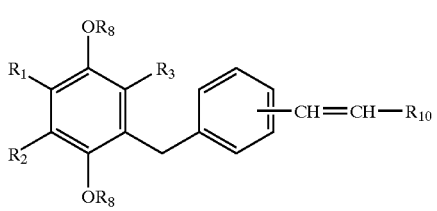

(VII)

wherein $R_1$, $R_2$, $R_3$ and $R_8$ are as defined above, and $R_{10}$ represents a carboxyl group which is optionally esterified or amidated.

The compound (VII) is then oxidized with ceric ammonium nitrate (hereinafter referred to as CAN) to yield the compound of the present invention represented by the general formula (Ia):

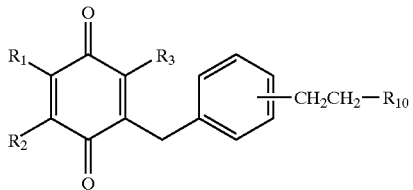
(Ia)

wherein $R_1$, $R_2$, $R_3$ and $R_{10}$ are as defined above. Using the compound of formula (Ia) wherein $R_{10}$ is a carboxyl group, an ester or an amide derivative may be obtained by a conventionally used esterification or amidation reaction, respectively.

Method 2.

The compound represented by the general formula (VI) obtained in the above method is subjected to a catalytic hydrogenation and then is hydrolyzed or is further esterified or amidated in a conventional method to prepare a compound represented by the general formula (VIII):

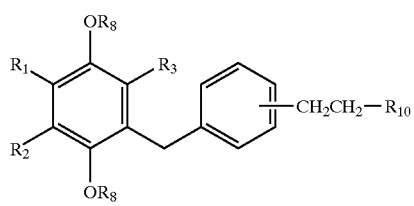
(VIII)

wherein $R_1$, $R_2$, $R_3$, $R_8$ and $R_{10}$ are as defined above.

Subsequently, compound (VIII) can be oxidized with CAN to yield the compound of the present invention represented by the general formula (Ib):

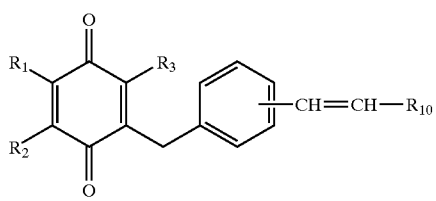
(Ib)

wherein $R_1$, $R_2$, $R_3$ and $R_{10}$ are as defined above.

The compound of formula (Ib) wherein $R_{10}$ is a carboxyl group may be converted to an ester or an amide derivative through a conventional procedure of esterification or amidation, respectively.

A benzoquinone derivative of the general formula (I) wherein $R_1$ and $R_2$ are a hydrogen atom, a methyl group or a methoxy group; $R_3$ is a hydrogen atom or a methyl group; $R_4$, is a carboxyl group which is optionally esterified or amidated; z is

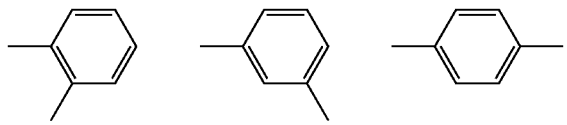

and n is an integer 0 may also be prepared by the following synthetic procedure.

Method 3.

An aldehyde obtained in the above method represented by the general formula (V):

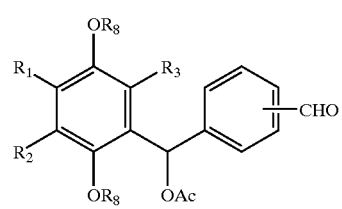
(V)

wherein $R_1$, $R_2$, $R_3$ and $R_8$ are as defined above, is oxidized using an oxidizing agent such as potassium permanganate, silver oxide, activated manganese dioxide and pyridinium dichromate, preferably silver oxide in an aqueous solution of sodium hydroxide to prepare a carboxylic acid represented by the general formula (IX):

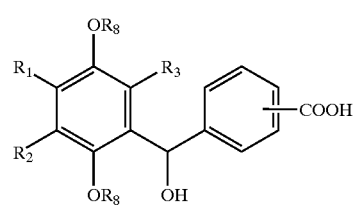
(IX)

wherein $R_1$, $R_2$, $R_3$ and $R_8$ are as defined above.

The carboxylic acid is reduced using a reducing agent such as triethylsilane in the presence of an acidic catalyst such as TMSOTf to yield a compound represented by the general formula (X):

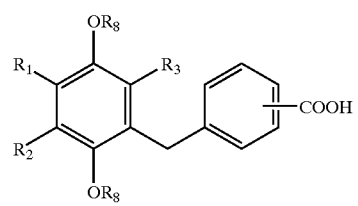
(X)

wherein $R_1$, $R_2$, $R_3$ and $R_8$ are as defined above.

Compound (X) may be further esterified or amidated to prepare a compound represented by the general formula (XI):

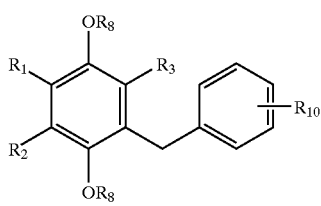

(XI)

wherein $R_1$, $R_2$, $R_3$ and $R_8$ are as defined above, and $R_{10}$ is a carboxyl group which is optionally esterified or amidated.

Subsequently, compound (XI) can be oxidized with CAN to yield the compound of the present invention represented by the general formula (Ic):

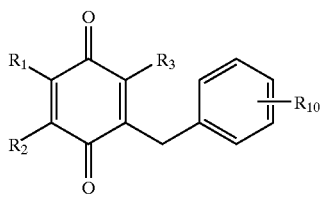

(Ic)

wherein $R_1$, $R_2$, $R_3$ and $R_{10}$ are as defined above. The compound of formula (Ic) wherein $R_{10}$ is a carboxyl group may be converted to an ester or an amide derivative through a conventional procedure of esterification or amidation, respectively.

Method 4.

An aldehyde represented by the general formula (II):

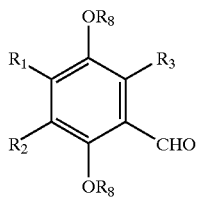

(II)

wherein $R_1$, $R_2$, $R_3$ and $R_8$ are as defined above, and an iodobenzoic acid ester represented by the general formula (XII):

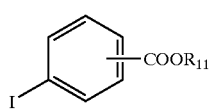

(XII)

wherein $R_{11}$, represents an alkyl group such as a methyl group and an ethyl group, may be reacted in the presence of zinc chloride and an alkyllithium reagent such as methyllithium, n-butyllithium, or t-butyllithium to prepare an ester represented by the general formula (XIII):

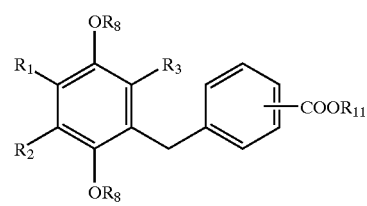

(XIII)

wherein $R_1$, $R_2$, $R_3$, $R_8$ and $R_{11}$ are as defined above.

The ester is reduced in a method similar to the one described above and then hydrolyzed or is further esterified or amidated in a conventionally used method, to prepare a compound represented by the general formula (XI):

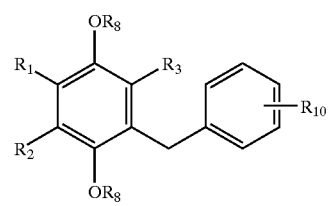

(XI)

wherein $R_1$, $R_2$, $R_3$ and $R_8$ are as defined above, and $R_{10}$ is a carboxyl group which is optionally esterified or amidated.

Subsequently, compound (XI) can be oxidized with CAN to yield the compound of the present invention represented by the general formula (Ic):

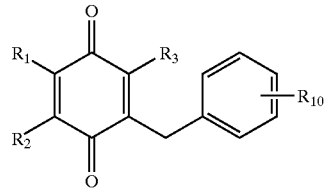

(Ic)

wherein $R_1$, $R_2$, $R_3$ and $R_{10}$ are as defined above. The compound of formula (Ic) wherein $R_{10}$ is a carboxyl group may be converted to an ester or an amide derivative through a conventional procedure of esterification or amidation, respectively.

A benzoquinone derivative of the general formula (I) wherein $R_1$ and $R_2$ are a hydrogen atom, a methyl or a methoxy group; $R_3$ is a hydrogen atom or a methyl group; $R_4$ is a carboxyl group which is optionally esterified or amidated; Z is

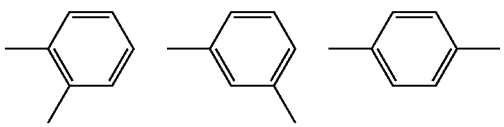

and n is an integer 1 or 3, may also be prepared by the following synthetic procedure.

Method 5.

A carboxylic acid obtained in the above method represented by the general formula (XIV):

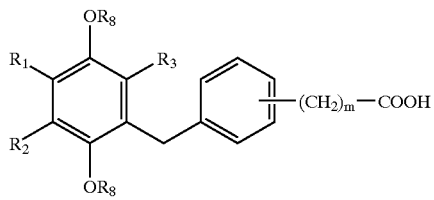

(XIV)

wherein $R_1$, $R_2$, $R_3$ and $R_8$ are as defined above and m is an integer 0 or 2, is reacted with oxalyl chloride or thionyl chloride to prepare an acid chloride, which is then reacted with an excess of diazomethane to convert to the corresponding diazomethyl ketone. The diazomethyl ketone can be then subjected to Wolff rearrangement reaction in the presence of silver oxide or a silver salt catalyst such as silver acetate to yield a carboxylic acid derivative represented by the general formula (XV):

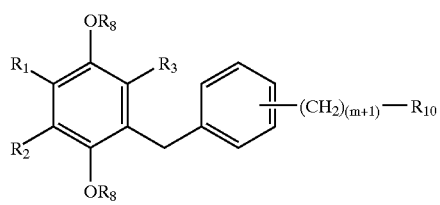

(XV)

wherein $R_1$, $R_2$, $R_3$ and $R_8$ are as defined above and m is an integer 0 or 2, $R_{10}$ is a carboxyl group which is optionally esterified or amidated, said derivative having a carbon chain increased by one carbon. Through this rearrangement reaction, carboxylic acids, esters, and amides can be synthesized using water, alcohols, and amines as reaction solvent, respectively.

Subsequently, compound (xv) can be oxidized with CAN to yield the compound of the present invention represented by the general formula (Id):

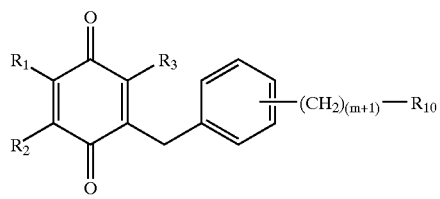

(Id)

wherein $R_1$, $R_2$, $R_3$, $R_{10}$ and m are as defined above. The compound of formula (Id) wherein $R_{10}$ is a carboxyl group may be converted to an ester or an amide derivative through a conventional procedure of esterification or amidation, respectively.

Method 6.

In stead of the compound represented by the above general formula (XIV), a carboxylic acid represented by the general formula (XVI):

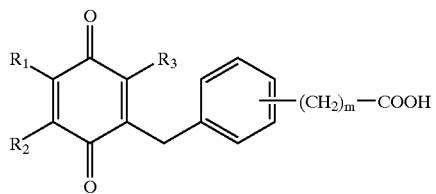

(XVI)

wherein $R_1$, $R_2$, $R_3$ and m are as defined above may be used as a starting material and treated as in Method 5 to produce a carboxylic acid derivative represented by the general formula (Id) having an increased number of carbon.

Using the above method 5 or 6, it is possible to prepare benzoquinone derivatives having a further extended methylene chain wherein m is represented by an integer 4, 5 or 6.

Compound (I) of the present invention thus obtained can be converted to various salts mentioned above, as desired, and can be purified by means of recrystallization, column chromatography, and the like.

Furthermore, some of the compounds (I) of the present invention have an asymmetric center, and these optical isomers are encompassed by the present invention and can be obtained from mixture of racemic compounds as single optically active isomers through separation with various means. Exemplary methods used include:

(1) separation with an optically active column;
(2) conversion into salts using an optically active acid, followed by separation via recrystallization;
(3) separation by enzymatic reactions; and
(4) separation by combinations of the above (1) to (3).

Since the compounds as claimed in the present invention represented by the general formula (I) can inhibit the activation of NF-κB, they are useful as preventive and therapeutic agents for diseases caused by the activation of NF-κB, for example diseases caused by the excessive production of inflammatory mediators and viral propagation. Specifically, they are useful as therapeutic and preventive agents for diseases caused by the excessive production of NO and/or TNF-α, including for example septic shock, osteoarthritis, rheumatoid arthritis, cachexia, multiple organ failure, inflammatory bowel diseases, malaria, acquired immune deficiency syndrome, human T-cell leukemia, meningitis, hepatitis, type II diabetes, multiple sclerosis, Behcet disease, systemic lupus erythematosus, ischemic heart disease, Alzheimer's disease, and the like.

When the compounds of the present invention are used as the above-mentioned pharmaceutical compositions, they may be used orally in the form of tablets, capsules, elixirs, microcapsules, and the like, or parenterally in the form of injections and the like such as solutions or suspensions with water or other pharmaceutically acceptable liquids. For example, they can be prepared by mixing the invention compound with pharmaceutically acceptable carriers, flavoring agents, excipients, stabilizers, and the like in a commonly recognized form. Additives that can be blended into tablets etc. include, for example, binders such as gelatin, swelling agents such as corn starch, excipients such as crystalline cellulose, lubricants such as magnesium stearate, and the like. When formulated into capsules, the above compositions may further include liquid carriers. Aseptic compositions for injection can also be formulated in the conventional manner.

As aqueous solutions for injection, there may be mentioned isotonic solution that contain glucose etc., and they may be used in combination with suitable solubilizer such as polyethyleneglycol. Buffers, stabilizers, preservatives, antioxidants, soothing agents, and the like may also be blended. The pharmaceutical preparations thus obtained can be administered to mammals including humans. Though the dosage varies depending on the pathologic state etc. the daily dose per human adult is generally about 0.01 to 100 mg, preferably about 0.1 to 50 mg, and more preferably about 1.0 to 25 mg in oral. When they are given parenterally, the daily dose per human adult is generally intravenously administered at amounts about 0.001 to 50 mg, preferably about 0.01 to 25 mg, more preferably about 0.1 to 10 mg.

The effect of NF-κB inhibition can be examined by detecting the expression of genes regulated by the activation of NF-κB, or by determining directly or indirectly the amount expressed of proteins encoded by the genes.

The effect of suppressing the excessive expression of inflammatory proteins may be examined, as shown in the results of Experimental Example 3, by stimulating cells or individual animals with a cytokine such as IL-1 and TNF-α and a lipopolysaccharide, and then determining directly or indirectly the amount of inflammatory proteins that may be increased in the culture medium or the body fluid.

Also, methods of confirming in vivo the general anti inflammatory effects comprise determining the effect of suppressing edema produced using carrageenin as a prophlogistic agent. It has already been reported that the inhibition of NO and TNF-α production are effective in this model (Filion, M. C. and Phillips, N. C. (1997) Br. J. Pharmacol. 122: 551–557; Tsao, P. W., Suzuki, T., Totsuka, R., Murata, T., Takagi, T., Ohmachi, Y., Fujimura, H. and Takata, I. (1997) Clin. Immunol. Immunopathol. 83: 173–178; Cuzzocrea, S., Zingarelli, B., Hake, P., Salzman, A. L. and Szabo, C. (1998) Free Radic. Biol. Med. 24: 450–459). Furthermore, for specific diseases the efficacy as a therapeutic agent for sepsis can be evaluated by administering a lipopolysaccharide to animals such as mice and then determining the survival ratio of the animals.

The efficacy as a therapeutic agent for rheumatoid arthritis can also be evaluated in animal models of arthritis using adjuvants. When model animals of myocardial infarction are used, DNA having the decoy sequence of NF-κB is shown to suppress the lesion of the infarction (Sawa, Y., Morishita, R., Suzuki, K., Kagisaki, K., Kaneda, Y., Maeda, K., Kadoba, K. and Matsuda, H. (1997) Circulation 96: II-280–284; discussion II-285), and thereby such model animals are also suitable for investigating the efficacy of therapeutic agents for ischemic heart diseases.

Thus the efficacy of NF-κB inhibitors having an activity of inhibiting the production of NO and TNF-α as therapeutic agents can be confirmed using known animal models that can be prepared by a person skilled in the art.

EXAMPLES

The present invention is now explained in more detail with reference to the following examples and experimental examples. However, it should be noted that the present invention is not limited by them in any way.

Example 1

3-[4-(5,6-dimethoxy-3-methyl-1,4-benzoquinon-2-ylmethyl)phenyl]propionic Acid

Step 1. 2-{4-[hydroxy-(2,3,4,5-tetramethoxy-6-methylphenyl)methyl]phenyl}-1,3-dioxolane To an ice-cold solution of 2,3,4,5-tetramethoxy-6-methylbenzaldehyde (5.03 g, 20.94 mmol) in THF (200 ml) was added dropwise a Grignard reagent prepared from 2-(4-bromophenyl)-1,3-dioxolane (12.0 g, 52.4 mmol) and magnesium (1.40 g, 57.6 mmol), and then stirred at room temperature for 4 hours. The reaction mixture was poured into water and was extracted with ether. After the extract was washed with water and dried, and then the solvent was distilled off. The residue was purified by a silica gel column chromatography (hexane:ethyl acetate=3:1) to yield the title compound (7.80 g, 20.0 mmol, yield 96%).

Step 2. 4-[acetoxy-(2,3,4,5-tetramethoxy-6-methylphenyl)methyl]benzaldehyde

The compound (7.80 g, 20.0 mmol) obtained in Step 1 was dissolved in methylene chloride (300 ml), and then acetic anhydride (6.12 g, 60.0 mmol), pyridine (4.74 g, 59.9 mmol), and 4-dimethylaminopyridine (1.22 g, 10.0 mmol) were added thereto, which was then stirred at room temperature for 16 hours.

After the reaction mixture was washed with a 5% aqueous solution of hydrochloric acid and saturated saline, it was dried and the solvent was distilled off. The residue and p-toluenesulfonic acid monohydrate (200 mg) were dissolved in acetone (300 ml), which was stirred at room temperature for 6 hours. After the reaction mixture was concentrated under reduced pressure, water and ether were added for extraction. The extract was washed with water, dried, and then the solvent was distilled off. The residue was purified by a silica gel column chromatography (hexane:ethyl acetate=3:1) to yield the title compound (3.97 g, 10.2 mmol, yield 51%).

Step 3. 3-{4-[acetoxy-(2,3,4,5-tetramethoxy-6-methylphenyl)methyl]phenyl}acrylic Acid Ethylester Triethyl phosphonoacetate (1.70 g, 7.58 mmol) was dissolved in THF (150 ml) and sodium hydride (303 mg, 60%, 7.58 mmol) was added at room temperature and then the mixture was stirred for 40 minutes. To the reaction mixture was added dropwise under ice-cooling a solution of the compound (2.26 g, 5.82 mmol) obtained in Step 2 in THF (50 ml) and the mixture was stirred at room temperature for 16 hours. The reaction mixture was poured into water and extracted with ether. The extract was washed with water, dried, and then the solvent was distilled off. The residue was purified by a silica gel column chromatography (hexane:ethyl acetate=3:1) to yield the title compound (2.37 g, 5.17 mmol, yield 89%).

Step 4. 3-[4-(2,3,4,5-tetramethoxy-6-methylbenzyl) phenyl]acrylic Acid Ethylester To a solution of triethylsilane (720 mg, 6.21 mmol) and trimethylsilyl trifluoromethanesulfonate (TMSOTf) in methylene chloride (250 ml) was added dropwise a solution of the compound (2.37 g, 5.17 mmol) obtained in Step 3 in methylene chloride (50 ml) and the mixture was stirred at room temperature for 30 minutes. The reaction mixture was washed with water, dried, and then the solvent was distilled off. The residue was purified by a silica gel column chromatography (hexane:ethyl acetate=4:1) to yield the title compound (1.90 g, 4.74 mmol, yield 92%).

Step 5. 3-[4-(2,3,4,5-tetramethoxy-6-methylbenzyl) phenyl]propionic Acid Ethylester The compound (1.07 g, 2.67 mmol) obtained in step 4 was dissolved in ethanol (100 ml) and 5% Pd-carbon (200 mg)

was added thereto, which was then stirred under a stream of hydrogen at room temperature for 16 hours. The reaction mixture was filtered and the filtrate was concentrated to yield the title compound (914 mg, 2.27 mmol, yield 85%).

Step 6. 3-[4-(2,3,4,5-tetramethoxy-6-methylbenzyl)phenyl]propionic Acid

The compound (914 mg, 2.27 mmol) obtained in Step 5 was dissolved in a mixture of an aqueous solution of 2 N sodium hydroxide (30 ml) and 1,4-dioxane (15 ml) and the mixture was stirred at 70° C. for 3 hours. The reaction mixture was acidified by adding concentrated hydrochloric acid and then was extracted with ethyl acetate. The extract was washed with water, dried, and then the solvent was distilled off to yield the title compound (731 mg, 1.95 mmol, yield 86%).

Step 7. 3-[4-(5,6-dimethoxy-3-methyl-1,4-benzoquinon-2-ylmethyl)phenyl]propionic Acid The compound (1.00 g, 2.67 mmol) obtained in Step 6 was dissolved in a mixture of acetonitrile (30 ml) and water (10 ml), to which was added CAN (ceric ammonium nitrate) (2.34 g, 4.27 mmol) and the mixture was stirred at room temperature for 30 minutes. The reaction mixture was poured into water and was extracted with ether. After the extract was washed with water and dried, the solvent was distilled off. The residue was purified by a silica gel column chromatography (5% methanol-methylene chloride) and then was crystallized in ethanol/hexane to yield the title compound (662 mg, 1.92 mmol, yield 72%).

Example 2

3-[4-(5,6-dimethoxy-3-methyl-1,4-benzoquinon-2-ylmethyl)phenyl]acrylic Acid

Step 1. 3-[4-(2,3,4,5-tetramethoxy-6-methylbenzyl)phenyl]acrylic Acid

The compound (1.35 g, 3.36 mmol) obtained in Step 4 of Example 1 was dissolved in a mixture of an aqueous solution of 2 N sodium hydroxide (30 ml) and 1,4-dioxane (15 ml), and the mixture was stirred at 70° C. for 3 hours. The reaction mixture was acidified by adding concentrated hydrochloric acid and then was extracted with ethyl acetate. The extract was washed with water, dried, and then the solvent was distilled off to yield the title compound (1.20 g, 3.23 mmol, yield 96%).

Step 2. 3-[4-(5,6-dimethoxy-3-methyl-1,4-benzoquinon-2-ylmethyl)phenyl]acrylic Acid The compound (589 mg, 1.58 mmol) obtained in Step 1 was dissolved in a mixture of acetonitrile (30 ml) and water (10 ml), to which was added CAN (1.38 g, 2.52 mmol) and the mixture was stirred at room temperature for 1 hour. The reaction mixture was poured into water and was extracted with ether. After the extract was washed with water and dried, the solvent was distilled off. The residue was purified by a silica gel column chromatography (5% methanol-methylene chloride) to yield the title compound (452 mg, 1.32 mmol, yield 84%).

Example 3

N-[3-[4-(5,6-dimethoxy-3-methyl-1,4-benzoquinon-2-ylmethyl)phenyl]propionyl]morpholine To a solution of 3-[4-(5,6-dimethoxy-3-methyl-1,4-benzoquinon-2-ylmethyl)phenyl]propionic acid (100 mg, 0.29 mmol) obtained in Example 1 and morpholine (30 mg, 0.35 mmol) in methylene chloride (10 ml) was added 1-ethyl-3-(3-dimethylaminopropyl)carbodiimide hydrochloride (84 mg, 0.44 mmol) and the mixture was stirred at room temperature for 3 hours. The reaction mixture was concentrated under reduced pressure and was purified by a middle-pressure column chromatography using silica gel (hexane:ethyl acetate=1:2).

The yellow powder thus obtained was crystallized from methylene chloride-diethylether to yield the title compound (89 mg, 0.22 mmol, yield 74%) as a yellow crystal.

Example 4

N-[3-[4-(5,6-dimethoxy-3-methyl-1,4-benzoquinon-2-ylmethyl)phenyl]propionyl]thiomorpholine To a solution of 3-[4-(5,6-dimethoxy-3-methyl-1,4-benzoquinon-2-ylmethyl)phenyl]propionic acid (27 mg, 0.078 mmol) obtained in Example 1 and ethyl chlorocarbonate (15 mg, 0.139 mmol) in THF (10 ml) was added triethylamine (14 mg, 0.139 mmol) at −10° C. followed by stirring for 30 minutes, and then thiomorpholine (20 mg, 0.194 mmol) was added thereto followed by stirring at room temperature for 1 hour. The reaction mixture was diluted with water and extracted with ether. The extract was washed with water, dried, and then the solvent was distilled off. The resulting residue was purified by a middle-pressure column chromatography using silica gel (hexane:ethyl acetate=1:1). The yellow powder thus obtained was crystallized from methylene chloride-diethylether to yield the title compound (26 mg, 0.061 mmol, yield 77%) as a yellow crystal.

Examples 5 and 6

N-[3-[4-(5,6-dimethoxy-3-methyl-1,4-benzoquinon-2-ylmethyl)phenyl]propionyl]thiomorpholine S-oxide (Example 5) and N-[3-[4-(5,6-dimethoxy-3-methyl-1,4-benzoquinon-2-ylmethyl)phenyl]propionyl]thiomorpholine S-dioxide (Example 6)

To a solution of the compound (200 mg, 0.47 mmol) obtained in Example 4 in methylene chloride (50 ml) was added m-chloroperbenzoic acid (121 mg, 0.70 mmol) and the mixture was stirred at room temperature for 5 hours. The reaction mixture was washed with water, dried, and then concentrated under reduced pressure. The crude product thus obtained was purified by a silica gel column chromatography (5% methanol-methylene chloride) to yield the compound (60 mg, yield 28%) of Example 5 and the compound (50 mg, yield 24%) of Example 6.

Examples 7 to 20

According to the method of Example 3, the compounds of Examples 7 to 20 were synthesized.

Example 7

N-[3-[4-(5,6-dimethoxy-3-methyl-1,4-benzoquinon-2-ylmethyl)phenyl]propionyl]piperidine 3-[4-(5,6-dimethoxy-3-methyl-1,4-benzoquinon-2-ylmethyl)phenyl]propionic acid (200 mg, 0.58 mmol) obtained in Example 1 and piperidine (64 mg, 0.75 mmol) were used, and a method similar to that described in Example 3 was employed to obtain the title compound (118 mg, 0.79 mmol, yield 50%).

Example 8

N-[3-[4-(5,6-dimethoxy-3-methyl-1,4-benzoquinon-2-ylmethyl)phenyl]propionyl]dimethylamine 3-[4-(5,6-dimethoxy-3-methyl-1,4-benzoquinon-2-ylmethyl)phenyl]propionic acid (200 mg, 0.58 mmol)

obtained in Example 1 and dimethylamine hydrochloride (62 mg, 0.75 mmol) and triethylamine (76 mg, 0.75 mmol) were used, and a method similar to that described in Example 3 was employed to obtain the title compound (38 mg, 0.10 mmol, yield 18%).

Example 9

N-[3-[4-(5,6-dimethoxy-3-methyl-1,4-benzoquinon-2-ylmethyl)phenyl]propionyl]isopropylamine 3-[4-(5,6-dimethoxy-3-methyl-1,4-benzoquinon-2-ylmethyl)phenyl]propionic acid (200 mg, 0.58 mmol) obtained in Example 1 and isopropylamine (44 mg, 0.75 mmol) were used, and a method similar to that described in Example 3 was employed to obtain the title compound (46 mg, 0.12 mmol, yield 21%).

Example 10

N-[3-[4-(5,6-dimethoxy-3-methyl-1,4-benzoquinon-2-ylmethyl)phenyl]propionyl]ethanolamine 3-[4-(5,6-dimethoxy-3-methyl-1,4-benzoquinon-2-ylmethyl)phenyl]propionic acid (200 mg, 0.58 mmol) obtained in Example 1 and ethanolamine (47 mg, 0.75 mmol) were used, and a method similar to that described in Example 3 was employed to obtain the title compound (65 mg, 0.18 mmol, yield 29%).

Example 11

N-[3-[4-(5,6-dimethoxy-3-methyl-1,4-benzoquinon-2-ylmethyl)phenyl]propionyl]benzylamine 3-[(4-(5,6-dimethoxy-3-methyl-1,4-benzoquinon-2-ylmethyl)phenyl]propionic acid (200 mg, 0.58 mmol) obtained in Example 1 and benzylamine (80 mg, 0.75 mmol) were used, and a method similar to that described in Example 3 was employed to obtain the title compound (33 mg, 0.08 mmol, yield 13%).

Example 12

N-[3-[4-(5,6-dimethoxy-3-methyl-1,4-benzoquinon-2-ylmethyl)phenyl]propionyl]phenethylamine 3-[4-(5,6-dimethoxy-3-methyl-1,4-benzoquinon-2-ylmethyl)phenyl]propionic acid (200 mg, 0.58 mmol) obtained in Example 1 and phenethylamine (91 mg, 0.75 mmol) were used, and a method similar to that described in Example 3 was employed to obtain the title compound (61 mg, 0.14 mmol, yield 24%).

Example 13

N-[3-[4-(5,6-dimethoxy-3-methyl-1,4-benzoquinon-2-ylmethyl)phenyl]acryloyl]morpholine 3-[4-(5,6-dimethoxy-3-methyl-1,4-benzoquinon-2-ylmethyl)phenyl]acrylic acid (200 mg, 0.58 mmol) obtained in Example 2 and morpholine (65 mg, 0.75 mmol) were used, and a method similar to that described in Example 3 was employed to obtain the title compound (102 mg, 0.25 mmol, yield 43%).

Example 14

N-[3-[4-(5,6-dimethoxy-3-methyl-1,4-benzoquinon-2-ylmethyl)phenyl]acryloyl]thiomorpholine 3-[4-(5,6-dimethoxy-3-methyl-1,4-benzoquinon-2-ylmethyl)phenyl]acrylic acid (200 mg, 0.58 mmol) obtained in Example 2 and thiomorpholine (77 mg, 0.75 mmol) were used, and a method similar to that described in Example 3 was employed to obtain the title compound (140 mg, 0.33 mmol, yield 56%).

Example 15

N-[3-[4-(5,6-dimethoxy-3-methyl-1,4-benzoquinon-2-ylmethyl)phenyl]acryloyl]piperidine 3-[4-(5,6-dimethoxy-3-methyl-1,4-benzoquinon-2-ylmethyl)phenyl]acrylic acid (200 mg, 0.58 mmol) obtained in Example 2 and piperidine (65 mg, 0.76 mmol) were used, and a method similar to that described in Example 3 was employed to obtain the title compound (129 mg, 0.32 mmol, yield 54%).

Example 16

N-[3-[4-(5,6-dimethoxy-3-methyl-1,4-benzoquinon-2-ylmethyl)phenyl]acryloyl]dimethylamine 3-[4-(5,6-dimethoxy-3-methyl-1,4-benzoquinon-2-ylmethyl)phenyl]acrylic acid (200 my, 0.58 mmol) obtained in Example 2 and dimethylamine hydrochloride (61 mg, 0.75 mmol) and triethylamine (76 mg, 0.75 mmol) were used, and a method similar to that described in Example 3 was employed to obtain the title compound (23 mg, 0.06 mmol, yield 11%).

Example 17

N-[3-[4-(5,6-dimethoxy-3-methyl-1,4-benzoquinon-2-ylmethyl)phenyl]acryloyl]isopropylamine 3-[4-(5,6-dimethoxy-3-methyl-1,4-benzoquinon-2-ylmethyl)phenyl]acrylic acid (200 mg, 0.58 mmol) obtained in Example 2 and isopropylamine (44 mg, 0.75 mmol) were used, and a method similar to that described in Example 3 was employed to obtain the title compound (48 mg, 0.13 mmol, yield 22%).

Example 18

N-[3-[4-(5,6-dimethoxy-3-methyl-1,4-benzoquinon-2-ylmethyl)phenyl]acryloyl]ethanolamine 3-[4-(5,6-dimethoxy-3-methyl-1,4-benzoquinon-2-ylmethyl)phenyl]acrylic acid (200 mg, 0.58 mmol) obtained in Example 2 and ethanolamine (46 mg, 0.75 mmol) were used, and a method similar to that described in Example 3 was employed to obtain the title compound (14 mg, 0.04 mmol, yield 6%).

Example 19

N-[3-[4-[(5,6-dimethoxy-3-methyl-1,4-benzoquinon-2-ylmethyl)phenyl]acryloyl]benzylamine 3-[4-(5,6-dimethoxy-3-methyl-1,4-benzoquinon-2-ylmethyl)phenyl]acrylic acid (200 mg, 0.58 mmol) obtained in Example 2 and benzylamine (80 mg, 0.75 mmol) were used, and a method similar to that described in Example 3 was employed to obtain the title compound (104 mg, 0.24 mmol, yield 42%).

Example 20

N-[3-[4-(5,6-dimethoxy-3-methyl-1,4-benzoquinon-2-ylmethyl)phenyl]acryloyl]phenethylamine 3-[4-(5,6-dimethoxy-3-methyl-1,4-benzoquinon-2-ylmethyl)phenyl]acrylic acid (200 mg, 0.58 mmol) obtained in Example 2 and phenethylamine (91 mg, 0.75 mmol) were used, and a method similar to that described in Example 3 was employed to obtain the title compound (170 mg, 0.38 mmol, yield 65%).

Example 21

4-(5,6-dimethoxy-3-methyl-1,4-benzoquinon-2-ylmethyl)benzoic Acid

Method A

Step 1. 4-[hydroxy-(2,3,4,5-tetramethoxy-6-methylphenyl)methyl]benzoic Acid

After adding dropwise an aqueous solution (20 ml) of silver nitrate (3.06 g, 18.00 mmol) to an aqueous solution of 1 N sodium hydroxide (36 ml), a solution of 4-[acetoxy-(2, 3,4,5-tetramethoxy-6-methylphenyl)methyl]benzaldehyde (2.34 g, 6.00 mmol) obtained in Step 2 of Example 1 in THF (30 ml) was added dropwise and the mixture was stirred at room temperature for 5 hours. The reaction mixture was filtered and the solid was washed with hot water. The filtrate and the wash solution were combined, which was then acidified with concentrated hydrochloric acid and then was extracted with ether. The extract was dried and the solvent was distilled off to yield the title compound (2.3 g, 6.37 mmol, yield 100%).

NMR (CDCl$_3$): 2.27 (3H, s), 3.30 (3H, s), 3.75 (1H, m), 3.82 (3H, s), 3.85 (3H, s), 3.94 (3H, s), 6.04 (1H, broad), 7.42 (2H, m), 8.06 (2H, m) FABMS (m/z): 362 (M)$^+$.

Step 2. 4-(2,3,4,5-tetramethoxy-6-methylbenzyl) benzoic Acid

To a solution of triethylsilane (1.39 ml, 8.74 mmol) and TMSOTf (0.056 ml, 0.31 mmol) in methylene chloride (30 ml) was added dropwise a solution of the compound (2.26 g, 6.24 mmol) obtained in Step 1 in methylene chloride (12 ml) and the mixture was stirred at room temperature for 4 hours. The reaction mixture was washed with water, dried, and then the solvent was distilled off to yield the title compound (1.98 g, 5.75 mmol, yield 96%).

NMR (CDCl$_3$): 2.07 (3H, s), 3.70 (3H, s), 3,79 (3H, s), 3.92 (3H, s), 3.95 (3H, s), 4.07 (2H, s), 7.20 (2H, m), 7.99 (2H, m) FABMS (m/z): 346 (M+H)$^+$

Step 3. 4-(5,6-dimethoxy-3-methyl-1,4-benzoquinon-2-ylmethyl)benzoic Acid

The compound (1.98 g, 5.75 mmol) obtained in Step 2 was dissolved in a mixture of acetonitrile (40 ml) and water (15 ml), to which was added CAN (7.90 g, 14.5 mmol) and the mixture was stirred at room temperature for 40 minutes. The reaction mixture was poured into water and was extracted with ethyl acetate. After the extract was washed with water and dried, the solvent was distilled off. Ether was added to the residue and the resulting precipitate was filtered to yield the title compound (1.82 g, 5.76 mmol, yield 99%).

Method B

Step 1. p-iodobenzoic Acid Methylester p-iodobenzoic acid (500 mg, 2.02 mmol) was dissolved in methanol (30 ml), to which was added 2M trimethylsilyl diazomethane/hexane solution (13 ml) and the mixture was stirred at room temperature for 2 hours. The reaction mixture was concentrated under reduced pressure to yield a crude product (500 mg) of the title compound. This was used as a raw material in the subsequent reaction without purification.

NMR (CDCl$_3$): 3.91 (3H, s), 7.74 (2H, d, J=8.4 Hz), 7.80 (2H, d, J=8.5 Hz) FABMS (m/z): 263 (M+H)$^+$,

Step 2. 4-[hydroxy-(2,3,4,5-tetramethoxy-6-methylphenyl)methyl]benzoic Acid Methylester To a solution of zinc chloride (1.91 mmol) in dry tetrahydrofuran (9.6 ml) was added under ice-cooling a 1.4 M methyllithium/ether solution (4.1 ml, 5.73 mmol), and the mixture was stirred at 0° C. for 30 minutes. The reaction mixture was cooled to −78° C., to which was added a solution of the compound (500 mg, 1.91 mmol) obtained in Step 1 in dry tetrahydrofuran (2.0 ml) and the mixture was further stirred at −78° C. for 4 hours. Subsequently, a solution of 2,3,4,5-tetramethoxy-6-methylbenzaldehyde (1.38 g, 5.73 mmol) in dry tetrahydrofuran (2 ml) was added and the mixture was stirred overnight at room temperature. To the reaction mixture an aqueous solution of saturated ammonium chloride (2.5 ml) was added at 0° C. After concentrating under reduced pressure, the concentrate was diluted with water and extracted three times with chloroform. After the organic layer was dried, the solvent was distilled off. After purification by a silica gel column chromatography (ethyl acetate : hexane=1:2), the title compound (237 mg, 0.63 mmol, yield 33%) was obtained.

NMR (CDCl$_3$): 2.26 (3H, s), 3.28 (3H, s), 3,82 (3H, s), 3.85 (3H, s), 3.90 (3H, s), 3.94 (3H, s), 5.03 (1H, m), 6.01 (ii, d, J=10.5 Hz), 7.38 (2H, d, J=8.2 Hz), 7.99 (2H, d, J=8.4 Hz) FABMS (m/z): 376 (M+H)$^+$.

Step 3. 4-(2,3,4,5-tetramethoxy-6-methylbenzyl) benzoic Acid Methylester

To a solution of triethylsilane (88 mg, 0.76 mmol) and TMSOTf (0.004 ml) in methylene chloride (2 ml) was added dropwise a solution of the compound (237 mg, 0.63 mmol) obtained in Step 2 in methylene chloride (2 ml) and the mixture was stirred at room temperature for 4 hours. The reaction mixture was washed with saturated saline, dried, and then the solvent was distilled off. The residue was purified by a silica gel column chromatography (ethyl acetate:hexane=1:6) to yield the title compound (160 mg, 0.45 mmol, yield 71%).

NMR (CDCl$_3$): 2.06 (3H, s), 3.68 (3H, s), 3,78 (3H, s), 3.88 (3H, s), 3.92 (3H, s), 3.94 (3H, s), 4.05 (2H, s), 7.16 (2H, d, J=8.1 Hz), 7.91 (2H, d, J=8.1 Hz) FABMS (m/z): 360 (M+H)$^+$.

Step 4. 4-(2,3,4,5-tetramethoxy-6-methylbenzyl) benzoic Acid

The compound (160 mg, 0.45 mmol) obtained in Step 3 was dissolved in a mixture of an aqueous solution of potassium carbonate (91 mg, 0.66 mmol) in water (1 ml) and methanol (2 ml) and the mixture was stirred at 70° C. for 3 hours. The reaction mixture was acidified by adding concentrated hydrochloric acid and then was extracted with diethylether. The extract was washed with water, dried, and then the solvent was distilled off to yield the title compound (116 mg, 0.34 mmol, yield 76%).

Step 5. 4-(5,6-dimethoxy-3-methyl-1,4-benzoquinon-2-ylmethyl)benzoic Acid

The compound (116 mg, 0.34 mmol) obtained in Step 4 was dissolved in a mixture of acetonitrile (2.2 ml) and water (0.81 ml), to which was added CAN (447 mg, 0.82 mmol).

The mixture was stirred at room temperature for 30 minutes. The reaction mixture was poured into water and was extracted with methylene chloride. After the extract was washed with water and dried, the solvent was distilled off. The residue was purified by a silica gel column chromatography (methylene chloride:methanol=8:1) to yield the title compound (92 mg, 0.29 mmol, yield 85%).

Example 22

N-[4-(5,6-dimethoxy-3-methyl-1,4-benzoquinon-2-ylmethyl)benzoyl]morpholine

To 4-(5,6-dimethoxy-3-methyl-1,4-benzoquinon-2-ylmethyl)benzoic acid (100 mg, 0.31 mmol) obtained in Example 21 was added oxalyl chloride (0.3 ml) and the mixture was stirred at room temperature for 1 hour. After distilling off the solvent and drying under reduced pressure, an acid chloride was obtained which was dissolved in methylene chloride (2 ml). Morpholine (0.28 ml, 3.3 mmol) was added under ice-cooling and then the mixture was stirred at the same temperature for 30 minutes. The residue obtained after distilling off the solvent was purified by a silica gel column chromatography (hexane:ethyl acetate=1:5) to yield the title compound (56 mg, 0.15 mmol, yield 44%).

Example 23

N-[4-(5,6-dimethoxy-3-methyl-1,4-benzoquinon-2-ylmethyl)benzoyl]isopropylamine 4-(5,6-dimethoxy-3-methyl-1,4-benzoquinon-2-ylmethyl)benzoic acid (100 mg, 0.31 mmol) obtained in Example 21 and isopropylamine (0.28 ml, 3.3 mmol) were used, and a method similar to that described in Example 22 was employed to obtain the title compound (58 mg, 0.16 mmol, yield 49%).

Example 24

N-[4-(5,6-dimethoxy-3-methyl-1,4-benzoquinon-2-ylmethyl)benzoyl]piperidine

To a solution of 4-(5,6-dimethoxy-3-methyl-1,4-benzoquinon-2-ylmethyl)benzoic acid (50 mg, 0.16 mmol) obtained in Example 21 and piperidine (0.021 ml, 0.21 mmol) in methylene chloride (2 ml) was added 1-ethyl-3-(3-dimethylaminopropyl)carbodiimide hydrochloride (46 mg, 0.24 mmol), and then the mixture was stirred at room temperature for 1 hour. The reaction mixture was concentrated under reduced pressure and was purified by a silica gel column chromatography (hexane:ethyl acetate=1:2) to yield the title compound (30 mg, 0.08 mmol, yield 50%).

Example 25

N-[4-(5,6-dimethoxy-3-methyl-1,4-benzoquinon-2-ylmethyl)benzoyl]thiomorpholine 4-(5,6-dimethoxy-3-methyl-1,4-benzoquinon-2-ylmethyl)benzoic acid (100 mg, 0.32 mmol) obtained in Example 21 and thiomorpholine (0.035 ml, 0.35 mmol) were used, and a method similar to that described in Example 24 was employed to obtain the title compound (65 mg, 0.16 mmol, yield 51%).

Example 26

4-[4-(5,6-dimethoxy-3-methyl-1,4-benzoquinon-2-ylmethyl)phenyl]-n-butyric Acid

Method A

Step 1. 3-[4-(2,3,4,5-tetramethoxy-6-methylbenzyl)phenyl]propionic Acid Diazomethyl Ketone 3-[4-(2,3,4,5-tetramethoxy-6-methylbenzyl)phenyl] propionic acid (750 mg, 2.00 mmol) obtained in Step 6 of Example 1 was dissolved in methylene chloride (2 ml), to which was added oxalyl chloride (2 ml) and the mixture was stirred at room temperature for 1 hour. The acid chloride obtained after distilling off the solvent was dried under reduced pressure. To a diazomethane solution [prepared using p-toluenesulfonyl-N-methyl-N-nitrosoamide (8.6 g), potassium hydroxide (2.4 g), carbitol (14 ml), water (5 ml), and ether (100 ml)] was added under ice-cooling triethylamine (0.7 ml) and then an ether solution of the above acid chloride (10 ml) was added. The reaction mixture was stirred at the same temperature for 2 hours. After the solvent was distilled off, the residue was purified by a silica gel column chromatography (hexane ethyl acetate=2:1 to 1:1) to yield the title compound (380 mg, 0.98 mmol, yield 49%).

NMR (CDCl$_3$): 2.07 (3H, s), 2.60 (2H, m), 2.90 (2H, m), 3.69 (3H, s), 3.78 (3H, s), 3.91 (3H, s), 3.93 (3H, s), 3.97 (2H, s), 5.16 (1H, broad), 7.04 (4H, m) FABMS (m/z): 398 (M)$^+$.

Step 2. 4-[4-(2,3,4,5-tetramethoxy-6-methylbenzyl)phenyl]-n-butyric Acid

Sodium thiosulfate pentahydrate (230 mg, 0.93 mmol) and silver oxide (130 mg, 0.56 mmol) were dissolved in water (5 ml) and the mixture was heated to 50° C. to 70° C. A solution of the compound (380 mg, 0.98 mmol) obtained in Step 1 in dioxane (3.5 ml) was added dropwise, and the mixture was stirred at the same temperature for 10 minutes. The reaction mixture was cooled and was acidified with an aqueous solution of diluted nitric acid and then was extracted with ether. The extract was washed with water, dried, and then the solvent was distilled off to yield the title compound (210 mg, 0.54 mmol, yield 93%).

NMR (CDCl$_3$): 1.92 (2H, m), 2.08 (3H, s), 2.34 (2H, m), 2.61 (2H, m), 3.70 (6H, s), 3.78 (2H, s), 3.91 (3H, S), 3.93 (3H, s), 7.03 (4H, m) FABMS (m/z): 388 (M)$^+$.

Step 3. 4-[4-(5,6-dimethoxy-3-methyl-1,4-benzoquinon-2-ylmethyl)phenyl]-n-butyric Acid The compound (260 mg, 0.67 mmol) obtained in Step 2, acetonitrile (5 ml), water (1.6 ml), and CAN (920 mg, 1.70 mmol) were used, and a method similar to that described in Step 3 of Example 21 was employed and then the reaction mixture was purified by a silica gel column chromatography (methylene chloride:methanol=9:1) to yield the title compound (154 mg, 0.43 mmol, yield 74%).

Method B

Step 1. 3-[4-(5,6-dimethoxy-3-methyl-1,4-benzoquinon-2-ylmethyl)phenyl]propionic Acid Diazomethyl Ketone The 3-[4-(5,6-dimethoxy-3-methyl-1,4-benzoquinon-2-ylmethyl)phenyl]propionic acid (340 mg, 1.00 mmol) obtained in Step 7 of Example 1, oxalyl chloride (0.5 ml), and triethylamine (0.14 ml) were used, and a method similar to that described in Step 1 of Method A of Example 26 was employed to obtain the title compound (140 mg, 0.38 mmol, yield 38%).

NMR (CDCl$_3$): 2.07 (3H, s), 2.59 (2H, m), 2.90 (2H, m), 3.80 (2H, s), 3.98 (3H, s), 3.99 (3H, s), 5.17 (1H, broad), 7.08 (4H, s) FABMS (m/z): 369 (M+H)$^+$.

Step 2. 4-[4-(5,6-dimethoxy-3-methyl-1,4-benzoquinon-2-ylmethyl)phenyl]-n-butyric Acid The compound (70 mg, 0.20 mmol) obtained in Step 1, sodium thiosulfate pentahydrate (81 mg, 0.33 mmol), and silver oxide (44 mg, 0.19 mmol) were used, and a method similar to that described in Step 2 of Method A of Example 26 was employed to obtain the title compound (13 mg, 0.04 mmol, yield 20%).

Example 27

N-[4-[4-(5,6-dimethoxy-3-methyl-1,4-benzoquinon-2-ylmethyl)phenyl]butanoyl]morpholine 3-(4-(5,6-dimethoxy-3-methyl-1,4-benzoquinon-2-ylmethyl)phenyl]propionic acid diazomethyl ketone (70 mg, 0.20 mmol) obtained in Step 1 of Method B of Example 26 was dissolved in dry ethanol (5 ml), to which were added silver nitrate (34 mg, 0.20 mmol) and morpholine (0.090 ml, 1.0 mmol), and the mixture was heated to reflux for 20 minutes. The reaction mixture was filtered and the solid was washed with ethanol. The filtrate and the wash solution were combined and the solvent was distilled off, the resulting residue was purified by a silica gel column chromatography (hexane:ethyl acetate=1:3) to yield the title compound (42 mg, 0.098 mmol, yield 49%).

Example 28

N-[4-[4-(5,6-dimethoxy-3-methyl-1,4-benzoquinon-2-ylmethyl)phenyl]butanoyl]thiomorpholine 4-[4-(5,6-dimethoxy-3-methyl-1,4-benzoquinon-2-ylmethyl)phenyl]-n-butyric acid (50 mg, 0.14 mmol) obtained in Example 26 and thiomorpholine (0.016 ml, 0.15 mmol) were used, a method similar to that described in Example 24 was employed to obtain the title compound (15 mg, 0.034 mmol, yield 24%).

Example 29

N-[4-[4-(5,6-dimethoxy-3-methyl-1,4-benzoquinon-2-ylmethyl)phenyl]butanoyl]piperidine 4-[4-(5,6-dimethoxy-3-methyl-1,4-benzoquinon-2-ylmethyl)phenyl]-n-butyric acid (50 mg, 0.14 mmol) obtained in Example 26 and piperidine (0.015 ml, 0.15 mmol) were used, and a method similar to that described in Example 24 was employed to obtain the title compound (19 mg, 0.045 mmol, yield 32%).

Example 30

N-[4-[4-(5,6-dimethoxy-3-methyl-1,4-benzoquinon-2-ylmethyl)phenyl]butanoyl]isopropylamine 4-[4-(5,6-dimethoxy-3-methyl-1,4-benzoquinon-2-ylmethyl)phenyl]-n-butyric acid (50 mg, 0.14 mmol) obtained in Example 26 and isopropylamine (0.013 ml, 0.15 mmol) were used, and a method similar to that described in Example 24 was employed to obtain the title compound (30 mg, 0.075 mmol, yield 54%).

Example 31

3-[3-(5,6-dimethoxy-3-methyl-1,4-benzoquinon-2-ylmethyl)phenyl]propionic Acide 2,3,4,5-tetramethoxy-6-methylbenzaldehyde (960 mg, 4.00 mmol) and 2-(3-bromophenyl)-1,3-dioxolane (2.3 g, 10 mmol) were used, and a method similar to that described in Example 1 was employed to obtain the title compound (300 mg, 0.87 mmol).

Example 32

N-[3-[3-(5,6-dimethoxy-3-methyl-1,4-benzoquinon-2-ylmethyl)phenyl]propioyl]piperidine 3-[3-(5,6-dimethoxy-3-methyl-1,4-benzoquinon-2-ylmethyl)phenyl]propionic acid (65 mg, 0.19 mmol) obtained in Example 31 and piperidine (0.022 ml, 0.21 mmol) were used, and a method similar to that described in Example 24 was employed to obtain the title compound (27 mg, 0.066 mmol, yield 35%).

Example 33

N-[3-[3-(5,6-dimethoxy-3-methyl-1,4-benzoquinon-2-ylmethyl)phenyl]propioyl]thiomorpholine 3-[3-(5,6-dimethoxy-3-methyl-1,4-benzoquinon-2-ylmethyl)phenyl]propionic acid (65 mg, 0.19 mmol) obtained in Example 31 and thiomorpholine (0.022 ml, 0.21 mmol) were used, and a method similar to that described in Example 24 was employed to obtain the title compound (26 mg, 0.061 mmol, yield 32%).

Example 34

N-[3-[3-(5,6-dimethoxy-3-methyl-1,4-benzoquinon-2-ylmethyl)phenyl]propioyl]morpholine 3-[3-(5,6-dimethoxy-3-methyl-1,4-benzoquinon-2-ylmethyl)phenyl]propionic acid (65 mg, 0.19 mmol) obtained in Example 31 and morpholine (0.019 ml, 0.21 mmol) were used, and a method similar to that described in Example 24 was employed to obtain the title compound (29 mg, 0.069 mmol, yield 36%).

Example 35

N-[3-[3-(5,6-dimethoxy-3-methyl-1,4-benzoquinon-2-ylmethyl)phenyl]propioyl]isopropylamine 3-[3-(5,6-dimethoxy-3-methyl-1,4-benzoquinon-2-ylmethyl)phenyl]propionic acid (65 mg, 0.19 mmol) obtained in Example 31 and isopropylamine (0.019 ml, 0.21 mmol) were used, and a method similar to that described in Example 24 was employed to obtain the title compound (12 mg, 0.031 mmol, yield 16%).

Example 36

3-[3-(5,6-dimethoxy-3-methyl-1,4-benzoquinon-2-ylmethyl)phenyl]acrylic acid

3-[3-(2,3,4,5-tetramethoxy-6-methylbenzyl)phenyl] acrylic acid ethylester (360 mg, 0.75 mmol) was used, and a method similar to that described in Example 2 was employed to obtain the title compound (220 mg, 0.64 mmol).

Example 37

N-[3-[3-(5,6-dimethoxy-3-methyl-1,4-benzoquinon-2-ylmethyl)phenyl]acryloyl]piperidine 3-[3-(5,6-dimethoxy-3-methyl-1,4-benzoquinon-2-ylmethyl)phenyl]acrylic acid (55 mg, 0.16 mmol) obtained in Example 36 and piperidine (0.018 ml, 0.18 mmol) were used, and a method similar to that described in Example 24 was employed to obtain the title compound (30 mg, 0.073 mmol, yield 46%).

Example 38

N-[3-[3-(5,6-dimethoxy-3-methyl-1,4-benzoquinon-2-ylmethyl)phenyl]acryloyl]morpholine 3-[3-(5,6-dimethoxy-3-methyl-1,4-benzoquinon-2-ylmethyl)phenyl]acrylic acid (55 mg, 0.16 mmol) obtained in Example 36 and morpholine (0.016 ml, 0.18 mmol) were used, and a method similar to that described in Example 24 was employed to obtain the title compound (36 mg, 0.088 mmol, yield 55%).

Example 39

N-[3-[3-(5,6-dimethoxy-3-methyl-1,4-benzoquinon-2-ylmethyl)phenyl]acryloyl]isopropylamine 3-[3-(5,6-dimethoxy-3-methyl-1,4-benzoquinon-2-ylmethyl)phenyl]acrylic acid (55 mg, 0.16 mmol) obtained in Example 36 and isopropylamine (0.016 ml, 0.18 mmol) were used, and a method similar to that described in Example 24 was employed to obtain the title compound (21 mg, 0.055 mmol, yield 34%).

Example 40

N-[3-[3-(5,6-dimethoxy-3-methyl-1,4-benzoquinon-2-ylmethyl)phenyl]acryloyl]thiomorpholine 3-[3-(5,6-dimethoxy-3-methyl-1,4-benzoquinon-2-ylmethyl)phenyl]acrylic acid (55 mg, 0.16 mmol) obtained in Example 36 and thiomorpholine (0.018 ml, 0.18 mmol) were used, and a method similar to that described in Example 24 was employed to obtain the title compound (32 mg, 0.075 mmol, yield 47%).

Example 41

3-(5,6-dimethoxy-3-methyl-1,4-benzoquinon-2-ylmethyl)benzoic acid

Step 1. m-iodobenzoic Acid Methylester m-iodobenzoic acid (1 g, 4.03 mmol) was used, and a method similar to that described in Step 1 of Method B of Example 21 was employed to obtain the title compound as a crude product (1.08 g). This was used as a raw material for the subsequent reaction without purification.

NMR (CDCl$_3$): 3.92 (3H, s), 7.18 (1H, m), 7,88 (1H, d, J=8.0 Hz), 8.00 (1H, d, J=7.8 Hz), 8.38 (1H, s) FABMS (m/z): 263 (M+H)$^+$.

Step 2. 3-[hydroxy-(2,3,4,5-tetramethoxy-6-methylphenyl)methyl]benzoic Acid Methylester
Method 1
The compound (1.08 g, 4.1 mmol) obtained in Step 1 was used, and a method similar to that described in Step 2 of Method B of Example 21 was employed to obtain the title compound (490 mg, 1.30 mmol, yield 32%).

NMR (CDCl$_3$): 2.26 (3H, s), 3.32 (3H, s), 3.82 (3H, s), 3.86 (3H, s), 3.90 (3H, s), 3.94 (3H, s), 6.02 (1H, d, J=10.6 Hz), 7.39 (1H, m), 7.47 (1H, d, J=7.6 Hz), 7.91 (1H, J=7.4 Hz), 8.04 (1H, s) FABMS (m/z): 376 (M+H)$^+$.
Method 2
A 1.54 M solution of t-butyllithium/pentane and the compound (1.05 g, 4.00 mmol) obtained in Step 1 were used, and a method similar to that described in Step 2 of Method B of Example 21 was employed to obtain the title compound (684 mg, 1.28 mmol, yield 32%).

Step 3. 3-(2,3,4,5-tetramethoxy-6-methylbenzyl)benzoic Acid Methylester

The compound (245 mg, 0.65 mmol) obtained in Step 2 was used, and a method similar to that described in Step 3 of Method B of Example 21 was employed to obtain the title compound (170 mg, 0.47 mmol, yield 72%).

NMR (CDCl$_3$): 2.08 (3H, s), 3.70 (3H, s), 3.78 (3H, s), 3.89 (3H, s), 3.92 (3H, s), 3.94 (3H, s), 4.05 (2H, s), 7.26–7.32 (2H, m), 7.83 (2H, m) FABMS (m/z): 360 (M+H)$^+$,

Step 4. 3-(2,3,4,5-tetramethoxy-6-methylbenzyl)benzoic Acid

The compound (170 mg, 0.47 mmol) obtained in Step 3 was used, and a method similar to that described in Step 4 of Method B of Example 21 was employed to obtain the title compound (150 mg, 0.43 mmol, yield 91%).

NMR (CDCl$_3$): 2.09 (3H, s), 3.71 (3H, s), 3.79 (3H, s), 3.92 (3H, s), 3.94 (3H, s), 4.06 (2H, s), 7.33 (2H, m), 7.90 (2H, m) FABMS (m/z): 346 (M+H)$^+$

Step 5. 3-(5,6-dimethoxy-3-methyl-1,4-benzoquinon-2-ylmethyl)benzoic Acid

The compound (150 mg, 0.43 mmol) obtained in Step 4 was used, and a method similar to that described in Step 5 of Method B of Example 21 was employed to obtain the title compound (117 mg, 0.37 mmol, yield 86%).

Example 42

N-[3-(5,6-dimethoxy-3-methyl-1,4-benzoquinon-2-ylmethyl)benzoyl]isopropylamine 3-(5,6-dimethoxy-3-methyl-1,4-benzoquinon-2-ylmethyl)benzoic acid (85 mg, 0.27 mmol) obtained in Example 41, isopropylamine (0.035 ml, 0.41 mmol), and 1-ethyl-3-(3-dimethylaminopropyl)carbodiimide hydrochloride (78 mg, 0.41 mmol) in dry methylene chloride (3.4 ml) were stirred at room temperature for 1 hour. The reaction mixture was concentrated under reduced pressure and then was purified by a silica gel column chromatography (methylene chloride:methanol=20:1) to obtain the title compound (37 mg, 0.10 mmol, yield 37%).

Example 43

N-[3-(5,6-dimethoxy-3-methyl-1,4-benzoquinon-2-ylmethyl)piperidine 3-(5,6-dimethoxy-3-methyl-1,4-benzoquinon-2-ylmethyl)benzoic acid (85 mg, 0.27 mmol) obtained in Example 41 and piperidine (0.036 ml, 0.41 mmol) were used, and a method similar to that described in Example 42 was employed to obtain the title compound (40 mg, 0.10 mmol, yield 37%).

Example 44

N-[3-(5,6-dimethoxy-3-methyl-1,4-benzoquinon-2-ylmethyl)morpholine 3-(5,6-dimethoxy-3-methyl-1,4-benzoquinon-2-ylmethyl)benzoic acid (85 mg, 0.27 mmol) obtained in Example 41 and morpholine (0.036 ml, 0.41 mmol) were used, and a method similar to that described in Example 42 was employed to obtain the title compound (57 mg, 0.15 mmol, yield 54%).

Example 45

N-[3-(5,6-dimethoxy-3-methyl-1,4-benzoquinon-2-ylmethyl)thiomorpholine 3-(5,6-dimethoxy-3-methyl-1,4-benzoquinon-2-ylmethyl)benzoic acid (85 mg, 0.27 mmol) obtained in Example 41 and thiomorpholine (0.041 ml, 0.41 mmol) were used, and a method similar to that described in Example 42 was employed to obtain the title compound (61 mg, 0.15 mmol, yield 54%).

Example 46

N-[3-[4-(3,5,6-trimethyl-1,4-benzoquinon-2-ylmethyl)phenyl]propionyl]isopropylamine 3-[4-(3,5,6-trimethyl-1,4-benzoquinon-2-ylmethyl) phenyl]propionic acid (25 mg, 0.08 mmol), isopropylamine (0.010 ml, 0.12 mmol), and 1-ethyl-3-(3-dimethylaminopropyl)carbodiimide hydrochloride (28 mg, 0.12 mmol) in dry methylene chloride (1 ml) were stirred at room temperature for 1 hour. The reaction mixture was concentrated under reduced pressure and was purified by a silica gel column chromatography (methylene chloride:ethyl acetate=4:1) to obtain the title compound (18 mg, 0.051 mmol, yield 64%).

Example 47

N-[3-[4-(3,5,6-trimethyl-1,4-benzoquinon-2-ylmethyl)phenyl]propionyl]piperidine

3-[4-(3,5,6-trimethyl-1,4-benzoquinon-2-ylmethyl) phenyl]propionic acid (25 mg, 0.08 mmol) and piperidine (0.012 ml, 0.12 mmol) were used, and a method similar to that described in Example 46 was employed to obtain the title compound (53 mg, 0.14 mmol, yield 59%).

Example 48

N-[3-[4-(3,5,6-trimethyl-1,4-benzoquinon-2-ylmethyl)phenyl]propionyl]morpholine

3-[4-(3,5,6-trimethyl-1,4-benzoquinon-2-ylmethyl) phenyl]propionic acid (25 mg, 0.08 mmol) and morpholine (0.010 ml, 0.12 mmol) were used, and a method similar to that described in Example 46 was employed to obtain the title compound (21 mg, 0.055 mmol, yield 69%).

Example 49

N-[3-[3-(3,5,6-trimethyl-1,4-benzoquinon-2-ylmethyl)phenyl]propionyl]isopropylamine 3-[3-(5,6-dimethoxy-3-methyl-1,4-benzoquinon-2-ylmethyl)phenyl]propionic acid (30 mg, 0.096 mmol) and isopropylamine (0.010 ml, 0.12 mmol) were used, and a method similar to that described in Example 46 was employed to obtain the title compound (14 mg, 0.040 mmol, yield 42%).

Example 50

N-[3-[3-(3,5,6-trimethyl-1,4-benzoquinon-2-ylmethyl)phenyl]propionyl]piperidine

3-[3-(5,6-dimethoxy-3-methyl-1,4-benzoquinon-2-ylmethyl)phenyl]propionic acid (30 mg, 0.096 mmol) and piperidine (0.010 ml, 0.12 mmol) were used, and a method similar to that described in Example 46 was employed to obtain the title compound (19 mg, 0.050 mmol, yield 52%).

Example 51

N-[3-[3-(3,5,6-trimethyl-1,4-benzoquinon-2-ylmethyl)phenyl]propionyl]morpholine

3-[3-(5,6-dimethoxy-3-methyl-1,4-benzoquinon-2-ylmethyl)phenyl]propionic acid (30 mg, 0.096 mmol) and morpholine (0.010 ml, 0.12 mmol) were used, and a method similar to that described in Example 46 was employed to obtain the title compound (25 mg, 0.066 mmol, yield 69%).

Example 52

4-(5,6-dimethoxy-3-methyl-1,4-benzoquinon-2-ylmethyl)phenylacetic Acid

Step 1. 4-(2,3,4,5-tetramethoxy-6-methylbenzyl) benzoic Acid Diazomethyl Ketone 4-(2,3,4,5-tetramethoxy-6-methylbenzyl)benzoic acid (700 mg, 2.02 mmol) obtained in Step 2 of Method A of Example 21 was used, and a method similar to that described in Step 1 of Method A of Example 26 was employed to obtain the title compound (96 mg, 0.26 mmol, yield).

NMR (CDCl$_3$): 2.07 (3H, s), 3.70 (3H, s), 3.79 (3H, s), 3.92 (3H, s), 3.95 (3H, s), 4.05 (2H, s), 5.85 (1H, s), 7.18 (2H, d, J=8.0 Hz), 7.65 (2H, d, J=8.0 Hz) FABMS (m/z): 370 (M)$^+$.

Step 2. 4-(5,6-dimethoxy-3-methyl-1,4-benzoquinon-2-ylmethyl)phenylacetic Acid

The compound (96 mg, 0.26 mmol) obtained in Step 1 was used, and a method similar to that described in Step 2 of Method A of Example 26 was employed to obtain 4-(2,3,4,5-tetramethoxy-6-methylbenzyl)phenylacetic acid as a crude product. This was used without further purification, and a method similar to that described in Step 3 of Method A of Example 26 was employed to obtain the title compound (63 mg, 0.19 mmol).

Example 53

N-[4-(5,6-dimethoxy-3-methyl-1,4-benzoquinon-2-ylmethyl)phenylacetyl]morpholine 4-(5,6-dimethoxy-3-methyl-1,4-benzoquinon-2-ylmethyl)benzoic acid (100 mg, 0.32 mmol) obtained in Example 21 was used, and a method similar to that described in Step 1 of Method A of Example 26 was employed to obtain 4-(5,6-dimethoxy-3-methyl-1,4-benzoquinon-2-ylmethyl)benzoic acid diazomethyl ketone as a crude product. Without further purification, this was dissolved in dry ethanol (5 ml). Silver nitrate (56 mg, 0.33 mmol) and morpholine (0.14 ml, 1.65 mmol) were added thereto and the mixture was heated to reflux for one hour. The resulting residue obtained after the distilling off the solvent was purified by a silica gel column chromatography (hexane:ethyl acetate=1:3 to 1:4) to yield a crude fraction containing the title compound. The fraction was purified again by silica gel column chromatography (methylene chloride:methanol=20:1) to obtain the title compound (9 mg, 0.02 mmol, yield 7%).

Example 54

N-[4-(5,6-dimethoxy-3-methyl-1,4-benzoquinon-2-ylmethyl)phenylacetyl]piperidine 4-(5,6-dimethoxy-3-methyl-1,4-benzoquinon-2-ylmethyl)phenylacetic acid (21 mg, 0.063 mmol) obtained in Example 52 and piperidine (0.0094 ml, 0.095 mmol) were used, and a method similar to that described in Example 46 was employed to obtain the title compound (7.8 mg, 0.020 mmol, yield 32%).

Example 55

N-[4-(5,6-dimethoxy-3-methyl-1,4-benzoquinon-2-ylmethyl)phenylacetyl]thiomorpholine 4-(5,6-dimethoxy-3-methyl-1,4-benzoquinon-2-ylmethyl)phenylacetic acid (21 mg, 0.063 mmol) obtained in Example 52 and thiomorpholine (0.0096 ml, 0.095 mmol) were used, and a method similar to that described in Example 46 was employed to obtain the title compound (5.1 mg, 0.012 mmol, yield 19%).

Example 56

N-[4-(5,6-dimethoxy-3-methyl-1,4-benzoquinon-2-ylmethyl)phenylacetyl]isopropylamine 4-(5,6-dimethoxy-3-methyl-1,4-benzoquinon-2-ylmethyl)phenylacetic acid (21 mg, 0.063 mmol) obtained in Example 52 and isopropylamine (0.008 ml, 0.095 mmol) were used, and a method similar to that described in Example 46 was employed to obtain the title compound (5.1 mg, 0.014 mmol, yield 22%).

Example 57

3-(5,6-dimethoxy-3-methyl-1,4-benzoquinon-2-ylmethyl)phenylacetic acid

Step 1. 3-(2,3,4,5-tetramethoxy-6-methylbenzyl)benzoic Acid Diazomethyl Ketone 3-(2,3,4,5-tetramethoxy-6-methylbenzyl)benzoic acid (560 mg, 1.6 mmol) obtained in Step 4 of Example 41 was used, and a method similar to that described in Step 1 of Method A of Example 26 was employed to obtain the title compound (410 mg, 1.1 mmol, yield 69%).

NMR (CDCl$_3$): 2.08 (3H, s), 3.71 (3H, s), 3.78 (3H, s), 3.93 (3H, s), 3.94 (3H, s), 4.05 (2H, s), 5.84 (1H, s), 7.26 (1H, m), 7.32 (1H, m), 7.53 (1H, m), 7.58 (1H, m) FABMS (m/z): 370 (M)$^+$.

Step 2. 3-(2,3,4,5-tetramethoxy-6-methylbenzyl)phenylacetic Acid

The compound (410 mg, 1.11 mmol) obtained in Step 1 was used, and a method similar to that described in Step 2 of Method A of Example 26 was employed to obtain the title compound (370 mg, 1.03 mmol, yield 93%).

NMR (CDCl$_3$): 2.08 (3H, s), 3.60 (2H, s), 3.68 (3H, s), 3.78 (3H, s), 3.92 (3H, s), 3.94 (3H, s), 4.00 (2H, s), 6.99–7.09 (3H, m), 7.21 (1H, m) FABMS (m/z): 360 (M)$^+$.

Step 3. 3-(5,6-dimethoxy-3-methyl-1,4-benzoquinon-2-ylmethyl)phenylacetic Acid The compound (370 mg, 1.03 mmol) obtained in Step 2 was used, and a method similar to that described in Step 3 of Method A of Example 26 was employed to obtain the title compound (330 mg, 1.00 mmol, yield 97%).

Example 58

N-[3-(5,6-dimethoxy-3-methyl-1,4-benzoquinon-2-ylmethyl)phenylacetyl]piperidine 3-(5,6-dimethoxy-3-methyl-1,4-benzoquinon-2-ylmethyl)phenylacetic acid (90 mg, 0.27 mmol) obtained in Example 57 and piperidine (0.040 ml, 0.41 mmol) were used, and a method similar to that described in Example 46 was employed to obtain the title compound (35 mg, 0.088 mmol, yield 33%).

Example 59

N-[3-(5,6-dimethoxy-3-methyl-1,4-benzoquinon-2-ylmethyl)phenylacetyl]thiomorpholine 3-(5,6-dimethoxy-3-methyl-1,4-benzoquinon-2-ylmethyl)phenylacetic acid (90 mg, 0.27 mmol) obtained in Example 57 and thiomorpholine (0.040 ml, 0.41 mmol) were used, and a method similar to that described in Example 46 was employed to obtain the title compound (47 mg, 0.11 mmol, yield 41%).

Example 60

N-[3-(5,6-dimethoxy-3-methyl-1,4-benzoquinon-2-ylmethyl)phenylacetyl]morpholine 3-(5,6-dimethoxy-3-methyl-1,4-benzoquinon-2-ylmethyl)phenylacetic acid (90 mg, 0.27 mmol) obtained in Example 57 and morpholine (0.035 ml, 0.41 mmol) were used, and a method similar to that described in Example 46 was employed to obtain the title compound (41 mg, 0.10 mmol, yield 37%).

Example 61

N-[3-(5,6-dimethoxy-3-methyl-1,4-benzoquinon-2-ylmethyl)-phenylacetyl]isopropylamine 3-(5,6-dimethoxy-3-methyl-1,4-benzoquinon-2-ylmethyl)phenylacetic acid (90 mg, 0.27 mmol) obtained in Example 57 and isopropylamine (0.035 ml, 0.41 mmol) were used, and a method similar to that described in Example 46 was employed to obtain the title compound (43 mg, 0.12 mmol, yield 44%).

Example 62

4-[3-(5,6-dimethoxy-3-methyl-1,4-benzoquinon-2-ylmethyl)phenyl]-n-butyric Acid

Step 1. 3-[3-(2,3,4,5-tetramethoxy-6-methylbenzyl)phenyl]propionic Acid Diazomethyl Ketone 3-[3-(2,3,4,5-tetramethoxy-6-methylbenzyl)phenyl]propionic acid (500 mg, 1.34 mmol) obtained as an intermediate in the synthesis of the compound of Example 31 was used, and a method similar to that described in Step 1 of Method A of Example 26 was employed to obtain the title compound (330 mg, 0.83 mmol, yield 62%).

NMR (CDCl$_3$): 2.07 (3H, s), 2.58 (2H, broad), 2.89 (2H, m), 3.65 (3H, s), 3.78 (3H, s), 3.93 (3H, s), 3.94 (3H, s), 3.98

(2H, s), 5.17 (1H, broad), 6.91–6.99 (3H, m), 7.16 (1H, m) FABMS (m/z): 398 (M)$^+$.

Step 2. 4-[3-(2,3,4,5-tetramethoxy-6-methylbenzyl) phenyl]-n-butyric Acid

The compound (330 mg, 0.83 mmol) obtained in Step 1 was used, and a method similar to that described in Step 2 of Method A of Example 26 was employed to obtain the title compound (320 mg, 0.83 mmol, yield 100%).

NMR (CDCl$_3$): 1.93 (2H, m), 2.08 (3H, s), 2.35 (2H, m), 2.62 (2H, m), 3.69 (3H, s), 3.78 (3H, S), 3.92 (3H, s), 3.94 (3H, s), 3.99 (2H, s), 6.91–6.98 (3H, m), 7.16 (1H, m) FABMS (m/z): 388 (M)$^+$,

Step 3. 4-[3-(5,6-dimethoxy-3-methyl-1,4-benzoquinon-2-ylmethyl)phenyl]-n-butyric Acid The compound (330 mg, 0.85 mmol) obtained in Step 2 was used, and a method similar to that described in Step 3 of Method A of Example 26 was employed to obtain the title compound (290 mg, 0.81 mmol, yield 98%).

Example 63

N-[4-[3-(5,6-dimethoxy-3-methyl-1,4-benzoquinon-2-ylmethyl)phenyl]butanoyl]piperidine 4-[3-(5,6-dimethoxy-3-methyl-1,4-benzoquinon-2-ylmethyl)phenyl]-n-butyric acid (73 mg, 0.20 mmol) obtained in Example 62 and piperidine (0.030 ml, 0.30 mmol) were used, and a method similar to that described in Example 46 was employed to obtain the title compound (16 mg, 0.038 mmol, yield 19%).

Example 64

N-[4-[3-(5,6-dimethoxy-3-methyl-1,4-benzoquinon-2-ylmethyl)phenyl]butanoyl]thiomorpholine 4-[3-(5,6-dimethoxy-3-methyl-1,4-benzoquinon-2-ylmethyl)phenyl]-n-butyric acid (73 mg, 0.20 mmol) obtained in Example 62 and thiomorpholine (0.030 ml, 0.30 mmol) were used, and a method similar to that described in Example 46 was employed to obtain the title compound (26 mg, 0.059 mmol, yield 29%).

Example 65

N-[4-[3-(5,6-dimethoxy-3-methyl-1,4-benzoquinon-2-ylmethyl)phenyl]butanoyl]morpholine 4-[3-(5,6-dimethoxy-3-methyl-1,4-benzoquinon-2-ylmethyl)phenyl]-n-butyric acid (73 mg, 0.20 mmol) obtained in Example 62 and morpholine (0.026 ml, 0.30 mmol) were used, and a method similar to that described in Example 46 was employed to obtain the title compound (28 mg, 0.066 mmol, yield 33%).

Example 66

N-[4-[3-(5,6-dimethoxy-3-methyl-1,4-benzoquinon-2-ylmethyl)phenyl]butanoyl]isopropylamine 4-[3-(5,6-dimethoxy-3-methyl-1,4-benzoquinon-2-ylmethyl)phenyl]-n-butyric acid (73 mg, 0.20 mmol) obtained in Example 62 and isopropylamine (0.019 ml, 0.30 mmol) were used, and a method similar to that described in Example 46 was employed to obtain the title compound (17 mg, 0.043 mmol, yield 21%).

Example 67

3-[2-(5,6-dimethoxy-3-methyl-1,4-benzoquinon-2-ylmethyl)phenyl]acrylic Acid

Step 1. 2-[2-[hydroxy-(2,3,4,5-tetramethoxy-6-methylphenyl)methyl]phenyl]-1,3-dioxolane 2-(2-bromophenyl)-1,3-dioxolane (2.03 g, 8.90 mmol) was used, and a method similar to that described in Step 1 of Example 1 was employed to obtain the title compound (1.64 g, 4.20 mmol, yield 47%).

NMR (CDCl$_3$): 2.14 (3H, s), 3.64 (3H, s), 3.79 (3H, s), 3.90 (3H, s), 3.96 (3H, s), 4.08–4.19 (2H, m), 4.43 (1H, d, J=8.8 Hz), 6.37 (1H, s), 6.46 (1H, d, J=8.8 Hz), 6.97 (1H, d, J=7.6 Hz), 7.24–7.30 (2H, m), 7.70 (1H, d, J=7.6 Hz) FABMS (m/z): 390 (M+H)$^+$,

Step 2. 2-[2-[acetoxy-(2,3,4,5-tetramethoxy-6-methylphenyl methyl]benzaldehyde

The compound (640 mg, 1.64 mmol) obtained in Step 1 was used, and a method similar to that described in Step 2 of Example 1 was employed to obtain the title compound (590 mg, 1.51 mmol, yield 92%).

NMR (CDCl$_3$): 2.15 (3H, s), 2.17 (3H, s), 3.64 (3H, s), 3.79 (3H, s), 3.87 (3H, s), 3.95 (3H, s), 7.33 (1H, d, J=7.7 Hz), 7.45 (1H, m), 7.53 (1H, m), 7.88 (1H, m), 7.94 (1H, s), 10.20 (1H, s) FABMS (m/z): 388 (M+H)$^+$.

Step 3. 3-[2-[acetoxy-(2,3,4,5-tetramethoxy-6-methylphenyl)methyl]phenyl]acrylic Acid Ethylester The compound (590 mg, 1.51 mmol) obtained in Step 2 was used, and a method similar to that described in Step 3 of Example 1 was employed to obtain the title compound (490 mg, 1.07 mmol, yield 71%).

NMR (CDCl$_3$): 1.32 (3H, s), 2.15 (3H, s), 2.21 (3H, s), 3.58 (3H, s), 3.78 (3H, s), 3.86 (3H, s), 3.94 (3H, s), 4.22 (2H, m), 6.19 (1H, d, J=15.7 Hz), 7.24–7.33 (2H, m), 7.49 (1H, m), 7.60 (1H, s), 7.80 (1H, d, J=15.7 Hz) FABMS (m/z): 458 (M+H)$^+$.

Step 4. 3-[2-(2,3,4,5-tetramethoxy-6-methylbenzyl) phenyl]acrylic Acid Ethylester The compound (490 mg, 1.07 mmol) obtained in Step 3 was used, and a method similar to that described in Step 4 of Example 1 was employed to obtain the title compound (230 mg, 0.58 mmol, yield 54%).

NMR (CDCl$_3$): 1.36 (3H, m), 2.00 (3H, s), 3.64 (3H, s), 3.80 (3H, s), 3.92 (3H, s), 3.96 (3H, s), 4.11 (2H, S), 4.29 (2H, m), 6.40 (1H, d, J=15.8 Hz), 6.71 (1H, broad), 7.19 (2H, m), 7.59 (1H, m), 8.22 (1H, d, J=15.8 Hz) FABMS (m/z): 400 (M+H)$^+$.

Step 5. 3-[2-(2,3,4,5-tetramethoxy-6-methylbenzyl) phenyl]acrylic Acid

The compound (137 mg, 0.34 mmol) obtained in Step 4 was used, and a method similar to that described in Step 1 of Example 2 was employed to obtain the title compound (71 mg, 0.19 mmol, yield 56%).

NMR (CDCl$_3$): 2.02 (3H, s), 3.64 (3H, s), 3.80 (3H, s), 3.92 (3H, s), 3.96 (3H, s), 4.12 (2H, s), 6.42 (1H, d, J=15.8 Hz), 6.75 (1H, m), 7.21–7.25 (2H, m), 7.60 (1H, m), 8.32 (1H, d, J=15.8 Hz) FABMS (m/z): 372 (M+H)$^+$.

Step 6. 3-[2-(5,6-dimethoxy-3-methyl-1,4-benzoquinon-2-ylmethyl)phenyl]acrylic Acid The compound (71 mg, 0.34 mmol) obtained in Step 5 was used, and a method similar to that described in Step 2 of Example 2 was employed to obtain the title compound (23 mg, 0.067 mmol, yield 35%).

Example 68

N-[3-[2-(5,6-dimethoxy-3-methyl-1,4-benzoquinon-2-ylmethyl)phenyl]acryloyl]thiomorpholine 3-[2-(5,6-dimethoxy-3-methyl-1,4-benzoquinon-2-ylmethyl)phenyl]acrylic acid (20 mg, 0.058 mmol) obtained in Example 67 and thiomorpholine (0.009 ml, 0.087 mmol) were used, and a method similar to that described in Example 46 was employed to obtain the title compound (10 mg, 0.023 mmol, yield 40%).

Example 69

3-[2-(5,6-dimethoxy-3-methyl-1,4-benzoquinon-2-ylmethyl)phenyl]propionic Acid

Step 1. 3-[2-[(2,3,4,5-tetramethoxy-6-methylbenzyl)phenyl]propionic Acid Ethylester 3-[2-(2,3,4,5-tetramethoxy-6-methylbenzyl)phenyl]acrylic acid ethylester (85 mg, 0.21 mmol) obtained in Step 4 of Example 67 was used, and a method similar to that described in Step 5 of Example 1 was employed to obtain the title compound (80 mg, 0.20 mmol, yield 95%).

NMR (CDCl$_3$): 1.27 (3H, m), 2.03 (3H, s), 2.68 (2H, m), 3.11 (2H, m), 3.61 (3H, m), 3.81 (3H, s), 3.92 (3H, s), 3.96 (3H, s), 3.98 (2H, 9), 4.17 (2H, m), 6.63 (1H, d, J=7.6 HZ), 7.04 (1H, m), 7.11 (1H, m), 7.18 (1H, m) FABMS (m/z): 402 (M+H)+.

Step 2. 3-[2-(2,3,4,5-tetramethoxy-6-methylbenzyl)phenyl]propionic Acid

The compound (80 mg, 0.20 mmol) obtained in Step 1 was used, and a method similar to that described in Step 6 of Example 1 was employed to obtain the title compound (63 mg, 0.17 mmol, yield 85%).

NMR (CDCl$_3$): 2.03 (3H, s), 2.75 (2H, m), 3.12 (2H, m), 3.61 (3H, s), 3.81 (3H, s), 3.91 (3H, s), 3.96 (3H, s), 3.98 (2H, s), 6.65 (1H, d, J=7.6 Hz), 7.06 (1H, m), 7.13 (1H, m), 7.20 (1H, d, J=7.2 HZ) FABMS (m/z): 374 (M+H)$^+$.

Step 3. 3-[2-(5,6-dimethoxy-3-methyl-1,4-benzoquinon-2-ylmethyl)phenyl]propionic Acid The compound (63 mg, 0.17 mmol) obtained in Step 2 was used, and a method similar to that described in Step of Example 1 was employed to obtain the title compound (50 mg, 0.15 mmol, yield 88%).

Example 70

N-[3-[2-(5,6-dimethoxy-3-methyl-1,4-benzoquinon-2-ylmethyl)phenyl]propionyl]piperidine 3-[2-(5,6-dimethoxy-3-methyl-1,4-benzoquinon-2-ylmethyl)phenyl]propionic acid (20 mg, 0.058 mmol) obtained in Example 69 and piperidine (0.009 ml, 0.087 mmol) were used, and a method similar to that described in Example 46 was employed to obtain the title compound (8.4 mg, 0.020 mmol, yield 34%).

Example 71

N-[3-[2-(5,6-dimethoxy-3-methyl-1,4-benzoquinon-2-ylmethyl)phenyl]propionyl]morpholine 3-[2-(5,6-dimethoxy-3-methyl-1,4-benzoquinon-2-ylmethyl)phenyl]propionic acid (25 mg, 0.070 mmol) obtained in Example 69 and morpholine (0.009 ml, 0.11 mmol) were used, and a method similar to that described in Example 46 was employed to obtain the title compound (10 mg, 0.024 mmol, yield 34%).

Example 72

N-[3-[2-(5,6-dimethoxy-3-methyl-1,4-benzoquinon-2-ylmethyl)phenyl]propionyl]thiomorpholine 3-[2-(5,6-dimethoxy-3-methyl-1,4-benzoquinon-2-ylmethyl)phenyl]propionic acid (25 mg, 0.070 mmol) obtained in Example 69 and thiomorpholine (0.011 ml, 0.11 mmol) were used, and a method similar to that described in Example 46 was employed to obtain the title compound (10 mg, 0.024 mmol, yield 34%).

Example 73

N-[3-[2-(5,6-dimethoxy-3-methyl-1,4-benzoquinon-2-ylmethyl)phenyl]propionyl]isopropylamine 3-[2-(5,6-dimethoxy-3-methyl-1,4-benzoquinon-2-ylmethyl)phenyl]propionic acid (15 mg, 0.044 mmol) obtained in Example 69 and isopropylamine (0.005 ml, 0.066 mmol) were used, and a method similar to that described in Example 46 was employed to obtain the title compound (4.7 mg, 0.012 mmol, yield 27%).

Example 74 to 189

The compounds of Example 74 to 189 were prepared using a synthesizer (MORITEX Corp.) in the following method:

To a solution of 3-[4-(5,6-dimethoxy-3-methyl-1,4-benzoquinon-2-ylmethyl)phenyl]propionic acid (100 mg, 0.30 mmol) obtained in Example 1 in dry methylene chloride (0.3 ml) were sequentially added triethylamine (0.2 ml, 1.40 mmol), a solution of an amine (0.4 mmol) in methylene chloride (0.6 ml) and propane phosphonic acid anhydride (a 25% solution in ethyl acetate, 0.6 ml), and the mixture was stirred at 25° C. for 1 to 2 hours. Water was added to the reaction mixture, extracted with ethyl acetate, and after drying the solvent was distilled off. The resulting residue was purified by a silica gel column chromatography (methylene chloride-methanol) to yield the desired compound.

| Ex. No. | Structure | Property (mp °C.) | FABMS (m/z) | NMR(CDCl$_3$, δ) |
|---|---|---|---|---|
| 1 | 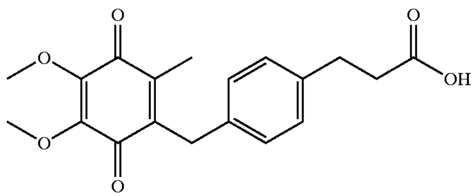 | crystal (139–141) | 344(M)$^+$(EIMS) | 2.09(3H, s), 2.62(2H, m), 2.89(2H, m), 3.80(2H, s), 3.99(6H, s), 6.95–7.30(4H, m) |
| 2 | 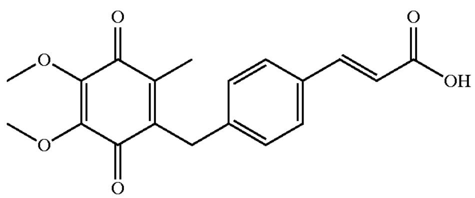 | crystal (203–205) | 343(M+H)$^+$ | 2.09(3H, s), 3.87(2H, s), 4.00(6H, s), 6.39(1H, d), 7.22(2H, d), 7.47(2H, d), 7.73(1H, d) |
| 3 | 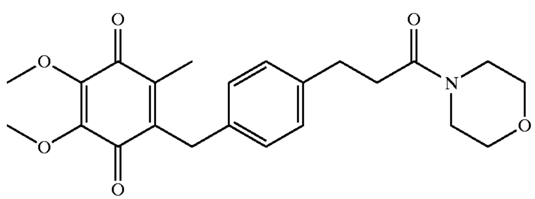 | crystal (65–67) | 414(M+H)$^+$ | 2.08(3H, s), 2.57(2H, m), 2.93(2H, m), 3.30–3.40(2H, m), 3.45–3.55(2H, m), 3.55–3.65(4H, m), 3.81(2H, s), 3.98(3H, s), 3.99(3H, s), 7.10(4H, s) |
| 4 | 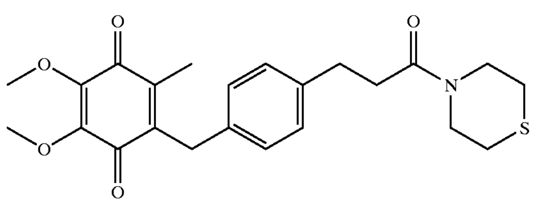 | crystal (65–67) | 429(M)$^+$(EIMS) | 2.09(3H, s), 2.25–2.65(4H, m), 2.57(2H, m), 2.91(2H, m), 3.55–4.95(2H, m), 3.81(2H, s), 3.99(6H, s), 7.12(4H, s) |

| No. | Structure | State (mp °C) | MS | NMR |
|---|---|---|---|---|
| 5 | (quinone-CH2-C6H4-CH2CH2-C(O)-N-thiomorpholine S-oxide) | crystal (114–116) | 446(M+H)+ | 2.09(3H, s), 2.10–2.20(1H, m), 2.50–2.70(4H, m), 2.70–2.85(1H, m), 2.85–3.00(2H, m), 3.60–3.80(2H, m), 3.80(2H, s), 3.98(3H, s), 3.99(3H, s), 3.95–4.10(1H, m), 4.40–4.55(1H, m), 7.12(4H, s) |
| 6 | (quinone-CH2-C6H4-CH2CH2-C(O)-N-thiomorpholine S,S-dioxide) | crystal (104–105) | 462(M+H)+ | 2.10(3H, s), 2.50–2.70(4H, m), 2.85–3.00(4H, m), 3.70–3.90(4H, m), 3.98(3H, s), 3.99(3H, s), 4.00–4.15(2H, m), 7.00–7.20(4H, m) |
| 7 | (quinone-CH2-C6H4-CH2CH2-C(O)-N-piperidine) | crystal (63–64) | 412(M+H)+ | 1.52(6H, m), 2.07(3H, s), 2.56(2H, m), 2.91(2H, m), 3.32(2H, m), 3.54(2H, m), 3.80(2H, s), 3.98(3H, s), 3.99(3H, s), 7.10(4H, m) |
| 8 | (quinone-CH2-C6H4-CH2CH2-C(O)-N(CH3)2) | oil | 372(M+H)+ | 2.07(3H, s), 2.57(2H, m), 2.91(2H, m), 2.92(3H, s), 2.94(3H, s), 3.81(2H, s), 3.98(3H, s), 3.99(3H, s), 7.10(4H, m) |
| 9 | (quinone-CH2-C6H4-CH2CH2-C(O)-NH-iPr) | crystal (114–116) | 386(M+H)+ | 1.06(6H, d), 2.07(3H, s), 2.37(2H, m), 2.90(2H, m), 3.80(2H, s), 3.98(3H, s), 3.99(3H, s), 4.00(1H, m), 5.05(1H, broad), 7.09(4H, s) |

| # | Structure | Form (mp °C) | MS | ¹H-NMR |
|---|---|---|---|---|
| 10 | quinone-CH₂-C₆H₄-CH₂CH₂C(O)NH-CH₂CH₂OH | crystal (97–98) | 388(M+H)⁺ | 2.08(3H, s), 2.45(2H, m), 2.92(2H, m), 3.33(2H, m), 3.59(2H, m), 3.80(2H, s), 3.98(6H, s), 5.67(1H, broad), 7.10(4H, m) |
| 11 | quinone-CH₂-C₆H₄-CH₂CH₂C(O)NH-CH₂-Ph | crystal (119–121) | 434(M+H)⁺ | 2.06(3H, s), 2.47(2H, m), 2.94(2H, m), 3.80(2H, s), 3.98(6H, s), 4.40(2H, d, J=5.7Hz), 5.55(1H, broad), 7.08(4H, s), 7.17(2H, m), 7.28(3H, m) |
| 12 | quinone-CH₂-C₆H₄-CH₂CH₂C(O)NH-CH₂CH₂-Ph | crystal (118–119) | 448(M+H)⁺ | 2.06(3H, s), 2.37(2H, m), 2.72(2H, m), 2.88(2H, m), 3.47(2H, m), 3.80(2H, s), 3.96(3H, s), 3.97(3H, s), 5.27(1H, broad), 7.08(6H, m), 7.20–7.29(3H, m) |
| 13 | quinone-CH₂-C₆H₄-CH=CH-C(O)-morpholine | crystal (124–125) | 412(M+H)⁺ | 2.08(3H, s), 3.17(8H, m), 3.85(2H, s), 3.99(6H, s), 6.77(1H, d, J=15.4Hz), 7.41(2H, m), 7.64(1H, d, J=15.4Hz) |
| 14 | quinone-CH₂-C₆H₄-CH=CH-C(O)-thiomorpholine | crystal (120–121) | 428(M+H)⁺ | 2.08(3H, s), 2.66(4H, m), 3.85(2H, s), 3.99(6H, s), 6.77(1H, d, J=15.4Hz), 7.41(2H, m), 7.61(1H, d, J=15.4Hz), 7.18(2H, m) |

| # | Structure | Form (mp) | MS | NMR |
|---|---|---|---|---|
| 15 | (piperidine amide) | crystal (162–163) | 410(M+H)⁺ | 1.50–1.75(6H, m), 2.08(3H, s), 3.45–3.75(4H, m), 3.85(2H, s), 3.99(6H, s), 6.84(1H, d, J=15.4Hz), 7.17(2H, m), 7.41(2H, m), 7.59(1H, d, J=15.4Hz) |
| 16 | (N,N-dimethyl amide) | crystal (93–94) | 370(M+H)⁺ | 2.08(3H, s), 3.06(3H, s), 3.15(3H, s), 3.85(2H, s), 3.99(6H, s), 6.38(1H, d, J=15.4Hz), 7.18(2H, m), 7.42(2H, m), 7.61(1H, d, J=15.4Hz) |
| 17 | (isopropyl amide) | crystal (118–119) | 384(M+H)⁺ | 1.22(6H, d, J=6.5Hz), 2.08(3H, s), 3.99(6H, s), 4.21(1H, m), 5.35(1H, broad d), 6.28(1H, d, J=15.6Hz), 7.17(2H, m), 7.39(2H, m), 7.55(1H, d, J=15.6Hz) |
| 18 | (2-hydroxyethyl amide) | crystal (114–115) | 386(M+H)⁺ | 2.08(3H, s), 2.51(1H, broad), 3.55(2H, m), 3.80(2H, m), 3.85(2H, s), 3.98(6H, s), 6.02(1H, broad), 6.36(1H, d, J=15.6Hz), 7.18(2H, d, J=15.6Hz), 7.40(2H, m), 7.59(1H, d, J=15.6Hz) |
| 19 | (benzyl amide) | crystal (124–125) | 432(M+H)⁺ | 2.08(3H, s), 3.85(2H, s), 3.99(6H, s), 4.57(2H, d, J=5.7Hz), 5.82(1H, m), 6.34(1H, d, J=15.6Hz), 7.17(2H, m), 7.28–7.36(5H, m), 7.39(2H, m), 7.62(1H, d, J=15.6Hz) |

-continued

| | | | NMR |
|---|---|---|---|
| 20 | [quinone with methyl, two methoxy, benzyl-phenyl-CH=CH-C(O)NH-CH2CH2-phenyl] | crystal (141–142) 446(M+H)⁺ | 2.08(3H, s), 2.88(2H, m), 3.65(2H, m), 3.84(2H, s), 3.99(6H, s), 5.54(1H, broad), 6.25(1H, d, J=15.6Hz), 7.16(2H, m), 7.22(3H, m), 7.32(2H, m), 7.38(2H, m), 7.55(1H, d, J=15.6Hz) |
| 21 | [quinone with methyl, two methoxy, benzyl-phenyl-COOH] | powder 317(M+H)⁺ | 2.08(3H, s), 3.91(3H, s), 4.00(3H, s), 7.27(2H, m), 7.99(2H, m) |
| 22 | [quinone with methyl, two methoxy, benzyl-phenyl-C(O)-morpholine] | oil 386(M+H)⁺ | 2.08(3H, s), 3.68(8H, broad), 3.86(2H, s), 4.00(6H, s), 7.22(2H, m), 7.31(2H, m) |
| 23 | [quinone with methyl, two methoxy, benzyl-phenyl-C(O)NH-iPr] | oil 358(M+H)⁺ | 1.25(6H, d, J=6.6Hz), 2.07(3H, s), 3.88(2H, s), 3.98(3H, s), 3.99(3H, s), 4.27(1H, m), 5.82(1H, broad d), 7.22(2H, m), 7.65(2H, m) |
| 24 | [quinone with methyl, two methoxy, benzyl-phenyl-C(O)-piperidine] | oil 384(M+H)⁺ | 1.54–1.66(6H, m), 2.08(3H, s), 3.49–3.68(4H, broad), 3.86(2H, s), 4.00(6H, s), 7.19(2H, m), 7.29(2H, m) |

-continued

| | | | | NMR |
|---|---|---|---|---|
| 25 | (structure: 2,3-dimethoxy-5-methyl-6-[4-(thiomorpholine-4-carbonyl)benzyl]-1,4-benzoquinone) | oil | 402(M+H)⁻ | 2.08(3H, s), 2.64(4H, broad), 3.60–4.10(4H, broad), 3.86(2H, s), 4.00(6H, s), 7.21(2H, m), 7.28(2H, m) |
| 26 | (structure: 4-[4-(2,3-dimethoxy-5-methyl-1,4-benzoquinon-6-ylmethyl)phenyl]butanoic acid) | oil | 359(M+H)⁺ | 1.92(2H, m), 2.08(3H, s), 2.34(2H, m), 2.61(2H, m), 3.80(2H, s), 3.98(3H, s), 3.98(3H, s), 7.08(4H, m) |
| 27 | (structure: morpholine amide of C3 chain) | oil | 428(M+H)⁺ | 1.94(2H, m), 2.08(3H, s), 2.28(2H, m), 2.62(2H, m), 3.37(2H, m), 3.62(6H, m), 3.81(2H, s), 3.98(3H, s), 3.99(3H, s), 7.08(4H, s) |
| 28 | (structure: thiomorpholine amide of C3 chain) | oil | 444(M+H)⁺ | 1.93(2H, m), 2.08(3H, s), 2.28(2H, m), 2.54–2.64(6H, m), 3.64(2H, m), 3.81(2H, s), 3.86(2H, m), 3.98(3H, s), 3.99(3H, s), 7.08(4H, m) |
| 29 | (structure: piperidine amide of C3 chain) | oil | 426(M+H)⁺ | 1.51–1.62(6H, m), 1.92(2H, m), 2.08(3H, s), 2.22(2H, m), 2.72(2H, m), 3.31(2H, s), 3.53(2H, m), 3.81(2H, s), 3.98(3H, s), 3.99(3H, s), 7.08(4H, m) |

| # | Structure | Form | MS | NMR |
|---|---|---|---|---|
| 30 | (isopropylamide, para-substituted trimethoxy methyl benzoquinone with butanamide linker) | powder | 400(M+H)+ | 1.13(6H, d, J=6.6Hz), 1.92(2H, m), 2.08(3H, s), 2.10(2H, m), 2.59(2H, m), 3.81(2H, s), 3.98(3H, s), 3.99(3H, s), 4.08(1H, m), 5.15(1H, broad), 7.08(4H, m) |
| 31 | (carboxylic acid, meta-substituted) | crystal (119–121) | 345(M+H)+ | 2.08(3H, s), 2.64(2H, m), 2.90(2H, m), 3.84(2H, s), 3.98(6H, s), 6.90–7.30(4H, m) |
| 32 | (piperidine amide, meta-substituted) | oil | 412(M+H)+ | 1.46–1.61(6H, m), 2.08(3H, s), 2.58(2H, m), 2.91(2H, m), 3.32(2H, m), 3.55(2H, m), 3.82(2H, s), 3.99(3H, s), 4.00(3H, s), 6.98–7.06(3H, m), 7.20(1H, m) |
| 33 | (thiomorpholine amide, meta-substituted) | oil | 430(M+H)+ | 2.08(3H, s), 2.48(2H, m), 2.55–2.60(4H, m), 2.92(2H, m), 3.66(2H, m), 3.82(2H, s), 3.88(2H, m), 3.99(3H, s), 4.00(3H, s), 7.00–7.05(3H, m), 7.19(1H, m) |
| 34 | (morpholine amide, meta-substituted) | oil | 414(M+H)+ | 2.08(3H, s), 2.58(2H, m), 2.93(2H, m), 3.36(2H, m), 3.52–3.63(6H, m), 3.82(2H, s), 3.99(3H, s), 4.00(3H, s), 6.99–7.05(3H, m), 7.19(1H, m) |

| | | | |
|---|---|---|---|
| 35 | [structure] | oil | 386(M+H)⁺ | 1.07(6H, d, J=6.5Hz), 2.07(3H, s), 2.38(2H, m), 2.90(2H, m), 3.81(2H, s), 3.99(3H, s), 4.00(3H, s), 4.03(1H, s), 5.13(1H, m), 6.98–7.04(3H, m), 7.17(1H, m) |
| 36 | [structure] | powder | 343(M+H)⁺ | 2.11(3H, s), 3.89(2H, s), 4.00(6H, s), 6.42(1H, d, J=15.4Hz), 7.15–7.50(4H, m), 7.73(1H, d, J=15.4Hz) |
| 37 | [structure] | oil | 410(M+H)⁺ | 1.61–1.71(6H, m), 2.09(3H, s), 3.57–3.66(4H, broad), 3.86(2H, s), 4.00(6H, s), 6.86(1H, d, J=15.4Hz), 7.13–7.39(4H, m), 7.57(1H, d, J=15.4Hz) |
| 38 | [structure] | oil | 412(M+H)⁺ | 2.09(3H, s), 3.73(8H, broad), 3.86(2H, s), 4.00(6H, s), 6.80(1H, d, J=15.4Hz), 7.15–7.37(4H, m), 7.63(1H, d, J=15.4Hz) |
| 39 | [structure] | oil | 384(M+H)⁺ | 1.22(6H, d, J=6.6Hz), 2.09(3H, s), 3.84(2H, s), 3.99(3H, s), 4.00(3H, s), 4.21(1H, m), 5.42(1H, broad d), 6.31(1H, d, J=15.4Hz), 7.15–7.33(4H, m), 7.54(1H, d, J=15.4Hz) |

| | | | |
|---|---|---|---|
| 40 | [structure] | oil | 428(M+H)+ | 2.09(3H, s), 2.68(4H, m), 3.86(2H, s), 3.94(4H, broad), 4.00(6H, s), 6.80(1H, d, J=15.4Hz), 7.14–7.37(4H, m), 7.60(1H, d, J=15.4Hz) |
| 41 | [structure] | powder | 317(M+H)+ | 2.08(3H, s), 3.88(2H, s), 3.99(6H, s), 7.35–7.40(2H, m), 7.89–7.93(2H, m) |
| 42 | [structure] | oil | 358(M+H)+ | 1.25(3H, s), 1.27(3H, s), 2.09(3H, s), 3.88(2H, s), 3.99(3H, s), 4.00(3H, s), 4.27(1H, m), 5.85(1H, broad), 7.26–7.33(2H, m), 7.51(1H, d, J=7.1Hz) |
| 43 | [structure] | powder | 384(M+H)+ | 1.50(2H, broad), 1.67(4H, broad), 2.08(3H, s), 3.30(2H, broad), 3.70(2H, broad), 3.86(2H, s), 3.99(3H, s), 4.00(3H, s), 7.20(3H, s), 7.29(1H, m) |
| 44 | [structure] | oil | 386(M+H)+ | 2.08(3H, s), 3.47–3.82(2H, broad), 3.86(2H, s), 3.99(6H, s), 7.21–7.33(4H, m) |

| | | | |
|---|---|---|---|
| 45 | [structure] | oil | 402(M+H)+ | 2.08(3H, s), 2.61–2.65(4H, broad), 3.57–3.86(6H, broad), 3.99(6H, s), 7.18–7.33(4H, m) |
| 46 | [structure] | powder | 354(M+H)+ | 1.05(6H, d, J=6.6Hz), 2.01(6H, s), 2.08(3H, s), 2.37(2H, m), 2.89(2H, m), 3.82(2H, s), 4.03(1H, m), 5.05(1H, broad), 7.08(4H, s) |
| 47 | [structure] | oil | 380(M+H)+ | 1.43–1.60(6H, broad), 2.01(6H, s), 2.09(3H, s), 2.57(2H, m), 2.90(2H, m), 3.31(2H, m), 3.54(2H, m), 3.82(2H, s), 7.10(4H, s) |
| 48 | [structure] | oil | 382(M+H)+ | 2.01(6H, s), 2.09(3H, s), 2.57(2H, m), 2.92(2H, m), 3.35(2H, m), 3.49(2H, m), 3.61(4H, broad), 3.83(2H, s), 7.10(4H, s) |
| 49 | [structure] | powder | 354(M+H)+ | 1.07(6H, d, J=6.5Hz), 2.02(6H, s), 2.08(3H, s), 2.38(2H, m), 2.90(2H, m), 3.83(2H, s), 4.03(1H, m), 5.09(1H, broad), 7.00(3H, m), 7.16(1H, m) |

-continued

| # | Structure | Form | MS | NMR |
|---|---|---|---|---|
| 50 | 2,3-dimethyl-5-[3-(piperidinocarbonyl)propyl-like]... quinone structure | oil | 380(M+H)+ | 1.46–1.62(6H, broad), 2.02(6H, s), 2.08(3H, s), 2.57(2H, m), 2.91(2H, m), 3.32(2H, m), 3.55(2H, m), 3.84(2H, s), 6.98–7.04(3H, m), 7.17(1H, m) |
| 51 | morpholino analog | oil | 382(M+H)+ | 2.02(3H, s), 2.04(3H, s), 2.09(3H, s), 2.58(2H, m), 2.93(2H, m), 3.36(2H, broad), 3.52(2H, broad), 3.62(4H, broad), 3.84(2H, s), 7.01(3H, m), 7.18(1H, m) |
| 52 | dimethoxy quinone with CH2-phenyl-CH2-COOH | oil | 331(M+H)+ | 2.08(3H, s), 3.63(2H, s), 3.83(2H, s), 3.98(6H, s), 7.16(2H, d, J=7.8Hz), 7.21(2H, d, J=7.8Hz). |
| 53 | dimethoxy quinone with morpholino amide | oil | 400(M+H)+ | 2.07(3H, s), 3.43(2H, m), 3.51(2H, m), 3.64(4H, broad), 3.66(2H, s), 3.82(2H, s), 3.98(6H, s), 7.13(4H, m) |
| 54 | dimethoxy quinone with piperidino amide | oil | 398(M+H)+ | 1.38(2H, broad) 1.52(2H, broad) 1.55(2H, broad) 2.08(3H, s) 3.36(2H, m) 3.55(2H, m) 3.66(6H, s), 3.82(2H, s) 3.98(3H, s) 3.99(3H, s) 7.13(4H, m) |

| | Structure | State | MS | NMR |
|---|---|---|---|---|
| 55 | (thiomorpholine amide, para-benzyl, dimethoxy methyl quinone) | oil | 416(M+H)⁺ | 2.08(3H, s) 2.34(2H, m) 2.58(2H, m) 3.67(2H, s) 3.69(2H, m) 3.82(2H, s) 3.88(2H, m) 3.99(6H, s) 7.14(4H, s) |
| 56 | (isopropyl amide, para-benzyl, dimethoxy methyl quinone) | powder | 372(M+H)⁺ | 1.07(6H, d, J=6.6Hz) 2.09(3H, s) 3.47(2H, s) 3.84(2H, s) 3.99(3H, s) 4.00(3H, s) 4.04(1H, m) 5.14(1H, broad) 7.15(4H, s) |
| 57 | (carboxylic acid, meta-benzyl, dimethoxy methyl quinone) | oil | 331(M+H)⁺ | 2.09(3H, s) 3.62(2H, s) 3.84(2H, s) 3.99(6H, s) 7.11(3H, m) 7.24(1H, m) |
| 58 | (piperidine amide, meta-benzyl, dimethoxy methyl quinone) | oil | 398(M+H)⁺ | 1.34(2H, broad) 1.53(2H, broad) 1.55(2H, broad) 2.07(3H, s) 3.35(2H, m) 3.56(2H, m) 3.68(2H, s) 3.82(2H, s) 3.99(6H, s) 7.02(1H, d, J=7.6Hz) 7.08(2H, m) 7.21(1H, m) |
| 59 | (thiomorpholine amide, meta-benzyl, dimethoxy methyl quinone) | oil | 416(M+H)⁺ | 2.08(3H, s) 2.29(2H, m) 2.57(2H, m) 3.68(4H, m) 3.83(2H, s) 3.88(2H, m) 3.99(6H, s) 7.06(3H, m) 7.23(1H, m) |

-continued

| # | Structure | Form | MS | NMR |
|---|---|---|---|---|
| 60 | (morpholine amide) | oil | 400(M+H)+ | 2.08(3H, s) 3.42(2H, m) 3.49(2H, m) 3.64(4H, s) 3.68(2H, s) 3.82(2H, s) 3.99(6H, s) 7.06(3H, m) 7.23(1H, m) |
| 61 | (isopropyl amide) | powder | 372(M+H)+ | 1.07(6H, d, J=6.6Hz) 2.08(3H, s) 3.49(2H, s) 3.84(2H, s) 4.00(6H, s) 4.04(1H, m) 5.14(1H, broad) 7.08(3H, m) 7.25(1H, m) |
| 62 | (carboxylic acid) | oil | 359(M+H)+ | 1.93(2H, m), 2.09(3H, s), 2.36(2H, m), 2.63(2H, m), 3.82(3H, s), 3.99(6H, s), 6.99–7.03(3H, m), 7.18(1H, m) |
| 63 | (piperidine amide) | oil | 426(M+H)+ | 1.51–1.63(6H, m), 1.92(2H, m), 2.08(3H, s), 2.31(2H, m), 2.62(2H, m), 3.33(2H, m), 3.54(2H, m), 3.82(2H, s), 3.99(3H, s), 4.00(3H, s), 6.97–7.04(3H, m), 7.18(1H, m) |
| 64 | (thiomorpholine amide) | oil | 444(M+H)+ | 1.94(2H, m), 2.08(3H, s), 2.29(2H, m), 2.56–2.65(6H, m), 3.66(2H, m), 3.82(2H, s), 3.87(2H, m), 3.99(3H, s), 4.00(3H, s), 6.98–7.03(3H, m), 7.18(1H, m) |

| | Structure | Form | MS | NMR |
|---|---|---|---|---|
| 65 | (morpholine amide quinone) | oil | 428(M+H)⁺ | 1.94(2H, m), 2.08(3H, s), 2.30(2H, m), 2.63(2H, m), 3.39(2H, m), 3.61–3.65(6H, m), 3.82(2H, s), 3.99(3H, s), 4.00(3H, s), 6.98–7.03(3H, m), 7.18(1H, m) |
| 66 | (isopropyl amide quinone) | oil | 400(M+H)⁺ | 1.15(6H, d, J=6.5Hz), 1.93(2H, m), 2.10(3H, s), 2.60(2H, m), 3.81(2H, s), 3.99(6H, s), 4.09(1H, m), 5.32(1H, broad), 6.97–7.02(3H, m), 7.18(1H, m) |
| 67 | (cinnamic acid quinone) | powder | 343(M+H)⁺ | 2.00(3H, s) 3.99(5H, s) 4.02(3H, s) 6.39(1H, d, J=15.7Hz) 6.96(1H, d, J=7.0Hz) 7.25–7.31(2H, m) 7.59(1H, d, J=7.2Hz) 8.22(1H, d, J=15.7Hz) |
| 68 | (thiomorpholine amide quinone) | powder | 428(M+H)⁺ | 1.97(3H, s) 2.70(4H, broad) 3.97(2H, s) 3.98(2H, s) 3.99(3H, s) 4.02(3H, s) 6.75(1H, d, J=15.1Hz) 6.89(1H, d, J=15.1Hz) 7.23(2H, m) 7.51(1H, m) 8.07(1H, d, J=15.1Hz) |

| | | | |
|---|---|---|---|
| 69 | [structure: trimethoxy-methyl-benzoquinone with CH2-phenyl-CH2CH2-COOH] | oil | 345(M+H)+ | 2.02(3H, s) 2.77(2H, m) 3.10(2H, m) 3.85(2H, s) 3.98(3H, s) 4.03(3H, s) 6.81(1H, d, J=7.5Hz) 7.10–7.21(3H, m) |
| 70 | [structure: trimethoxy-methyl-benzoquinone with CH2-phenyl-CH2CH2-C(=O)-piperidine] | oil | 412(M+H)+ | 1.47–1.62(6H, broad) 2.00(3H, s) 2.70(2H, m) 3.10(2H, m) 3.38(2H, m) 3.58(2H, m) 3.66(2H, m) 3.98(3H, s) 4.03(3H, s) 6.78(1H, d, J=7.4Hz) 7.09(1H, m) 7.14(1H, m) 7.20(1H, m) |
| 71 | [structure: trimethoxy-methyl-benzoquinone with CH2-phenyl-CH2CH2-C(=O)-morpholine] | oil | 414(M+H)+ | 2.02(3H, s) 2.73(2H, m) 3.11(2H, m) 3.42(2H, m) 3.49(2H, m) 3.64(4H, s) 3.85(2H, s) 3.98(3H, s) 4.03(3H, s) 6.79(1H, d, J=7.5Hz) 7.10–7.19(3H, m) |

-continued

| No. | Structure | | FABMS(m/z) |
|---|---|---|---|
| 72 | (structure: dimethoxy-methyl-benzoquinone with benzyl-CH2CH2-C(O)-thiomorpholine) | powder | 430(M+H)+ |
|  | NMR: 2.02(3H, s) 2.44(2H, m) 2.60(2H, m) 2.72(2H, m) 3.10(2H, m) 3.68(2H, m) 3.85(2H, s) 3.90(2H, m) 3.98(3H, s) 4.03(3H, s) 6.79(1H, d, J=7.5Hz) 7.08–7.21(3H, m) | | |
| 73 | (structure: dimethoxy-methyl-benzoquinone with benzyl-CH2CH2-C(O)-NH-iPr) | powder | 386(M+H)+ |
|  | NMR: 1.02(6H), d, J=6.6Hz) 2.06(3H, s) 2.56(2H, m) 3.08(2H, m) 3.85(2H, s) 3.97(3H, s) 4.00 (1H, m) 4.04(3H, s) 5.52(1H, broad) 6.79(1H, d, J=7.4Hz) 7.10(2H, m) 7.18(1H, d, J=7.3Hz) | | |

| Ex. No. | Structure | | | |
|---|---|---|---|---|
| 74 | (structure: dimethoxy-methyl-benzoquinone-CH2-para-phenylene-CH2CH2-C(O)-(2-methoxymethyl-pyrrolidine)) | | | |

| | | Property | FABMS(m/z) | NMR(CDCl₃, δ) |
|---|---|---|---|---|
| | Weight (yield) | | | |
| | 38 mg (29%) | oil | 442(M+H)+ | 1.82–1.98(4H, m), 2.08(3H, s), 2.52(2H, m), 2.93(3H, m), 3.15–3.23(1H, m), 3.33(3H, s), 3.36–3.40(1H, m), 3.50–5.53(1H, m), 3.81(2H, s), 3.98(3H, s), 3.99(3H, s), 4.24(1H, m), 7.10(4H, m) |

-continued

| | Structure | Yield | MS | NMR |
|---|---|---|---|---|
| 75 | (quinone-CH2-C6H4-CH2CH2-C(O)NH-indanyl) | 34 mg (25%) powder | 460(M+H)+ | 1.66(1H, m), 2.07(3H, s), 2.37(2H, m), 2.53(1H, m), 2.86(2H, m), 2.96(2H, m), 3.81(2H, s), 3.98(3H, s), 3.99(3H, s), 5.46(1H, m), 5.50(1H, d, J=8.4Hz), 7.10–7.22(5H, m) |
| 76 | (quinone-CH2-C6H4-CH2CH2-C(O)-pyrrolidine-CH2OMe) | 36 mg (27%) oil | 442(M+H)+ | 1.82–1.98(4H, m), 2.08(3H, s), 2.52(2H, m), 2.92(3H, m), 3.15–3.23(1H, m), 3.33(3H, s), 3.36–3.40(1H, m), 3.50–5.54(1H, m), 3.81(2H, s), 3.98(3H, s), 3.99(3H, s), 4.24(1H, m), 7.10(4H, m) |
| 77 | (quinone-CH2-C6H4-CH2CH2-C(O)-proline methyl ester) | 79 mg (58%) oil | 456(M+H)+ | 1.90–2.16(4H, m), 2.08(3H, s), 2.38–2.63(2H, m), 2.93(2H, m), 3.37(1H, m), 3.56(1H, m), 3.73(3H, s), 3.81(2H, s), 3.98(3H, s), 3.99(3H, s), 4.48(1H, m), 7.12(4H, m) |
| 78 | (quinone-CH2-C6H4-CH2CH2-C(O)-piperazine-C6H4-C(O)CH3) | 61 mg (23%) powder | 531(M+H)+ | 2.17(3H, s), 2.53(3H, s), 2.63(2H, m), 2.95(2H, m), 3.24(2H, m), 3.32(2H, m), 3.54(2H, m), 3.78(2H, m), 3.80(2H, m), 3.98(6H, s), 6.84(2H, m), 7.11(4H, m), 7.89(2H, m) |

| # | Structure | Yield | MS | NMR |
|---|---|---|---|---|
| 79 | | 41 mg (30%) powder | 455(M+H)+ | 1.43–1.60(2H, m), 1.80–1.92(2H, m), 2.08(3H, s), 2.34(1H, m), 2.58(2H, m), 2.67 (1H, m), 2.89–2.97(3H, m), 3.78(1H, m), 3.81(2H, s), 3.99(6H, s), 4.59(1H, m), 5.38(1H, broad s), 5.51(1H, broad s), 7.10(4H, m) |
| 80 | | 59 mg (38%) powder | 517(M+H)+ | 1.29–1.35(2H, m), 1.82(2H, m), 2.07(3H, s), 2.09(2H, m), 2.38–2.42(2H, m), 2.76(2H, m), 2.87–2.91(2H, m), 3.47(2H, s), 3.76(1H, m), 3.80(2H, s), 3.98(6H, s), 5.14(1H, d, J=8.1Hz), 7.08(4H, s), 7.24–7.33(4H, m) |
| 81 | | 68 mg (53%) oil | 426(M+H)+ | 0.92(3H, t, J=6.5Hz), 0.96–1.10(2H, m), 1.55–1.66(3H, m), 2.08(3H, s), 2.52–2.59(3H, m), 2.89–2.94(3H, m), 3.74(1H, m), 3.81(2H, s), 3.98(3H, s), 3.99(3H, s), 4.58(1H, m), 7.07–7.13(4H, m) |
| 82 | | 120 mg (78%) oil | 511(M+H)+ | 1.10 and 1.21(total 6H, both d, J=7.1Hz), 1.71–1.92(3H, m), 2.08(3H, s), 2.43–2.69(4H, m), 2.89–3.00(3H, m), 3.20–3.49(5H, m), 3.78(1H, m), 3.81(2H, s), 3.98(3H, s), 3.99(3H, s), 4.65(1H, m), 7.08–7.11(4H, m) |
| 83 | | 59 mg (46%) oil | 426(M+H)+ | 1.10–1.17(3H, m), 1.24–1.37(1H, broad), 1.50–1.58(5H, m), 2.08(3H, s), 2.53–2.67(2.5H, m), 2.90–3.13(2.5H, m), 3.56(0.5H, m), 3.81(2H, s), 3.98(3H, s), 3.99(3H, s), 4.06(0.5H, m), 4.52(0.5H, m), 4.93(0.5H, broad), 7.08–7.13(4H, m) |

| # | Structure | Yield | MS | NMR |
|---|---|---|---|---|
| 84 | (2,3-dimethoxy-5-methyl-quinone with CH2-C6H4-CH2CH2C(O)NH-indanyl) | 63 mg (46%) powder | 460(M+H)+ | 2.07(3H, s), 2.37(2H, m), 2.65–2.70(2H, m), 2.89(2H, m), 3.23–3.29(2H, m), 3.80(2H, s), 3.98(6H, s), 4.71(1H, m), 5.51(1H, d, J=7.4Hz), 7.07(4H, s), 7.16–7.22(4H, m) |
| 85 | (quinone with CH2-C6H4-CH2CH2C(O)-(3-methylpiperidinyl)) | 69 mg (54%) oil | 426(M+H)+ | 0.85 and 0.88(total 3H, both d, J=6.6Hz), 1.03–1.14(1H, m), 1.24–1.67(3H, m), 1.78(1H, m), 2.08(3H, s), 2.17–2.23(0.5H, m), 2.55–2.60(3H, m), 2.83–2.93(2.5H, m), 3.60(0.5H, m), 3.68(0.5H, m), 3.81(2H, s), 3.98(3H, s), 3.99(3H, s), 4.44(1H, m), 7.08–7.13(4H, m) |
| 86 | (quinone with CH2-C6H4-CH2CH2C(O)-(2,6-dimethylpiperidinyl)) | 20 mg (15%) oil | 440(M+H)+ | 1.19(6H, d, J=7.0Hz), 1.42–1.63(5H, m), 1.73–1.79(1H, m), 2.08(3H, s), 2.53–2.64(2H, m), 2.91–2.95(2H, m), 3.81(2H, s), 3.98(3H, s), 3.99(3H, s), 4.00(1H, broad), 4.77(1H, broad), 7.08–7.14(4H, m) |
| 87 | (quinone with CH2-C6H4-CH2CH2C(O)-(2-hydroxymethylpyrrolidinyl)) | 64 mg (50%) oil | 428(M+H)+ | 1.52–1.57(1H, m), 1.74–1.88(2H, m), 1.95–2.02(1H, m), 2.08(3H, s), 2.53–2.59(2H, m), 2.90–2.96(2H, m), 3.27–3.41(2H, m), 3.51–3.57(1H, m), 3.62–3.68(1H, m), 3.81(2H, m), 3.99(6H, s), 4.18–4.21(1H, m), 5.05–5.30(1H, m), 7.09–7.14(4H, m) |

-continued

| # | Structure | Yield | MS | NMR |
|---|---|---|---|---|
| 88 | (quinone with dimethoxy, methyl, CH2-phenyl-CH2CH2-C(O)-N-piperidine-2-CH2OH) | 48 mg (36%) oil | 442(M+H)+ | 1.01–1.93(6H, m), 2.08(3H, s), 2.43–2.71(3H, m), 2.89–3.11(3H, m), 3.58–3.66(2H, m), 3.78–3.91(1H, m), 3.81(2H, s), 3.98(3H, s), 3.99(3H, s), 4.59–4.79(1H, m), 7.09–7.13 (4H, m) |
| 89 | (quinone with dimethoxy, CH2-phenyl-CH2CH2-C(O)NH-benzo[1,3]dioxole) | 120 mg (86%) oil | 464(M+H)+ | 2.07(3H, s), 2.58(2H, m), 2.99(2H, m), 3.61(2H, s), 3.98(6H, s), 5.94(2H, s), 6.65(1H, m), 6.71(1H, m), 6.87(1H, broad), 7.12(5H, m) |
| 90 | (quinone with dimethoxy, methyl, CH2-phenyl-CH2CH2-C(O)NH-benzodioxine) | 110 mg (77%) oil | 478(M+H)+ | 2.07(3H, s), 2.58(2H, m), 2.99(2H, m), 3.81(2H, s), 3.98(6H, s), 4.23(4H, broad s), 6.77(2H, m), 6.81(1H, broad), 7.12(4H, m) |
| 91 | (quinone with dimethoxy, methyl, CH2-phenyl-CH2CH2-C(O)NH-phenyl-morpholine) | 46 mg (30%) powder | 505(M+H)+ | 2.07(3H, s), 2.59(2H, m), 3.00(2H, m), 3.11(4H, m), 3.84(6H, m), 3.98(6H, s), 6.85(4H, m), 7.12(4H, m), 7.28(1H, m) |

| # | Yield | Structure | MS | ¹H NMR |
|---|---|---|---|---|
| 92 | 136 mg (52%) oil | *2,3-dimethoxy-5-methyl-6-{4-[2-(4-benzoylphenylcarbamoyl)ethyl]benzyl}-1,4-benzoquinone* | 524(M+H)⁺ | 2.08(3H, s), 2.68(2H, m), 3.02(2H, m), 3.81(3H, s), 3.97(6H, s), 7.12(4H, m), 7.41 (1H, broad s), 7.46–7.60(4H, m), 7.78(4H, m) |
| 93 | 59 mg (43%) powder | *2,3-dimethoxy-5-methyl-6-{4-[2-(4-acetylphenylcarbamoyl)ethyl]benzyl}-1,4-benzoquinone* | 462(M+H)⁺ | 2.08(3H, s), 2.57(3H, s) 2.67(2H, m) 3.01(2H, m) 3.81(2H, s) 3.98(6H, s) 7.13(4H, m) 7.21(1H, broad) 7.53(2H, broad) 7.91(2H, m) |
| 94 | 79 mg (59%) powder | *2,3-dimethoxy-5-methyl-6-{4-[2-(4-methoxyphenylcarbamoyl)ethyl]benzyl}-1,4-benzoquinone* | 450(M+H)⁺ | 2.08(3H, s), 2.60(2H, m), 3.00(2H, m), 3.78(3H, s), 3.81(2H, s), 3.98(6H, s), 6.83(2H, m), 6.86(1H, broad), 7.12(4H, m), 7.30(2H, m) |
| 95 | 63 mg (45%) powder | *2,3-dimethoxy-5-methyl-6-{4-[2-(4-dimethylaminophenylcarbamoyl)ethyl]benzyl}-1,4-benzoquinone* | 463(M+H)⁺ | 2.08(3H, s), 2.58(2H, m), 2.91(6H, s), 3.00(2H, m), 3.81(2H, s), 3.98(6H, s), 6.67(2H, d, J=9.0Hz), 6.81(1H, broad), 7.12(4H, m), 7.24(2H, d, J=8.9Hz) |

| | | | |
|---|---|---|---|
| 96 | [structure] | 45 mg (34%) powder | 436(M+H)+ | 2.08(3H, s), 2.72(2H, m), 3.02(2H, m), 3.82(2H, s), 3.98(3H, s), 3.99(3H, s), 6.82(2H, d, J=4.2Hz), 6.99(1H, d, J=7.9Hz), 7.08–7.19(6H, m), 8.58(1H, broad) |
| 97 | [structure] | 60 mg (46%) oil | 436(M+H)+ | 2.12(3H, s), 2.62(2H, m), 3.00(2H, m), 3.83(2H, s) 3.98(3H, s), 3.99(3H, s) 6.61 (1H, d, J=8.1Hz) 6.66(1H, broad) 6.78(1H, broad) 6.83(1H, d, J=8.1Hz) 7.11–1.17(5H, m) 8.02(1H, broad) |
| 98 | [structure] | 94 mg (64%) oil | 488(M+H)+ | 2.08(3H, s), 2.62(2H, m), 2.99(2H, m), 3.81(2H, s), 3.98(6H, s), 7.00(1H, broad), 7.08(1H, broad), 7.12(4H, s), 7.40(2H, s) |
| 99 | [structure] | 120 mg (84%) oil | 480(M+H)+ | 2.07(3H, s), 2.61(2H, m) 3.00(2H, m) 3.75(3H, s) 3.77(3H, s) 3.81(2H, s) 3.98(6H, s) 6.22(1H, broad) 6.69(2H, broad) 6.95(1H, broad) 7.12(4H, m) |

| | | | |
|---|---|---|---|
| 100 | 71 mg (48%) powder | 492(M+H)+ | 1.38(3H, m), 2.08(3H, s), 2.66(2H, m), 3.01(2H, m), 3.81(2H, s), 3.98(6H, s), 4.35(2H, m), 7.11(4H, m), 7.15(1H, broad), 7.51(2H, d, J=8.5Hz), 7.98(2H, d, J=8.7Hz) |
| 101 | 63 mg (41%) powder | 510(M+H)+ | 2.08(3H, s), 2.61(2H, m), 3.00(2H, m), 3.81(5H, s), 3.84(6H, s), 3.98(6H, s), 6.76(2H, s), 6.98(1H, broad), 7.12(4H, m) |
| 102 | 94 mg (56%) oil | 556(M+H)+ | 2.07(3H, s), 2.67(2H, m), 3.01(2H, m), 3.81(2H, s), 3.98(6H, s), 7.12(4H, s), 7.43(1H, broad), 7.59(1H, broad), 7.95(2H, s) |
| 103 | 31 mg (20%) powder | 480(M+H)+ | 2.08(3H, s), 2.60(2H, m), 3.00(2H, m), 3.81(2H, m), 3.85(3H, s), 3.88(3H, s), 3.98(6H,s), 6.71(1H, m), 6.78(1H, m), 6.91(1H, broad), 7.13(4H, m), 7.31(1H, broad) |

| # | Structure | Yield | MS | NMR |
|---|---|---|---|---|
| 104 | (quinone with methyl, two methoxy, benzyl-CH2CH2-C(=O)NH-CH(CH3)CH2OH) | 46 mg (40%) oil | 402(M+H)+ | 1.06(3H, d, J=7.0Hz), 2.08(3H, s), 2.41–2.46(2H, m), 2.91(2H, m), 3.40–3.44(1H, m), 3.52–3.56(1H, m), 3.81(2H, s), 3.99(6H, m), 5.40(1H, m), 7.10(4H, s) |
| 105 | (quinone with methyl, two methoxy, benzyl-CH2CH2-C(=O)-piperidine-CO2Et) | 91 mg (63%) oil | 484(M+H)+ | 1.27(3H, t, J=7.1Hz), 1.28–1.70(4H, m), 2.08(3H, s), 2.25(1H, m), 2.64(2H, m), 2.92(2H, m), 3.19–3.36(1H, m), 3.71(1H, m), 3.81(2H, s), 3.98(3H, s), 3.99(3H, s), 4.15–4.21(3H, m), 5.37(1H, m), 7.08–7.14(4H, m) |
| 106 | (quinone with methyl, two methoxy, benzyl-CH2CH2-C(=O)-prolinamide) | 93 mg (70%) oil | 441(M+H)+ | 1.78(1H, m), 1.93(1H, m), 2.04(1H, m), 2.08(3H, s), 2.40(1H, m), 2.60(2H, m), 2.94(2H, m), 3.29(1H, m), 3.45(1H, m), 3.81(2H, s), 3.98(3H, s), 3.99(3H, s), 4.58(1H, m), 5.30(1H, broad s), 6.92(1H, broad s), 7.11(4H, m) |
| 107 | (quinone with methyl, two methoxy, benzyl-CH2CH2-C(=O)-piperidine-CO2Et) | 110 mg (76%) oil | 484(M+H)+ | 1.25(3H, t, J=7.1Hz), 1.29–1.48(1H, m), 1.58–1.78(2H, m), 2.02(1H, m), 2.08(3H, s), 2.25–2.43(1H, m), 2.56–2.67(2H, m), 2.78–3.01(3.5H, m), 3.28–3.34(0.5H, m), 3.66–3.75(1H, m), 3.81(2H, s), 3.98(3H, s), 3.99(3H, s), 4.11–4.16(3H, m), 4.65(0.5H, m), 7.10(4H, m) |
| 108 | (quinone with methyl, two methoxy, benzyl-CH2CH2-C(=O)NH-phenyl-O-phenyl) | 140 mg (90%) powder | 512(M+H)+ | 2.07(3H, s), 2.61(2H, m), 3.00(2H, m), 3.81(2H, s), 3.98(6H, s), 6.92–6.98(4H, m), 7.04–7.15(6H, s), 7.30–7.38(4H, m) |

| | | | | |
|---|---|---|---|---|
| 109 | [structure] | 59 mg (43%) oil | 466(M+H)+ | 0.98–1.76(13H, broad) 2.07(1H, broad) 2.08(3H, s) 2.56(2H, m) 2.92(2H, m) 3.14(2H, broad) 3.81(2H, s) 3.98(3H, s) 3.99(3H, s) 7.11(4H, m) |
| 110 | [structure] | 130 mg (88%) oil | 492(M+H)+ | 1.38(3H, t, J=7.1Hz), 2.07(3H, s), 2.64(2H, m), 3.00(2H, m), 3.81(2H, s), 3.98(6H, s), 4.32–4.39(3H, m), 7.12(4H, m), 7.20(1H, m), 7.36(1H, m), 7.76–7.93(3H, m) |
| 111 | [structure] | 72 mg (52%) powder | 459(M+H)+ | 2.07(3H, s), 2.63(2H, m), 3.00(2H, m), 3.71(2H, s), 3.81(2H, s), 3.99(6H, s), 7.02(1H, broad s), 7.11(4H, m), 7.25(2H, m), 7.44(2H, m) |
| 112 | [structure] | 130 mg (94%) powder | 462(M+H)+ | 1.22(6H, d, J=6.9Hz), 2.07(3H, s), 2.60(2H, m), 2.86(1H, m), 3.00(2H, m), 3.81(2H, s), 3.98(6H, s), 6.96(1H, broad s), 7.09–7.16(6H, m), 7.32(2H, m) |

| | | | |
|---|---|---|---|
| 113 | [structure] | 60 mg (41%) powder | 490(M+H)⁺ | 0.88(3H, t, J=6.7Hz), 1.27–1.35(4H, m), 1.56–1.61(2H, m), 2.07(3H, s), 2.53–2.62(4H, m), 3.00(2H, m), 3.81(2H, s), 3.98(6H, s), 6.96(1H, broad s), 7.11–7.15(6H, m), 7.31(2H, m) |
| 114 | [structure] | 84 mg (28%) powder | 594(M+H)⁺ | 2.08(3H, s), 2.59(2H, m), 2.98(2H, m), 3.82(2H, s), 3.98(6H, s), 5.75(1H, broad s), 6.95(1H, broad s), 7.11(4H, s), 7.58(2H, s) |
| 115 | [structure] | 42 mg (30%) powder | 446(M+H)⁺ | 2.08(3H, s), 2.58(2H, m), 2.99(2H, m), 3.81(2H, s), 3.86(3H, s), 3.98(6H, s), 6.76(1H, d, J=8.6Hz), 6.90–7.09(3H, m), 7.11(4H, m) |
| 116 | [structure] | 92 mg (62%) powder | 492(M+H)⁺ | 0.97(3H, t, J=7.4Hz), 1.45–1.52(2H, m), 1.71–1.78(2H, m), 2.08(3H, s), 2.59(2H, m), 3.00(2H, m), 3.81(2H, s), 3.92(2H, m), 3.98(6H, s), 6.82(2H, m), 7.12(4H, m), 7.29(2H, m) |

-continued

| | | | | NMR |
|---|---|---|---|---|
| 117 | [structure: 2,3-dimethoxy-5-methyl-1,4-benzoquinone with CH2-phenyl-CH2CH2-C(O)NH-(4-trifluoromethylphenyl)] | 85 mg (58%) powder | 488(M+H)+ | 2.08(3H, s), 2.65(2H, m), 3.00(2H, m), 3.81(2H, s), 3.98(6H, s), 7.12(5H, m), 7.54(4H, m) |
| 118 | [structure: 2,3-dimethoxy-5-methyl-1,4-benzoquinone with CH2-phenyl-CH2CH2-C(O)NH-(4-cyanophenyl)] | 71 mg (60%) powder | 445(M+H)+ | 2.08(3H, s), 2.66(2H, m), 3.00(2H, m), 3.81(2H, s), 3.99(6H, s), 7.10–7.15(5H, m), 7.53–7.60(4H, m) |
| 119 | [structure: 2,3-dimethoxy-5-methyl-1,4-benzoquinone with CH2-phenyl-CH2CH2-C(O)NH-(3-hydroxy-4-tert-butoxycarbonylphenyl)] | 88 mg (33%) oil | 536(M+H)+ | 1.60(9H, s), 2.08(3H, s), 2.63(2H, m), 2.99(2H, m), 3.81(2H, s), 3.98(6H, s), 6.99–7.13(7H, m), 7.68(1H, m), 11.12(1H, s) |

| | | | |
|---|---|---|---|
| 120 | 75 mg (61%) oil | 448(M+H)+ | 1.40(3H, d, J=6.8Hz) 2.07(3H, s) 2.43(2H, m) 2.91(2H, m) 3.81(2H, s) 3.98(3H, s) 3.99(3H, s) 5.09(1H, s) 5.49(1H, broad) 7.07(4H, s) 7.21(2H, m) 7.24–7.33(3H, m) |
| 121 | 80 mg (58%) oil | 448(M+H)+ | 1.40(3H, d, J=7.0Hz) 2.08(3H, s) 2.43(2H, m) 2.91(2H, m) 3.81(2H, s), 3.98(3H, s) 3.99(3H, s) 5.09(1H, s) 5.48(1H, broad) 7.07(4H, s) 7.21(2H, m), 7.25–7.33(3H, m) |
| 122 | 39 mg (28%) powder | 457(M+H)+ | 2.07(3H, s) 2.38–2.48(8H, m) 2.90(2H, m) 3.32(2H, m) 3.67(4H, m) 3.80(2H, s) 3.98(3H, s) 3.99(3H, s) 5.88(1H, broad) 7.10(4H, s) |
| 123 | 68 mg (53%) oil | 428(M+H)+ | 0.90(9H, s) 1.32(2H, m) 2.07(3H, s) 2.40(2H, m) 2.90(2H, m) 3.21(2H, m) 3.80(2H, s) 3.98(3H, s) 3.99(3H, s) 5.19(1H, broad) 7.09(4H, s) |

| | | | |
|---|---|---|---|
| 124 | [structure] | 59 mg (48%) powder | 414(M+H)⁺ | 0.78(6H, m) 1.27(2H, m) 1.46(2H, m) 2.07(3H, s) 2.43(2H, m) 2.92(2H, m) 3.74(1H, m) 3.80(2H, s) 3.98(3H, s) 3.99(3H, s) 4.96(1H, broad) 7.10(4H, m) |
| 125 | [structure] | 22 mg (18%) powder | 418(M+H)⁺ | 2.10(3H, s) 2.47(2H, m) 2.93(2H, m) 3.59(2H, m) 3.73(2H, m) 3.81(2H, s) 3.85(1H, m) 3.98(3H, s) 3.99(3H, s) 5.96(1H, broad) 7.10(4H, m) |
| 126 | [structure] | 49 mg (40%) powder | 416(M+H)⁺ | 0.84(2H, m) 1.38(1H, m) 1.49(1H, m) 2.08(3H, s) 2.33(1H, broad) 2.46(2H, m) 2.92(2H, m) 3.52(2H, m) 3.78(1H, broad) 3.81(2H, s) 3.99(6H, s) 5.37(1H, broad) 7.10(4H, s) |
| 127 | [structure] | 53 mg (44%) powder | 400(M+H)⁺ | 0.80(3H, t, J=6.6Hz) 1.36(2H, m) 2.07(3H, s) 2.40(2H, m) 2.91(2H, m) 3.80(2H, s) 3.87(1H, m) 3.98(3H, s) 3.99(3H, s) 5.03(1H, broad) 7.09(4H, s) |
| 128 | [structure] | 61 mg (48%) oil | 428(M+H)⁺ | 0.86(6H, d, J=6.5Hz) 1.12–1.27(2H, m) 1.46(1H, m) 2.07(3H, s) 2.39(2H, m) 2.90(2H, m) 3.80(2H, s) 3.98(3H, s) 3.99(3H, s) 4.01(1H, m) 4.99(1H, broad) 7.09(4H, s) |

| | | | |
|---|---|---|---|
| 129 | [structure] | 62 mg (45%) powder | 456(M+H)⁺ | 0.87(3H, m) 1.03(3H, d, J=6.5Hz) 1.24–1.32(10H, broad) 2.07(3H, s) 2.39(2H, m) 2.90(2H, m) 3.80(2H, m) 3.93(1H, m) 3.98(3H, s) 3.99(3H, s) 5.03(1H, broad) 7.09(4H, s) |
| 130 | [structure] | 59 mg (43%) oil | 458(M+H)⁺ | 1.14(3H, d, J=6.7Hz) 1.26(3H, m) 2.07(3H, s) 2.38–2.45(4H, m) 2.89(2H, m) 3.80(2H, s) 3.98(3H, s) 3.99(3H, s) 4.13(2H, m) 4.32(1H, m) 5.98(1H, broad) 7.09(4H, s) |
| 131 | [structure] | 49 mg (39%) powder | 444(M+H)⁺ | 0.87(3H, m) 1.22–1.37(6H, m) 2.08(3H, s) 2.33(1H, m) 2.46(2H, m) 2.92(2H, m) 3.48(1H, m) 3.54(1H, m) 3.81(2H, s) 3.86(1H, m) 3.99(6H, s) 5.37(1H, broad) 7.10(4H, s) |
| 132 | [structure] | 49 mg (41%) oil | 398(M+H)⁺ | 1.80–1.90(4H, m) 2.08(3H, s) 2.52(2H, m) 2.93(2H, m) 3.28(2H, m) 3.45(2H, m) 3.80(2H, s) 3.98(3H, s) 3.99(3H, s) 7.11(4H, m) |
| 133 | [structure] | 43 mg (32%) powder | 455(M+H)⁺ | 1.39(2H, broad) 1.82(2H, broad) 2.02(2H, broad) 2.07(3H, s) 2.50(2H, m) 2.91(2H, m) 3.25(2H, m) 3.80(2H, s) 3.98(3H, s) 3.99(3H, s) 4.48(1H, m) 5.87(1H, broad) 6.80(1H, broad) 7.09(4H, s) |

| | | | |
|---|---|---|---|
| 134 | [structure] | 70 mg (56%) oil | 414(M+H)+ | 1.76–2.00(3H, broad) 2.08, 2.09(total 3H, both s) 2.53(2H, m) 2.93(2H, m) 3.15(0.4H, m) 3.34–3.62(3.6H, m) 3.81(2H, s) 3.98(3H, s) 3.99(3H, s) 4.46(1H, broad) 7.10(4H, m) |
| 135 | [structure] | 25 mg (19%) oil | 426(M+H)+ | 1.08, 1.13, 1.29(total 6H, all d, J=6.4, 6.5, 6.3Hz) 1.48–1.66(2.5H, m) 1.80–1.88(0.7H, m) 1.99–2.06(1.3H, m) 2.08(3H, s) 2.53(2H, m) 2.94(2H, m) 3.81(2H, s) 3.82(1H, m) 3.98(3H, s) 3.99(3H, s) 4.05–4.23(0.5H, m) 7.11(4H, m) |
| 136 | [structure] | 79 mg (60%) powder | 440(M+H)+ | 1.30(2H, m) 1.45–1.58(5H, broad) 1.82(2H, broad) 2.07(3H, s) 2.18(3H, s) 2.38(2H, m) 2.90(2H, m) 3.80(2H, s) 3.91(1H, m) 3.98(3H, s) 3.99(3H, s) 5.19(1H, broad) 7.09(4H, s) |
| 137 | [structure] | 72 mg (55%) oil | 440(M+H)+ | 0.71(1H, m) 0.83, 0.88(total 6H, both d, J=6.6, 6.5Hz) 1.37–1.54(1.8H, broad) 1.75–1.98(2.2H, m) 2.09(3H, s) 2.40(0.7H, m) 2.58(2H, m) 2.90(2H, m) 3.05(0.3H, m) 3.30(0.2H, broad) 1.95(1H, m) 2.09(2H, s) 3.98(3H, s) 3.99(3H, s) 4.59(0.8H, broad) 7.11(4H, m) |
| 138 | [structure] | 35 mg (27%) oil | 428(M+H)+ | 1.33–1.92(4.7H, m) 2.09, 2.08(total 3H, both s) 2.61(2H, m) 2.92(2H, m) 3.02–3.89(5.3H, s) 3.81(2H, s) 3.98(3H, s) 3.99(3H, s) 7.11(4H, m) |

| # | Structure | Yield | MS | NMR |
|---|---|---|---|---|
| 139 | | 27 mg (21%) oil | 427(M+H)+ | 2.08(3H, s), 2.28(5H, s) 2.34(2H, m) 2.58(2H, m) 2.91(2H, m) 3.40(2H, m) 3.63(2H, broad) 3.81(2H, s) 3.98(3H, s) 3.99(3H, s) 7.11(4H, s) |
| 140 | | 140 mg (95%) oil | 491(M+H)+ | 1.86(3H, s), 2.07(3H, s), 2.65(2H, m), 3.01(2H, m), 3.23(3H, s), 3.81(2H, s), 3.98(6H, s), 7.12(6H, m), 7.36(1H, broad s), 7.49(2H, m) |
| 141 | | 114 mg (76%) oil | 501(M+H)+ | 2.08(3H, s), 2.40(2H, m), 2.46(2H, m), 2.57(4H, m), 2.91(2H, m), 3.42(2H, m), 3.60–3.71(8H, m), 3.81(2H, s), 3.98(3H, s), 3.99(3H, s), 7.11(4H, m) |
| 142 | | 44 mg (33%) oil | 441(M+H)+ | 2.08(3H, s), 2.62(2H, m), 2.93(2H, m), 3.15–3.65(8H, m), 3.80(2H, s), 3.98(3H, s), 3.99(3H, s), 7.11(4H, s), 8.06(1H, s) |
| 143 | | 80 mg (59%) oil | 455(M+H)+ | 2.08(3H, s), 2.11(3H, s), 2.61(2H, m), 2.93(2H, m), 3.29–3.65(8H, m), 3.81(2H, s), 3.99(6H, s), 7.11(4H, m) |

| # | Structure | Yield | MS | NMR |
|---|---|---|---|---|
| 144 | | 57 mg (42%) oil | 455(M+H)+ | 1.25–1.92(4H, m), 2.09(3.8H, m), 2.38(0.7H, m), 2.53–2.72(2.5H, m), 2.90(2H, m), 3.30–3.42(1.4H, m), 3.66–3.71(0.7H, m), 3.81(3H, m), 3.97, 3.98, 3.99, 4.00(total 6H, all s), 4.51(0.2H, broad s), 5.30(1H, broad s), 5.80(0.2H, broad s), 6.47(0.6H, broad s), 7.10(4H, m) |
| 145 | | 102 mg (74%) oil | 460(M+H)+ | 1.85(2H, m), 2.07(3H, s), 2.57(2H, broad), 2.77(2H, m), 2.93(2H, m), 3.73(2H, m), 3.79(2H, s), 3.98(3H, s), 3.99(3H, s), 6.98–7.16(4H, m) |
| 146 | | 110 mg (76%) oil | 484(M+H)+ | 1.25(3H, t, J=7.1Hz), 1.55–1.64(2H, m), 1.83–1.94(2H, m), 2.08(3H, s), 2.49(1H, m), 2.58(2H, m), 2.80(1H, m), 2.91(2H, m), 3.03(1H, m), 3.75(1H, m), 3.81(2H, s), 3.98(3H, s), 3.99(3H, s), 4.14(2H, q, J=7.1Hz), 4.42(1H, m), 7.11(4H, m) |
| 147 | | 91 mg (63%) oil | 485(M+H)+ | 1.27(3H, t, J=7.1Hz), 2.08(3H, s), 2.59(2H, m), 2.92(2H, m), 3.36(2H, m), 3.44(2H, m), 3.60(2H, m), 3.81(2H, s), 3.98(3H, s), 3.99(3H, s), 4.15(2H, q, J=7.1Hz), 7.11(4H, m) |
| 148 | | 90 mg (62%) oil | 489(M+H)+ | 2.07(3H, s), 2.63(2H, m), 2.94(2H, m), 3.06(2H, m), 3.12(2H, m), 3.54(2H, m), 3.80(4H, m), 3.98(3H, s), 3.99(3H, s), 6.91(3H, m), 7.11(4H, m), 7.28(2H, m) |

| | | | | |
|---|---|---|---|---|
| 149 | 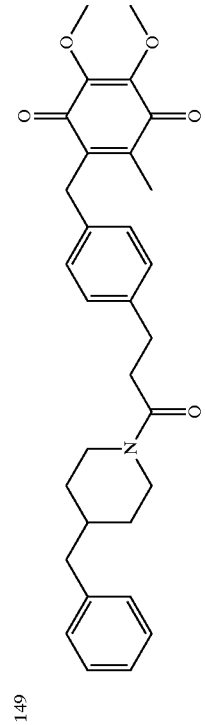 | 107 mg (71%) | oil | 502(M+H)+ | 0.98–1.17(2H, m), 1.64–1.73(3H, m), 2.08(3H, s), 2.47–2.58(5H, m), 2.86–2.92(3H, m), 3.76(1H, m), 3.81(2H, s), 3.98(3H, s), 3.99(3H, s), 4.61(1H, m), 7.08–7.30(9H, m) |
| 150 | 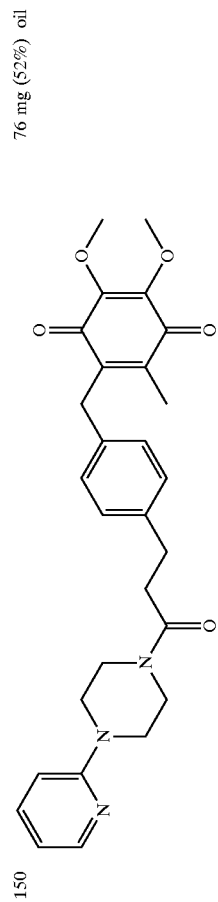 | 76 mg (52%) | oil | 490(M+H)+ | 2.07(3H, s), 2.63(2H, m), 2.95(2H, m), 3.50(6H, m), 3.75(2H, m), 3.80(2H, s), 3.98(3H, s), 3.99(3H, s), 6.65(2H, m), 7.11(4H, m), 7.50(1H, m), 8.18(1H, m) |
| 151 | 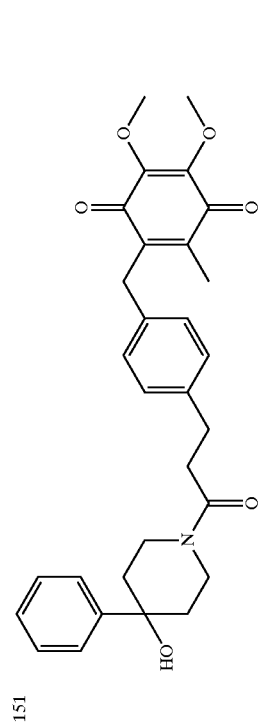 | 74 mg (48%) | powder | 486(M+H—H2O)+ | 1.70–1.79(4H, m), 2.00(1H, m), 2.07(3H, s), 2.63(2H, m), 2.94(2H, m), 3.09(1H, m), 3.41–3.48(1H, m), 3.66(1H, m), 3.79(2H, s), 3.98(6H, s), 4.59(1H, m), 7.12(4H, m), 7.28–7.45(5H, m) |
| 152 | 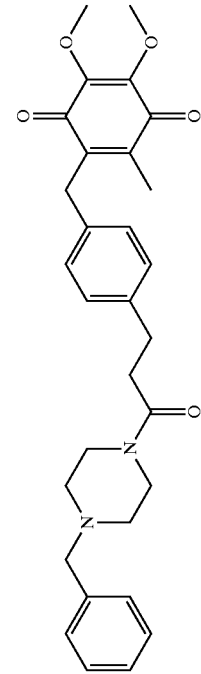 | 107 mg (70%) | oil | 503(M+H)+ | 2.08(3H, s) 2.32–2.41(4H, m) 2.57(2H, m) 2.91(2H, m) 3.38(2H, m) 3.49(2H, s), 3.62(2H, m) 3.81(2H, s) 3.98(3H, s) 3.99(3H, s) 7.10(4H, s) 7.26–7.34(5H, m) |

| | | | | |
|---|---|---|---|---|
| 153 | [structure] | 118 mg (80%) | oil | 491(M+H)⁺ | 2.07(3H, s) 2.64(2H, m) 2.95(2H, m) 3.44(2H, m) 3.71(4H, m) 3.79(4H, m) 3.98(6H, s) 6.54(1H, s) 7.12(4H, m) 8.32(2H, d, J=4.6Hz) |
| 154 | [structure] | 140 mg (86%) | oil | 520(M+H−H2O)⁺ | 1.68–1.79(4H, m), 1.94(1H, m), 2.07(3H, s), 2.62(2H, m), 2.94(2H, m), 3.07(1H, m), 3.36–3.45(1H, m), 3.65(1H, m), 3.79(2H, s), 3.98(6H, s), 4.59(1H, m), 7.11(4H, m), 7.35(4H, m) |
| 155 | [structure] | 81 mg (63%) | oil | 428(M+H)⁺ | 1.27(1H, m) 1.41(1H, m) 1.75(1H, broad) 1.85(1H, broad) 2.09(3H, s) 2.59(2H, m) 2.92(2H, m) 3.12(2H, m) 3.63(1H, broad) 3.81(2H, s) 3.86(1H, m) 3.99(6H, s) 4.12(1H, broad) 7.11(4H, m) |
| 156 | [structure] | 77 mg (58%) | oil | 442(M+H)⁺ | 1.12(3H, d, J=6.3Hz) 1.18(3H, d, J=6.2Hz) 2.09(3H, s) 2.28(1H, m) 2.57(2H, m) 2.68(1H, m) 2.92(2H, m) 3.31(1H, broad) 3.43–3.52(2H, broad) 3.81(2H, s) 3.98(3H, s) 3.99(3H, s) 4.45(1H, d, J=13.2Hz) 7.11(4H, s) |

| | | | |
|---|---|---|---|
| 157 | [structure] | 62 mg (47%) oil | 442(M+H)+ | 1.18–1.79(5.4H, broad) 2.08, 2.09(total 3H, both s) 2.33(0.5H, broad) 2.61(2H, m) 2.80(0.8H, m) 2.92(2H, m) 3.26–3.53(3.9H, broad) 3.76(1H, m) 3.81(2H, s) 3.98(3H, s) 3.99(3H, s) 4.32(0.4, broad) 7.11(4H, m) |
| 158 | [structure] | 59 mg (50%) oil | 396(M+H)+ | 2.08(3H, s) 2.53(2H, m) 2.96(2H, m) 3.81(2H, s) 3.98(3H, s) 3.99(3H, s) 4.13(2H, broad) 4.23(2H, broad) 5.75(1H, m) 5.86(1H, m) 7.12(4H, m) |
| 159 | [structure] | 60 mg (49%) oil | 410(M+H)+ | 2.08(3H, s) 2.11(2H, broad) 2.59(2H, m) 2.93(2H, m) 3.44(1H, m) 3.63(1H, m) 3.80(2H, s) 3.84(1H, m) 3.98(3H, s) 3.99(3H, s) 4.05(1H, m) 5.63(1H, broad) 5.83(1H, broad) 7.11(4H, m) |
| 160 | [structure] | 24 mg (18%) oil | 456(M+H)+ | 1.33(1H, m) 1.54–1.70(6H, m) 1.89(1H, m) 2.08(3H, s) 2.63(2H, m) 2.83–2.94(3H, m) 3.20(1H, m) 3.55–3.65(2H, m) 3.81(2H, s) 3.98(3H, s) 3.99(3H, s) 4.85(1H, broad) 7.11(4H, m) |
| 161 | [structure] | 74 mg (54%) oil | 456(M+H)+ | 0.91–1.35(3H, broad), 1.51(2H, m) 1.60–1.73(3H, m) 2.08(3H, s) 2.54(3H, m) 2.91(3H, m) 3.69(2H, m) 3.74(1H, m) 3.81(2H, s) 3.98(3H, s) 3.99(3H, s) 4.61(1H, broad) 7.10(4H, m) |

| | | | |
|---|---|---|---|
| 162 | [structure] | 40 mg (29%) oil | 457(M+H)+ | 2.08(3H, s) 2.38(2H, m) 2.45(2H, m) 2.52–2.60(4H, m) 2.92(2H, m) 3.40(2H, m) 3.63(4H, m) 3.81(2Hm, s) 3.98(3H, s) 3.99(3H, s) 7.10(4H, m) |
| 163 | [structure] | 80 mg (51%) oil | 519(M+H)+ | 2.10(3H, s) 2.63(2H, m) 2.93–3.01(6H, m) 3.58(2H, m) 3.80(4H, s) 3.87(3H, s) 3.98(3H, s) 3.99(3H, s) 6.87–6.93(3H, s) 7.03(1H, m) 7.12(4H, m) |
| 164 | [structure] | 88 mg (58%) oil | 507(M+H)+ | 2.07(3H, s) 2.63(2H, m) 2.95(4H, m) 3.03(2H, m) 3.53(2H, m) 3.77(2H, m) 3.80(2H, s) 3.98(3H, s) 3.99(3H, s) 6.86(2H, m) 6.98(2H, m) 7.11(4H, m) |
| 165 | [structure] | 112 mg (76%) oil | 495(M+H)+ | 1.38–1.88(10H, m), 2.08(3H, s), 2.47–2.60(8H, m), 2.90(3H, m), 3.80(2H, s), 3.84(1H, m), 3.98(3H, s), 3.99(3H, s), 4.70(1H, m), 7.11(4H, m) |

| # | Structure | Yield | MS | NMR |
|---|---|---|---|---|
| 166 | 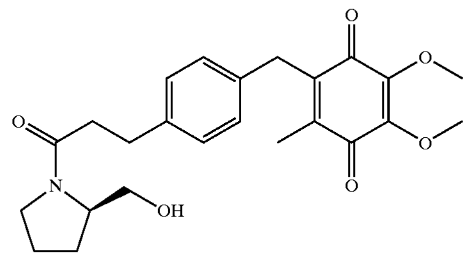 | 64 mg (50%) oil | 428(M+H)⁺ | 1.55(1H, m) 1.78(1H, m) 1.86(1H, m) 2.00(1H, m) 2.08(3H, s) 2.57(2H, m) 2.94(2H, m) 3.35(2H, m) 3.54(1H, m) 3.65(1H, m) 3.81(2H, s) 3.98(3H, s) 3.99(3H, s) 4.21(1H, m) 5.06(1H, m) 7.11(4H, m) |
| 167 | 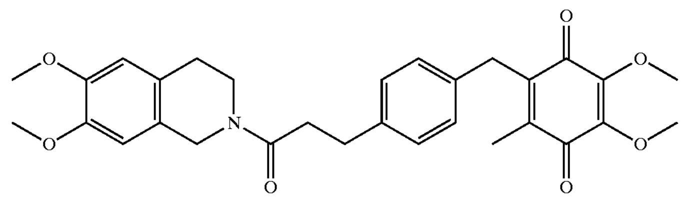 | 98 mg (63%) oil | 520(M+H)⁺ | 2.08(3H, s) 2.66(2H, m) 2.73(2H, m) 2.93(2H, m) 3.58(1.2H, m) 3.78–3.86(9.2H, m) 3.98(3H, s) 3.99(3H, s) 4.46(0.8H, s) 4.66(1.2H, s) 6.49, 6.60, 6.63(total 2H, all s) 7.10(4H, m) |
| 168 | 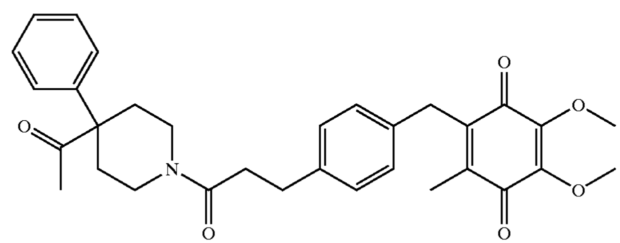 | 83 mg (52%) oil | 530(M+H)⁺ | 1.67(1H, m) 1.91(3H, s) 2.06(3H, s) 2.08(1H, m) 2.36(2H, m) 2.57(2H, m) 2.89(2H, m) 3.08(2H, m) 3.33(1H, m) 3.54(1H, m) 3.75(2H, s) 3.98(3H, s) 3.99(3H, s) 4.23(1H, m) 7.09(4H, m) 7.24–7.31(3H, m) 7.38(2H, m) |
| 169 | 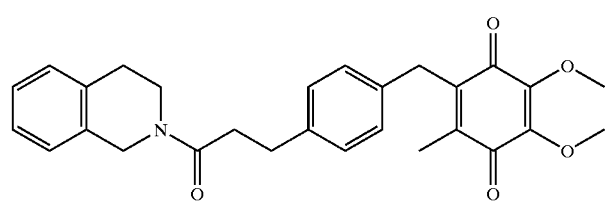 | 95 mg (69%) oil | 460(M+H)⁺ | 2.08(3H, s) 2.67(2H, m) 2.82(2H, m) 2.95(2H, m) 3.59(1.2H, m) 3.81(2.8H, m) 3.98(3H, s) 3.99(3H, s) 4.53(0.8H, s) 4.73(1.2H, s) 7.01–7.20(8H, m) |

| | | | | |
|---|---|---|---|---|
| 170 | [structure] | 98 mg (77%) oil | 426(M+H)+ | 2.08(3H, s) 2.26(2H, m) 2.42(2H, m) 2.68(2H, m) 2.94(2H, m) 3.64(2H, m) 3.80(2H, s) 3.87(2H, m) 3.99(6H, s) 7.12(4H, m) |
| 171 | [structure] | 80 mg (67%) powder | 400(M+H)+ | 0.82(6H, d, J=6.6Hz) 1.67(1H, m) 2.07(3H, s) 2.44(2H, m) 2.91(2H, m) 3.03(2H, s) 3.80(2H, s) 3.98(3H, s) 3.99(3H, s) 5.31(1H, broad) 7.09(4H, s) |
| 172 | [structure] | 107 mg (89%) powder | 400(M+H)+ | 1.27(9H, s) 2.07(3H, s) 2.33(2H, m) 2.88(2H, m) 3.81(2H, s) 3.98(3H, s) 3.99(3H, s) 5.07(1H, broad) 7.09(4H, s) |
| 173 | [structure] | 86 mg (69%) powder | 414(M+H)+ | 0.88(6H, d, J=6.6Hz) 1.31(2H, m) 1.52(1H, m) 2.07(3H, s) 2.41(2H, m) 2.91(2H, m) 3.22(2H, m) 3.80(2H, s) 3.98(3H, s) 3.99(3H, s) 5.24(1H, broad) 7.09(4H, s) |
| 174 | [structure] | 79 mg (60%) powder | 428(M+H)+ | 0.88(3H, m) 1.27(6H, broad) 1.42(2H, broad) 2.07(3H, s) 2.41(2H, m) 2.91(2H, m) 3.20(2H, s) 3.80(2H, s) 3.98(3H, s) 3.99(3H, s) 5.29(1H, broad) 7.09(4H, s) |

| # | | | NMR |
|---|---|---|---|
| 175 | [structure: 2,3-dimethoxy-5-methyl-1,4-benzoquinone with CH2-phenyl-CH2CH2C(O)NH-cyclohexyl] | 65 mg (50%) powder 426(M+H)+ | 0.99(2H, broad) 1.12(1H, broad) 1.32(2H, broad) 1.61(3H, broad) 1.81(2H, broad) 2.07(3H, s) 2.39(2H, m) 2.90(2H, m) 3.72(1H, m) 3.81(2H, s) 3.98(3H, s) 3.99(2H, s) 5.11(1H, broad) 7.09(4H, s) |
| 176 | [structure with cyclopentyl amide] | 67 mg (54%) powder 412(M+H)+ | 1.23(2H, m) 1.56(4H, m) 1.91(2H, m) 2.07(3H, s) 2.38(2H, m) 2.90(2H, m) 3.81(2H, s) 3.98(3H, s) 3.99(3H, s) 4.15(1H, m) 5.18(1H, broad) 7.09(4H, s) |
| 177 | [structure with cyclopropyl amide] | 61 mg (53%) powder 384(M+H)+ | 0.37(2H, m) 0.72(2H, m) 2.08(3H, s) 2.37(2H, m) 2.64(1H, m) 2.89(2H, m) 3.81(2H, s) 3.98(3H, s) 3.99(3H, s) 5.39(1H, broad) 7.08(4H, s) |
| 178 | [structure with cyclopropylmethyl amide] | 66 mg (55%) powder 398(M+H)+ | 0.13(2H, m) 0.45(2H, m) 0.86(1H, m) 2.08(3H, s) 2.44(2H, m) 2.92(2H, m) 3.06(2H, s) 3.81(2H, s) 3.98(3H, s) 3.99(3H, s) 5.39(1H, broad) 7.10(4H, s) |
| 179 | [structure with phenyl amide] | 65 mg (52%) powder 420(M+H)+ | 2.08(3H, s) 2.62(2H, m) 3.01(2H, m) 3.81(2H, s) 3.98(6H, s) 6.96(1H, broad) 7.12(5H, m) 7.30(2H, s) 7.42(2H, d, J=8.0Hz) |

| | | | |
|---|---|---|---|
| 180 | [structure] | 73 mg (56%) oil | 435(M+H)+ | 2.07(3H, s) 2.55(2H, m) 2.96(2H, m) 3.80(2H, s) 3.98(3H, s) 3.99(3H, s) 4.54(2H, d, J=4.9Hz) 6.65(1H, broad) 7.10(4H, m) 7.20(2H, m) 7.65(1H, m) 8.51(1H, s) |
| 181 | [structure] | 45 mg (35%) oil | 435(M+H)+ | 2.08(3H, s) 2.49(2H, m) 2.94(2H, m) 3.81(2H, s) 3.99(6H, s) 4.41(2H, d, J=5.9Hz) 5.67(1H, broad) 7.08(4H, m) 7.24(1H, d, J=7.6Hz) 8.44(1H, s) 8.51(1H, d, J=4.7Hz) |
| 182 | [structure] | 67 mg (51%) powder | 435(M+H)+ | 2.08(3H, s) 2.54(2H, m) 2.95(2H, m) 3.82(2H, s) 3.99(6H, s) 4.41(2H, d, J=6.1Hz) 5.75(1H, broad) 7.04(2H, d, J=5.5Hz) 7.10(4H, m) 8.51(2H, d, J=5.9Hz) |
| 183 | [structure] | 83 mg (65%) oil | 426(M+H)+ | 1.51(4H, broad) 1.66(4H, broad) 2.08(3H, s) 2.57(2H, m) 2.93(2H, m) 3.36(2H, m) 3.52(2H, s) 3.81(2H, s) 3.98(3H, s) 3.99(3H, s) 7.11(4H, m) |

| | | |
|---|---|---|
| 184 |  16 mg (56%) powder | (DMSO-d6) 1.96(3H, s), 2.58(2H, m), 2.83(2H, m), 3.74(2H, s), 3.87(3H, s), 3.88(3H, s), 6.78(1H, m), 6.99(1H, s), 7.07(2H, m), 7.14(2H, m), 7.55(1H, m), 9.77(1H, s) |
| 185 | 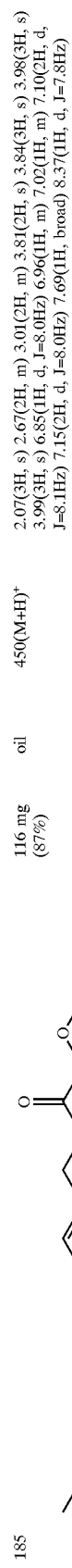 116 mg (87%) oil 450(M+H)+ | 2.07(3H, s) 2.67(2H, m) 3.01(2H, m) 3.81(2H, s) 3.84(3H, s) 3.98(3H, s) 3.99(3H, s) 6.85(1H, d, J=8.0Hz) 6.96(1H, m) 7.02(1H, m) 7.10(2H, d, J=8.1Hz) 7.15(2H, d, J=8.0Hz) 7.69(1H, broad) 8.37(1H, d, J=7.8Hz) |
| 186 | 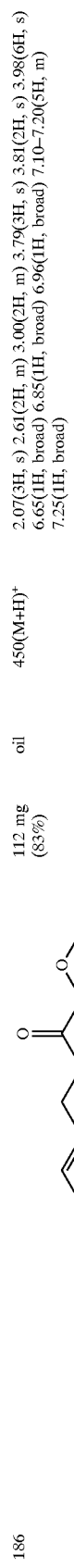 112 mg (83%) oil 450(M+H)+ | 2.07(3H, s) 2.61(2H, m) 3.00(2H, m) 3.79(3H, s) 3.81(2H, s) 3.98(6H, s) 6.65(1H, broad) 6.85(1H, broad) 6.96(1H, broad) 7.10–7.20(5H, m) 7.25(1H, broad) |

| | | | | |
|---|---|---|---|---|
| 187 | structure with 2,4-dimethoxyphenyl amide | 108 mg (76%) | oil | 480(M+H)⁺ | 2.07(3H, s), 2.64(2H, m), 3.00(2H, m), 3.79(3H, s), 3.81(3H, s), 3.83(2H, s), 3.98(3H, s), 3.99(3H, s), 6.45(2H, m), 7.13(4H, m), 7.47(1H, broad s), 8.23(1H, m) |
| 188 | structure with 6-methoxypyridin-3-yl amide | 103 mg (77%) | powder | 451(M+H)⁺ | 2.08(3H, s), 2.62(2H, m), 3.00(2H, m), 3.81(2H, s) 3.90(3H, s) 3.98(6H, s) 6.71(1H, d, J=8.9Hz) 6.87(1H, broad) 7.13(4H, m) 7.81(1H, m) 8.02(1H, m) |
| 189 | structure with 4-hydroxyphenyl amide | 84 mg (64%) powder | | 436(M+H)⁺ | (DMSO-d6) 1.96(3H, s), 2.83(2H, m), 3.74(2H, s), 3.87(3H, s), 3.88(3H, s), 6.66(2H, m), 7.07(2H, m), 7.13(2H, m), 9.13(1H, s), 9.61(1H, s) |

Experiment 1. Gel Shift Method

According to the gel shift method, a protein that binds to the NF-κB binding sequence [115th base to 106th base upstream of the transcription initiation point (No. -115 to No. -106), 17th (G) to 26th (C) in SEQ ID NO: 1] on the 5'-flanking sequence [131st base to 97th base upstream of the transcription initiation point (No. -131 to No. -97); SEQ ID NO: 1] of the hiNOS gene can be observed by cytokine stimulation.

The gel shift method was carried out as follows: the present sequence (SEQ ID NO: 1) was labelled by digoxigenin (DIG), which was incubated with a nuclear fraction extracted from A549 cells available from ATCC (CCL185) and then was electrophoresed at 4° C. using a 7.5% polyacrylamide gel. The nuclear fractions of the cell were extracted from the non-stimulated cells, the cells stimulated for 4 hours with IL-1β (1 ng/ml) or CM (human IL-1β (1 ng/ml)+human IFN-γ (1000 U/ml)+human TNF-α (500 ng/ml)) by the method of Schreiber et al. (Auphan, N., DiDonato, J. A., Rosette, C., Helmberg, A. and Karin, M. (1995) Science 270: 286–290). The DNA in the electrophoresed gel was transferred to a nylon membrane by electrotransferring and the DIG-labelled DNA was detected as a chemiluminescence DIG-recognition antibody.

Figure 1:
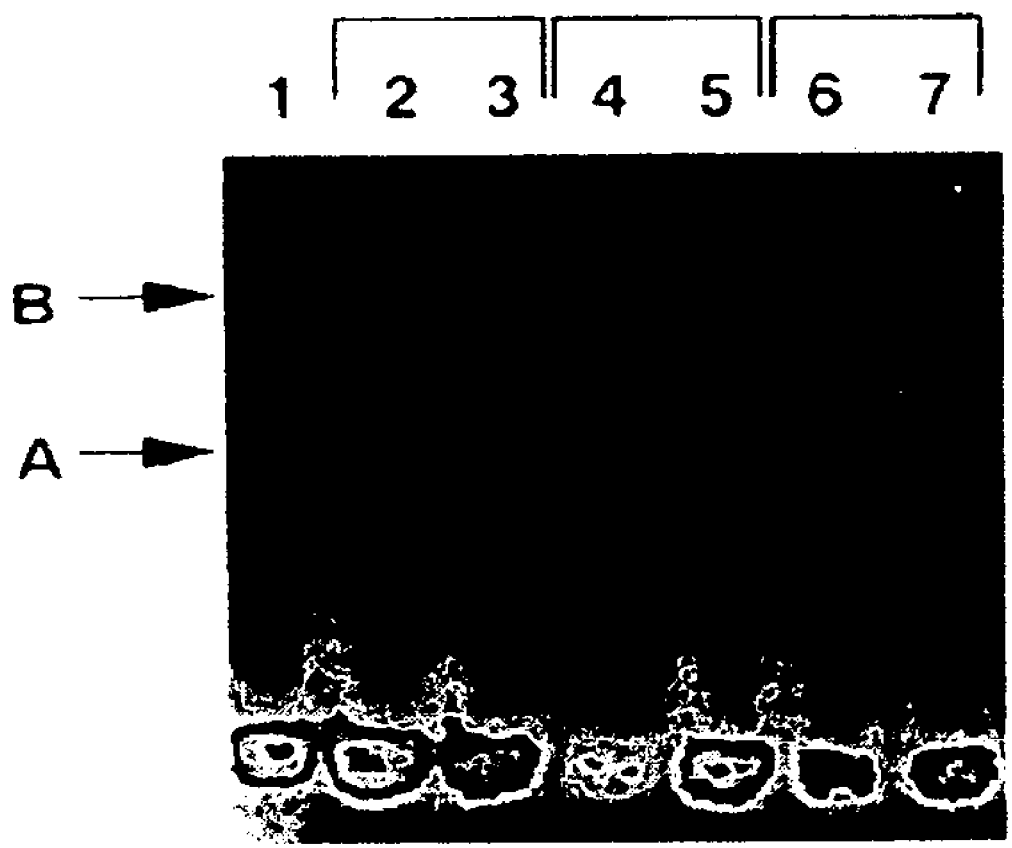
FIG. 1 shows a result of the gel shift assay of a nuclear extract when A549 cells were stimulated with a cytokine. Lane 1: no extract, lanes 2 and 3: no cytokine stimulation, lanes 4 and 5: stimulated for 4 hours with IL-1β, and lanes 6 and 7: stimulated for 4 hours with CM. In lanes 3, 5, and 7, a 20-fold concentrate of DIG-free probe was added.

FIG. 1 shows the result of the above experiment, which revealed that there is a protein (A) that binds to the present sequence in the A549 nuclear fraction in a non-specific manner in the case of non-stimulation. However, it was found that stimulation with IL-1β or CM results in the binding of another stronger binding protein (B). These findings have indicated that cytokine stimulation of the cells activates NF-κB.

Figure 2:
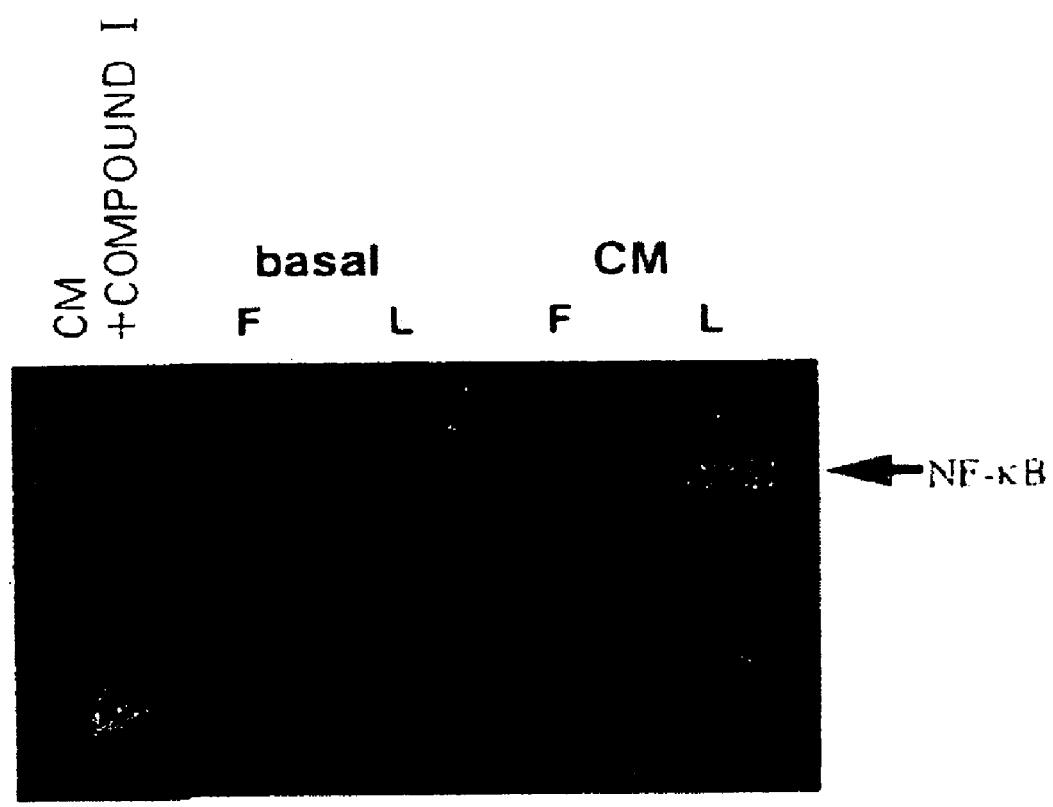
FIG. 2 shows that the compound obtained in Example 4 inhibits the activation of NF-κB after stimulation with CM as measured by a gel shift assay.

It was demonstrated that the prior addition of the compound (20 μg/ml) of the present invention obtained in Example 4 under this experimental condition inhibits the activation of NF-κB of A549 cells caused by CM stimulation (FIG. 2).

Experiment 2. Effect on Human Lung Carcinoma Cell Line A549 (A549/NF-κBLuc) that has Stably Introduced a Luciferase Plasmid (pNFκB-Luc, Stratagene, U.S.A.) Regulated by the NF-κB Binding Sequence.

Using lipofectamine (Lifetech Oriental K.K., Tokyo) according to the conventional method, A549 cells were co-transfected with pNFκB-Luc and pSV2neo (Clontech, U.S.A.), and then A549/NF-κBLuc, the cell that has stably introduced pNFκB-Luc, was selected by adding G418 sulfate (1 mg/ml, Lifetech Oriental K.K.) to the culture medium.

It was confirmed and revealed that when A549/NF-κBLuc is stimulated with IL-1β (1 ng/ml) or TNF-α (500 ng/ml) for 4 hours, the compound obtained in Example 4 suppresses luciferase activity that has been regulated by the activation of NF-κB (FIG. 3). The luciferase activity was measured using the Luciferase Assay System (Promega, U.S.A.). IC50 values are also shown in Table 1 together with the compounds of Examples 7 and 9.

TABLE 1

| Test compound | IC50 (μM) IL-1 stimulation | IC50 (μM) TNF stimulation | Test compound | IC50 (μM) IL-1 stimulation |
|---|---|---|---|---|
| Example 3 | 29 | | Example 65 | 12 |
| Example 4 | 10 | 10 | Example 66 | 3 |
| Example 7 | 4 | 10 | Example 70 | 44 |
| Example 9 | 3 | 4 | Example 71 | 56 |
| Example 23 | 42 | | Example 72 | 42 |
| Example 27 | 15 | | Example 73 | 34 |
| Example 28 | 14 | | Example 76 | 14 |
| Example 29 | 13 | | Example 79 | 13 |
| Example 30 | 14 | | Example 81 | 5 |
| Example 32 | 24 | | Example 83 | 1 |
| Example 33 | 28 | | Example 85 | 5 |
| Example 34 | 29 | | Example 94 | 1 |
| Example 35 | 8 | | Example 96 | 17 |
| Example 37 | 49 | | Example 103 | 10 |
| Example 39 | 39 | | Example 104 | 12 |
| Example 42 | 22 | | Example 105 | 16 |
| Example 43 | 21 | | Example 106 | 7 |
| Example 44 | 39 | | Example 111 | 14 |
| Example 45 | 17 | | Example 113 | 16 |
| Example 46 | 17 | | Example 120 | 2 |
| Example 47 | 21 | | Example 121 | 7 |
| Example 48 | 18 | | Example 128 | 19 |
| Example 49 | 28 | | Example 136 | 18 |
| Example 50 | 16 | | Example 137 | 7 |
| Example 51 | 18 | | Example 147 | 47 |
| Example 53 | 8 | | Example 148 | 25 |
| Example 54 | 5 | | Example 151 | 20 |
| Example 55 | 7 | | Example 154 | 28 |
| Example 56 | 5 | | Example 163 | 19 |
| Example 58 | 13 | | Example 167 | 15 |
| Example 59 | 12 | | Example 168 | 9 |
| Example 60 | 18 | | Example 169 | 43 |
| Example 61 | 24 | | Example 173 | 36 |
| Example 63 | 2 | | Example 175 | 19 |
| Example 64 | 5 | | Example 189 | 28 |

Experiment 3. Effect of Lipopolysaccharide (LPS) Stimulation on NO and TNF-α Production When various cells are stimulated with LPS, NF-κB is activated which results in the expression and induction of proteins represented by NDS and TNF-α, and thereby the cells start to produce NO and TNF-α.

The Griess' method utilizing a diazo reaction has been known as a method for indirectly knowing that a cell actually produces NO. In the Griess' method, the Griess' reagent in which naphthylethylenediamine and sulfanilic acid have been mixed is reacted with $NO_2$ ion in the culture medium, and the color development thereof is measured by absorbance at 540 nm. The amount of NO accumulated in the cell culture medium after 24 hours was measured in this method with a result that the production of NO released from LPS (10 μg/ml)-stimulated RAW264.7 cells (ATCC, TIB-71) derived from macrophage is suppressed by the compound obtained in Example 4 (FIG. 4A).

The result of measurement using the Biotrack mouse TNF-α ELISA kit (Amersham Life Science, England) revealed that the compound obtained in Example 4 can also inhibit the production of TNF-α released from the RAW264.7 cells that were stimulated with LPS (10 μg/ml) for 4 hours (FIG. 4B).

The inhibitory activity of the compounds shown in the Examples is expressed as an IC50 value.

TABLE 2

| Test compound | IC50 ($\mu$M) | |
|---|---|---|
| | NO production | TNF-$\alpha$ Production |
| Example 4 | 21 | 21 |
| Example 7 | 15 | 22 |
| Example 9 | 10 | 16 |
| Example 35 | 19 | 19 |
| Example 53 | 19 | 19 |
| Example 81 | 13 | 13 |
| Example 83 | 6 | 9 |
| Example 85 | 21 | 26 |
| Example 94 | 9 | 11 |
| Example 103 | 31 | 31 |
| Example 106 | 17 | 25 |
| Example 120 | 7 | 11 |
| Example 121 | 13 | 17 |
| Example 137 | 20 | 20 |
| Example 168 | 17 | 17 |

Furthermore, when mRNA extracted from the RAW264.7 cells was determined by a reverse transcriptase-polymerase chain reaction (RT-PCR) method, it was confirmed that the mechanism of these suppressions are based on the level of gene expression of iNOS and TNF-$\alpha$ (FIG. 5).

Experiment 4. Suppressive Effect on Carrageenin Foot Pad Edema

Experimental Method

Male Wistar rats (5 weeks old) weighing 90–120 g were used in the experiment. The rats were acclimated for one week and then were divided in following groups of eight animals:

Test compound group 1: Compound 1 (Example 4) 30 mg/kg
Test compound group 2: Compound 2 (Example 7) 50 mg/kg
Control group: 5% Dimethyl sulfoxide The test compound was given once intraperitoneally, and two hours later 0.1 ml of a prophlogistic agent was given once intradermally on the foot pad of the right hind leg of the animals to induce foot pad edema. The amount of the test compound administered was set at 10 ml/kg, and was calculated based on the body weight on the day of the experiment. The control group received the same amount of 5% dimethyl sulfoxide. As the prophlogistic agent, carrageenin (CARRAGEENAN Lambda, Sigma Chemical Company) was suspended in Japanese Pharmacopeia saline and was used as a 1% carrageenin suspension. Foot volume was measured by determining the volume of the right hind leg using a volume meter (TK-101, manufactured by Yunikomu) before the administration of the test compound, 1, 2, 3, and 4 hours after the administration of the prophlogistic agent. The edema ratio and the edema suppression ratio was calculated by the following method. The suppressive effect of the compound of the present invention on edema was confirmed (FIGS. 6 and 7):

Edema ratio (%)=(foot volume after the administration of the prophlogistic agent−foot volume before the administration of the test compound)/foot volume before the administration of the test compound×100 Edema suppression ratio (%)=(mean edema ratio of the control group−mean edema ratio of the test compound group)/mean edema ratio of the control group×100

INDUSTRIAL APPLICABILITY

Since the compounds of the present invention can inhibit the activation of NF-$\kappa$B, they are useful as preventive and/or therapeutic agents for diseases caused by the activation of NF-$\kappa$B, for example diseases caused by the excessive production of inflammatory mediators and viral propagation. More specifically the NF-$\kappa$B inhibitors of the present invention are useful as therapeutic and/or preventive agents for diseases caused by, for example, the excessive production of NO or TNF-$\alpha$ including septic shock, osteoarthritis, rheumatoid arthritis, cachexia, multiple organ failure, inflammatory bowel diseases, malaria, acquired immune deficiency syndrome, human T-cell leukemia, meningitis, hepatitis, type II diabetes, multiple sclerosis, Behcet's disease, systemic lupus erythematosus, ischemic heart disease, Alzheimer's disease, and the like.

What is claimed is:

1. A method for treatment of inflammatory diseases comprising administering to a patient in need of such treatment an effective amount of a benzoquinone derivative represented by the following general formula (I):

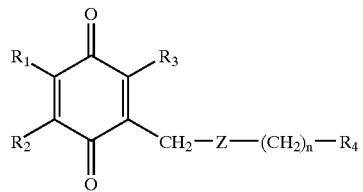

wherein

R$_1$, R$_2$ and R$_3$ are each independently a hydrogen atom, an alkyl group having 1 to 5 carbons, or an alkoxy group having 1 to 5 carbons;

R$_4$ is a hydrogen atom, a hydroxymethyl group, an alkyl group, or a carboxyl group which is optionally esterified or amidated; Z is

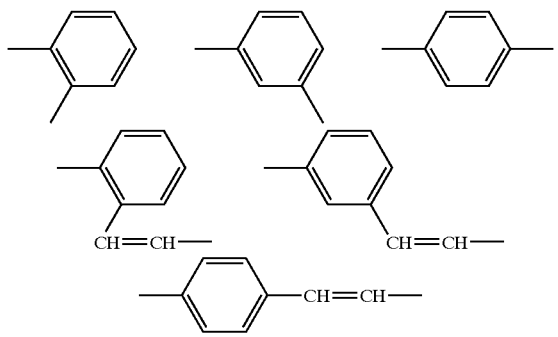

and, n is an integer from 0 to 6, or its hydroquinone form, or a pharmaceutically acceptable salt thereof.

2. The method according to claim 1 wherein R$_1$ and R$_2$ are a hydrogen atom, a methyl group, or a methoxy group.

3. The method according to claim 1 wherein R$_3$ is a hydrogen atom or a methyl group.

4. The method according to claim 1 wherein Z is

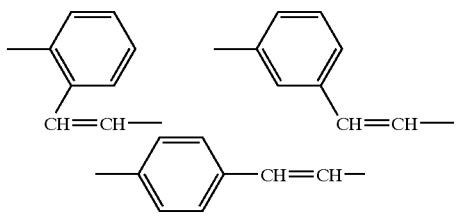

n is an integer 0.

5. The method according to claim 1 wherein Z is

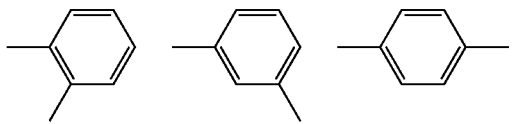

and n is an integer 1, 2, or 3.

6. The method according to claim 1 wherein R$_4$ is a group —COOR$_5$ wherein R$_5$ is a hydrogen atom, an optionally substituted alkyl group having 1 to 8 carbons, an optionally substituted phenyl group, or an optionally substituted aralkyl group having 7 to 11 carbons.

7. The method according to claim 1 wherein R$_4$ is a group —CONR$_6$R$_7$ wherein R$_6$ and R$_7$ are each independently a hydrogen atom, an optionally substituted alkyl group having 1 to 8 carbons, an optionally substituted bicyclic unsaturated or partially saturated hydrocarbon ring group having 9 to 11 carbons, an optionally substituted heterocyclic group, an optionally substituted phenyl group, an optionally substituted aralkyl group having 7 to 11 carbons, or a heteroaryl-C$_1$–C$_3$-alkyl group, or R$_6$ and R$_7$, together with the nitrogen atom to which they are attached, represent a heterocyclic group which may further contain a nitrogen, oxygen, and/or sulfur atom.

8. The method according to claim 1 wherein R$_4$ is a group —CONR$_6$R$_7$ wherein R$_6$ and R$_7$, together with the nitrogen atom to which they are attached, represent a 5- to 10-membered optionally substituted, nitrogen-containing heterocyclic group which may contain, in addition to the carbon and nitrogen atom, 1 to 3 heteroatoms selected from the group consisting of a nitrogen, oxygen and sulfur atom, the carbon atom on said cyclic group being optionally a ketone form or the sulfur atom on said cyclic group being optionally an oxide form.

9. The method according to claim 1 wherein R$_1$ and R$_2$ are a methyl group or a methoxy group; R$_3$ is a methyl group: R$_4$ is a carboxyl group which is optionally esterified or amidated; Z is

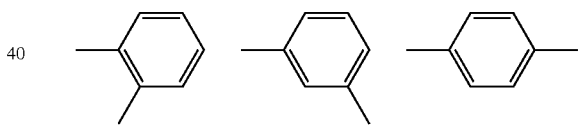

and n is an integer 1, 2, or 3.

* * * * *

SEQUENCE LISTING

```
<160> NUMBER OF SEQ ID NOS: 1

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:NF- B
      Inhibitor

<400> SEQUENCE: 1
aactgtacac aagctgggga cactcccttt ggaaa                              35
```